(12) United States Patent
Lee et al.

(10) Patent No.: US 8,188,102 B2
(45) Date of Patent: May 29, 2012

(54) AMIDE DERIVATIVE FOR INHIBITING THE GROWTH OF CANCER CELLS

(75) Inventors: Kwang-Ok Lee, Yongin-si (KR); Mi Young Cha, Seongnam-si (KR); Mi Ra Kim, Seoul (KR); Young Hee Jung, Seoul (KR); Chang Gon Lee, Yeosu-si (KR); Se Young Kim, Seongnam-si (KR); Keukchan Bang, Incheon-si (KR); Bum Woo Park, Seoul (KR); Bo Im Choi, Milyang-si (KR); Yun Jung Chae, Busan (KR); Mi Young Ko, Suwon-si (KR); Han Kyong Kim, Yongin-si (KR); Young-Gil Ahn, Seongnam-si (KR); Maeng Sup Kim, Seoul (KR); Gwan Sun Lee, Seoul (KR)

(73) Assignee: Hanmi Holdings Co., Ltd., Seoul (KR)

( * ) Notice: Subject to any disclaimer, the term of this patent is extended or adjusted under 35 U.S.C. 154(b) by 0 days.

(21) Appl. No.: 12/663,263

(22) PCT Filed: Jun. 5, 2008

(86) PCT No.: PCT/KR2008/003162
§ 371 (c)(1),
(2), (4) Date: Dec. 4, 2009

(87) PCT Pub. No.: WO2008/150118
PCT Pub. Date: Dec. 11, 2008

(65) Prior Publication Data
US 2010/0179120 A1    Jul. 15, 2010

(30) Foreign Application Priority Data
Jun. 5, 2007 (KR) ............ 10-2007-0054997

(51) Int. Cl.
*A61K 31/517* (2006.01)
(52) U.S. Cl. ............ 514/266.2; 514/266.4; 544/293
(58) Field of Classification Search ............ 544/293
See application file for complete search history.

(56) References Cited

U.S. PATENT DOCUMENTS
2008/0032996 A1  2/2008  Mitsuya et al.

FOREIGN PATENT DOCUMENTS
| WO | 03/082290 A1 | 10/2003 |
| WO | 2005/030757 A1 | 4/2005 |
| WO | 2005/090332 A1 | 9/2005 |
| WO | 2007/023073 A2 | 3/2007 |

*Primary Examiner* — James O Wilson
*Assistant Examiner* — Brian McDowell
(74) *Attorney, Agent, or Firm* — Sughrue Mion, PLLC

(57) ABSTRACT

The present invention provides a novel amide derivative of formula (I) and a pharmaceutically acceptable salt thereof, and a pharmaceutical composition comprising same as an active ingredient.

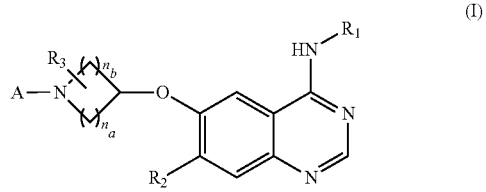

4 Claims, No Drawings

AMIDE DERIVATIVE FOR INHIBITING THE GROWTH OF CANCER CELLS

FIELD OF THE INVENTION

The present invention relates to a novel amide derivative and a pharmaceutically acceptable salt thereof which selectively and effectively inhibits the growth of cancer cells induced by the overexpression of an epidermal growth factor receptor (EGFR) and also prevents the development of drug resistance caused by the mutation of EGFR tyrosine kinase, and a pharmaceutical composition comprising same as an active ingredient.

BACKGROUND OF THE INVENTION

There are many signal transduction systems in cells which are functionally linked to each other to control the proliferation, growth, metastasis and apoptosis of cells (*Nature Reviews Cancer* 5, 689, 2005). The breakdown of the intracellular controlling system by genetic and environmental factors causes abnormal amplification or destruction of the signal transduction system leading to tumor cell generation (*Cell* 100, 57, 2000).

Protein tyrosine kinases play important roles in such cellular regulation (*Nature Reviews Drug Discovery* 3, 993, 2004), and their abnormal expression or mutation has been observed in cancer cells. The protein tyrosine kinase is an enzyme which catalyzes the transportation of phosphate groups from ATP to tyrosines located on protein substrates. Many growth factor receptor proteins function as tyrosine kinases to transport cellular signals. The interaction between growth factors and their receptors normally controls the cellular growth, but abnormal signal transduction caused by the mutation or overexpression of any of the receptors often induces tumor cells and cancers.

Protein tyrosine kinases have been classified into many families in accordance with their growth factor types, and epithelial cell growth factor (EGF)-related EGF receptor (EGFR) tyrosine kinase, in particular, have been intensely studied (*Nature Reviews Cancer* 5, 341, 2005). An EGFR tyrosine kinase is composed of a receptor and tyrosine kinase, and delivers extracellular signals to cell nucleus through the cellular membrane. Various EGFR tyrosine kinases are classified based on their structural differences into EGFR (Erb-B1), Erb-B2, Erb-B3 and Erb-B4, each of which can form a homodimer- or heterodimer-signal delivery complex. Also, the overexpression of more than one of such heterodimers is often observed in malignant cells. In addition, it is known that both EGFR and Erb-B2 significantly contribute to the formation of heterodimer-signal delivery complexes.

Several drugs as small molecules for the inhibition of EGFR tyrosine kinases have been developed, e.g., Gefitinib, Erlotinib, Lapatinib, and others. Gefitinib or Erlotinib selectively and reversibly inhibits EGFR, and Lapatinib reversibly inhibits both EGFR and Erb-B2, thereby arresting the growth of tumors to significantly extend the life time of the patient or to provide therapeutic advantages.

The small-molecule signal transfer inhibitors including EGFR tyrosine kinases have a common structural feature of quinazoline moiety, and tyrosine kinase inhibitors having quinazoline moiety are disclosed in International Publication Nos. WO 99/006396, WO 99/006378, WO 97/038983, WO 2000/031048, WO 98/050038, WO 99/024037, WO 2000/006555, WO 2001/098277, WO 2003/045939, WO 2003/049740 and WO 2005/012290; U.S. Pat. Nos. 7,019,012 and 6,225,318; and European Patent Nos. 0787722, 0387063 and 1292591.

Meanwhile, it has been well known that the development of resistance to a particular drug used causes lowering of the activity of the drug. For example, it has been reported that Gefitinib or Erlotinib generates an EGFR T790M mutant, a secondary mutation, and also that about half of the patients administered with Gefitinib or Erlotinib develop the resistance to Gefitinib or Erlotinib, and that such a drug provides no substantial clinical effect for EGFR T790M variation patients (*Public Library of Science Medicine,* 2(3), 225, 2005, *Cancer Res,* 67(24), 11924, 2007).

In this connection, it has been recently found that irreversible inhibitors to an EGFR target are more advantageous in overcoming the problem of the resistance development, as compared to the conventional reversible inhibitors such as Gefitinib and Erlotinib (*Cancer Cell* 12, 81, 2007, *Bioorganic & Medicinal Chemistry* 16, 3482, 2008). For example, irreversible inhibitors such as BIBW-2992 (*British Journal of Cancer* 98, 80, 2008), HKI-272 (*Cancer Research* 64, 3958, 2004) and AV-412 (*Cancer Sci.* 98(12), 1977, 2007) have been developed and are currently in the clinical stage. The structures of the irreversible inhibitors are shown below:

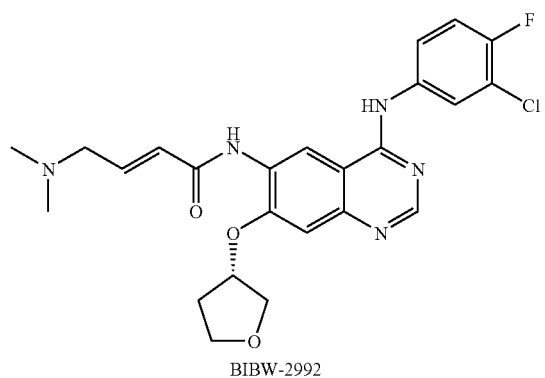

BIBW-2992

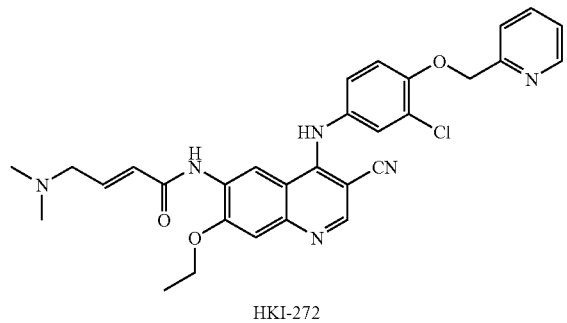

HKI-272

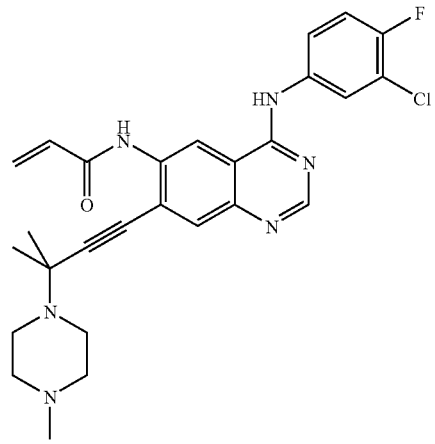

AV-412

The compounds shown above share a common structural feature of having an acrylamide functional group at the position C-6 of the quinazoline or cyanoquinoline residue, which form a covalent bond with Cystein773 (Cys773) positioned at an ATP domain of EGFR, thereby irreversibly blocking the autophosphorylation of EGFR and efficiently inhibiting the signal transfer of cancer cells (*Proc. Natl. Acad. Dci. U.S.A.* 95, 12022, 1998). They exhibit higher in vitro and in vivo inhibitory activities as compared with the conventional reversible inhibitors (*J. Med. Chem.* 42, 1803, 1999).

International Patent Publication WO 2008/032039 filed by the authors of the above literature has disclosed a novel anticancer compound having another acrylamide substituent at the position C-6 of quinazoline which shows an improved inhibition activity against EGFR tyrosine kinases.

Accordingly, there has been a continued need to develop a novel drug that has improved activity against EGFR tyrosine kinase mutants, which can effectively inhibit the development of drug-resistance induced by EGFR tyrosine kinase mutants, and while causing no adverse side effects.

SUMMARY OF THE INVENTION

Accordingly, it is an object of the present invention to provide a novel amide derivative or a pharmaceutically acceptable salt thereof which selectively and effectively inhibits the growth of cancer cells induced by the overexpression of an epidermal growth factor receptor (EGFR) and also prevents the development of drug resistance caused by the mutation of EGFR tyrosine kinase, and a pharmaceutical composition comprising same as an active ingredient.

It is another object of the present invention to provide a pharmaceutical composition for inhibiting cancer cell growth comprising said amide derivative as an active ingredient.

In accordance with one aspect of the present invention, there is provided an amide derivative of formula (I) or a pharmaceutically acceptable salt thereof:

(I)

wherein,
A is or $R_4$, $R_5$, $R_6$ and $R_7$ being each independently hydrogen, halogen, N—$C_{1-6}$ alkyl or N-hydroxy amido or C—$C_{1-6}$ alkyl reverse amido (—NHCOC$_{1-6}$), hydroxycarbonyl (—COOH), $C_{1-6}$ alkyloxycarbonyl (—COOC$_{1-6}$), $C_{1-6}$ alkyl, or $C_{1-6}$ alkyl substituted with a hydroxy, $C_{1-6}$ dialkylamine or heterocyclic group;

$R_1$ is an aryl or heterocyclic group substituted with one to five X, or $C_{1-6}$ alkyl substituted with aryl;

$R_2$ is hydrogen, hydroxy, $C_{1-6}$ alkoxy, or $C_{1-6}$ alkoxy substituted with $C_{1-6}$ alkoxy or heterocyclic group;

$R_3$ is hydrogen, —COOH, $C_{1-6}$ alkyloxycarbonyl, or amido N-unsubstituted or N-substituted with Y;

$n_a$ and $n_b$ are each an integer ranging from 0 to 6; in which:

X is hydrogen, halogen, hydroxy, cyano, nitro, (mono-, di-, or trihalogeno)methyl, mercapto, $C_{1-6}$ alkylthio, acrylamido, $C_{1-6}$ alkyl, $C_{1-6}$ alkenyl, $C_{1-6}$ alkynyl, $C_{1-6}$ alkoxy, aryloxy, $C_{1-6}$ dialkylamino, or $C_{1-6}$ alkyl or $C_{1-6}$ alkoxy substituted with Z, with the proviso that when the number of X is two or more, the X groups can fuse together to form a ring structure;

Y is hydroxy, $C_{1-6}$ alkyl or $C_{1-6}$ alkyl substituted with Z, the $C_{1-6}$ alkyl containing one to four of the moiety selected from the group consisting of N, O, S, SO, and $SO_2$; and Z is a $C_{1-6}$ alkyl, aryl, or heterocyclic group, said aryl group being $C_{5-12}$ monocyclic or bicyclic aromatic group, said heterocyclic group being a $C_{5-12}$ monocyclic or bicyclic aromatic or non-aromatic group containing one to four of the moiety selected from the group consisting of N, O, S, SO, and $SO_2$ and said aryl and heterocyclic group being unsubstituted, or substituted with substituents selected from the group consisting of halogen, hydroxyl, amino, nitro, cyano, $C_{1-6}$ alkyl, $C_{1-6}$ alkenyl, $C_{1-6}$ alkynyl, $C_{1-6}$ alkoxy, $C_{1-6}$ monoalkylamino and $C_{1-6}$ dialkylamino.

DETAILED DESCRIPTION OF THE INVENTION

In a preferred embodiment of the present invention, $R_1$ is 3-chloro-4-fluorophenyl, 3-chloro-2-fluorophenyl, 3-chloro-2,4-difluorophenyl, 3,4-dichloro-2-fluorophenyl, 4-bromo-3-chloro-2-fluorophenyl, 4-bromo-2-fluorophenyl, (R)-1-phenylethyl, 3-chloro-4-(3-fluorobenzyloxy)phenyl, 3-chloro-4-(pyridin-2-ylmethoxy)phenyl, 1-(3-fluorobenzyl)-1H-5-indazole, 3-ethinylphenyl, 4-chloro-2,5-dimethoxyphenyl, 4-bromo-3-methylphenyl, 4-isopropylphenyl, 3-methylphenyl, 3-bromophenyl, 3-chlorophenyl, 3,4-dichlorophenyl, 2,3,4-trifluorophenyl, 4-fluoro-3-methylphenyl, 3,4-dimethylphenyl, 4-phenyloxyphenyl, 2,3-dihydro-1H-indenyl, 4-hydroxy-3,5-dichlorophenyl, 3-hydroxy-4-chlorophenyl, 4-hydroxy-2-chlorophenyl, 2-hydroxy-4-chlorophenyl, 3-cyanophenyl, 3-trifluoromethylphenyl, 3-chloro-2-methoxyphenyl, 4-chloro-3-methylphenyl, 4-bromo-3-chlorophenyl, 4-bromo-3-fluorophenyl, 3-chloro-2-methylphenyl, 3-dimethylaminophenyl, 2-fluoro-3-trifluoromethylphenyl, 3-cyano-4-fluorophenyl, 3-cyano-4-chlorophenyl, 3-methylthiophenyl, 2-chlorophenyl, 4-chlorophenyl, 3-chlorophenylmethyl, 3-vinylphenyl, 3-nitrophenyl, 3-acrylamidophenyl, 3-mercaptophenyl, 3-chloromethylphenyl, 4-hydroxy-3-chlorophenyl or 4-hydroxy-3-fluorophenyl; $R_2$ is hydrogen, hydroxy, methoxy, ethoxy, 3-morpholinopropyloxy or methoxyethoxy; $R_3$ is hydrogen, methyloxycarbonyl, carboxyl, amido, N-methylamido, N-ethylamido, N-propylamido, N-isopropylamido, N-hydroxyamido, N-2-hydroxyethylamido, N-3-hydroxypropylamido, N-2-methoxyethylamido, N-2-methylthioethylamido, N-2-methylsulfonylethylamido, N-2-N,N'-diethylaminoethylamido, or N-2-morpholinoethylamido; $R_4$, $R_5$, $R_6$ and $R_7$ being each independently hydrogen, methyl, 4-methylpiperazinylmethyl, 4-methyl piperazinylethyl, N,N'-dimethylaminomethyl, N,N'-diethylaminomethyl, morpholinomethyl, pyrrolidin-1-ylmethyl, piperidin-1-ylmethyl, hydroxymethyl, N-methylcarboxamido, acetamido, N-hydroxyamido, methyl ester, chloro or carboxyl; and $n_a$ and $n_b$ being each independently an integer ranging from 0 to 2, in the amino derivative of formula (I).

In the present invention, the term 'halogen' refers to fluoro, chloro, bromo or iodo, unless otherwise indicated.

In the present invention, the term 'alkyl' refers to saturated monovalent hydrocarbon radicals having straight, cyclic or branched moieties, unless otherwise indicated.

Examples of more preferred compounds of formula (I) according to the present invention are:

1) 1-((3S)-3-(4-(3-chloro-2,4-difluorophenylamino)-7-methoxyquinazolin-6-yloxy)pyrrolidin-1-yl)prop-2-en-1-one;
2) (E)-1-((3S)-3-(4-(3-chloro-2,4-difluorophenylamino)-7-methoxyquinazolin-6-yloxy)pyrrolidin-1-yl)but-2-en-1-one;
3) 1-((3S)-3-(4-(3-chloro-2,4-difluorophenylamino)-7-methoxyquinazolin-6-yloxy)pyrrolidin-1-yl)but-2-yn-1-one;
4) 1-((3S)-3-(4-(3-chloro-2,4-difluorophenylamino)-7-methoxyquinazolin-6-yloxy)pyrrolidin-1-yl)-5-(4-methylpiperazin-1-yl)pent-2-yn-1-one;
5) 1-((3S)-3-(4-(3-chloro-2,4-difluorophenylamino)-7-methoxyquinazolin-6-yloxy)pyrrolidin-1-yl)-4-(dimethylamino)but-2-yn-1-one;
6) 1-((3S)-3-(4-(3-chloro-2-fluorophenylamino)-7-methoxyquinazolin-6-yloxy)pyrrolidin-1-yl)prop-2-en-1-one;
7) 1-((3S)-3-(4-(4-bromo-3-chloro-2-fluorophenylamino)-7-methoxyquinazolin-6-yloxy)pyrrolidin-1-yl)prop-2-en-1-one;
8) 1-((3S)-3-(4-(3,4-dichloro-2-fluorophenylamino)-7-methoxyquinazolin-6-yloxy)pyrrolidin-1-yl)prop-2-en-1-one;
9) 1-((3S)-3-(4-(4-bromo-2-fluorophenylamino)-7-methoxyquinazolin-6-yloxy)pyrrolidin-1-yl)prop-2-en-1-one;
10) 1-((3S)-3-(4-(3-chloro-4-(pyridin-2-ylmethoxy)phenylamino)-7-methoxyquinazolin-6-yloxy)pyrrolidin-1-yl)prop-2-en-1-one;
11) 1-((3S)-3-(7-methoxy-4-((1R)-1-phenylethylamine)quinazolin-6-yloxy)pyrrolidin-1-yl)prop-2-en-1-one;
12) 1-((3S)-3-(4-(1-(3-fluorobenzyl)-1H-indazol-5-ylamino)-7-methoxyquinazolin-6-yloxy)pyrrolidin-1-yl)prop-2-en-1-one;
13) 1-((3S)-3-(4-(3-chloro-4-fluorophenylamino)-7-methoxyquinazolin-6-yloxy)pyrrolidin-1-yl)prop-2-en-1-one;
14) 1-((3R)-3-(4-(3-chloro-4-fluorophenylamino)-7-methoxyquinazolin-6-yloxy)pyrrolidin-1-yl)prop-2-en-1-one;
15) 1-((3S)-3-(4-(3-chloro-2,4-difluorophenylamino)quinazolin-6-yloxy)pyrrolidin-1-yl)prop-2-en-1-one;
16) 1-((3S)-3-(4-(3-chloro-4-(3-fluorobenzyloxy)phenylamino)quinazolin-6-yloxy)pyrrolidin-1-yl)prop-2-en-1-one;
17) 1-(3-(4-(3-chloro-2,4-difluorophenylamino)-7-methoxyquinazolin-6-yloxy)azetidin-1-yl)prop-2-en-1-one;
18) 1-(3-(4-(3-chloro-2,4-difluorophenylamino)-7-methoxyquinazolin-6-yloxy)piperidin-1-yl)prop-2-en-1-one;
19) 1-(4-(4-(3-chloro-2,4-difluorophenylamino)-7-methoxyquinazolin-6-yloxy)piperidin-1-yl)prop-2-en-1-one;
20) 1-((3R)-3-(4-(3-chloro-2,4-difluorophenylamino)-7-methoxyquinazolin-6-yloxy)pyrrolidin-1-yl)prop-2-en-1-one;
21) N-(2-(4-(3-chloro-2,4-difluorophenylamino)-7-methoxyquinazolin-6-yloxy)ethyl)acrylamide;
22) 1-(3-(7-methoxy-4-((1R)-1-phenylethylamino)quinazolin-6-yloxy)azetidin-1-yl)prop-2-en-1-one;
23) 1-(3-(4-(3-chloro-2-fluorophenylamino)-7-methoxyquinazolin-6-yloxy)azetidin-1-yl)prop-2-en-1-one;
24) 1-(3-(4-(3,4-dichloro-2-fluorophenylamino)-7-methoxyquinazolin-6-yloxy)azetidin-1-yl)prop-2-en-1-one;
25) 1-(3-(4-(3-chloro-4-fluorophenylamino)-7-methoxyquinazolin-6-yloxy)azetidin-1-yl)prop-2-en-1-one;
26) 1-(3-(4-(3-chlorophenylamino)-7-methoxyquinazolin-6-yloxy)azetidin-1-yl)prop-2-en-1-one;
27) 3-(6-(1-acryloylazetidin-3-yloxy)-7-methoxyquinazolin-4-ylamino)benzonitrile;
28) (E)-4-(3-(4-(3-chloro-2,4-difluorophenylamino)-7-methoxyquinazolin-6-yloxy)azetidin-1-yl)-N-methyl-4-oxobut-2-enamide;
29) 1-(3-(4-(3-chloro-2,4-difluorophenylamino)-7-methoxyquinazolin-6-yloxy)azetidin-1-yl)-2-methylprop-2-en-1-one;
30) (Z)-methyl-4-(3-(4-(3-chloro-2-fluorophenylamino)-7-methoxyquinazolin-6-yloxy)azetidin-1-yl)-4-oxobut-2-enoate;
31) N-(3-3-(4-(3-chloro-2,4-difluorophenylamino)-7-methoxyquinazolin-6-yloxy)azetidin-1-yl)-3-oxoprop-1-en-2-yl)acetamide;
32) (Z)-3-chloro-1-(3-(4-(3-chloro-2,4-difluorophenylamino)-7-methoxyquinazolin-6-yloxy)azetidin-1-yl)prop-2-en-1-one;
33) (E)-3-chloro-1-(3-(4-(3-chloro-2,4-difluorophenylamino)-7-methoxyquinazolin-6-yloxy)azetidin-1-yl)prop-2-en-1-one;
34) 1-(4-(4-(3-chloro-2-fluorophenylamino)-7-methoxyquinazolin-6-yloxy)piperidin-1-yl)prop-2-en-1-one;
35) 1-(4-(7-methoxy-4-((1R)-1-phenylethylamino)quinazolin-6-yloxy)piperidin-1-yl)prop-2-en-1-one;
36) 1-(4-(4-(3,4-dichloro-2-fluorophenylamino)-7-methoxyquinazolin-6-yloxy)piperidin-1-yl)prop-2-en-1-one;
37) 1-(4-(4-(3-ethinylphenylamino)-7-methoxyquinazolin-6-yloxy)piperidin-1-yl)prop-2-en-1-one;
38) 1-(4-(4-(4-chloro-2,5-dimethoxyphenylamino)-7-methoxyquinazolin-6-yloxy)piperidin-1-yl)prop-2-en-1-one;
39) 1-(4-(4-(4-bromo-3-methylphenylamino)-7-methoxyquinazolin-6-yloxy)piperidin-1-yl)prop-2-en-1-one;
40) 1-(4-(4-(4-isopropylphenylamino)-7-methoxyquinazolin-6-yloxy)piperidin-1-yl)prop-2-en-1-one;
41) 1-(4-(4-(m-toluidino)-7-methoxyquinazolin-6-yloxy)piperidin-1-yl)prop-2-en-1-one;
42) 1-(4-(4-(3-bromophenylamino)-7-methoxyquinazolin-6-yloxy)piperidin-1-yl)prop-2-en-1-one;
43) 1-(4-(4-(3-chlorophenylamino)-7-methoxyquinazolin-6-yloxy)piperidin-1-yl)prop-2-en-1-one;
44) 1-(4-(4-(3,4-dichlorophenylamino)-7-methoxyquinazolin-6-yloxy)piperidin-1-yl)prop-2-en-1-one;
45) 1-(4-(7-methoxy-4-(2,3,4-trifluorophenylamino)quinazolin-6-yloxy)piperidin-1-yl)prop-2-en-1-one;
46) 1-(4-(4-(4-fluoro-3-methylphenylamino)-7-methoxyquinazolin-6-yloxy)piperidin-1-yl)prop-2-en-1-one;
47) 1-(4-(4-(3,4-dimethylphenylamino)-7-methoxyquinazolin-6-yloxy)piperidin-1-yl)prop-2-en-1-one;
48) 1-(4-(7-methoxy-4-(4-phenoxyphenylamino)quinazolin-6-yloxy)piperidin-1-yl)prop-2-en-1-one;
49) 1-(4-(4-(2,3-dihydro-1H-inden-5-ylamino)-7-methoxyquinazolin-6-yloxy)piperidin-1-yl)prop-2-en-1-one;
50) 1-(4-(4-(3,5-dichloro-4-hydroxyphenylamino)-7-methoxyquinazolin-6-yloxy)piperidin-1-yl)prop-2-en-1-one;
51) 1-(4-(4-(4-chloro-3-hydroxyphenylamino)-7-methoxyquinazolin-6-yloxy)piperidin-1-yl)prop-2-en-1-one;
52) 1-(4-(4-(2-chloro-4-hydroxyphenylamino)-7-methoxyquinazolin-6-yloxy)piperidin-1-yl)prop-2-en-1-one;
53) 1-(4-(4-(4-chloro-2-hydroxyphenylamino)-7-methoxyquinazolin-6-yloxy)piperidin-1-yl)prop-2-en-1-one;
54) 1-(4-(4-(3-chloro-4-(3-fluorobenzyloxy)phenylamino)-7-methoxyquinazolin-6-yloxy)piperidin-1-yl)prop-2-en-1-one;

55) 1-(4-(4-(3-chloro-4-(pyridin-2-ylmethoxy)phenylamino)-7-methoxyquinazolin-6-yloxy)piperidin-1-yl)prop-2-en-1-one;
56) 3-(6-(1-acryloylpiperidin-4-yloxy)-7-methoxyquinazolin-4-ylamino)benzonitrile;
57) 1-(4-(4-(3-chloro-4-fluorophenylamino)-7-methoxyquinazolin-6-yloxy)piperidin-1-yl)prop-2-en-1-one;
58) 1-(4-(7-methoxy-4-3-(trifluoromethyl)phenylamino)quinazolin-6-yloxy)piperidin-1-yl)prop-2-en-1-one;
59) 1-(4-(4-(3-chloro-2-methoxyphenylamino)-7-methoxyquinazolin-6-yloxy)piperidin-1-yl)prop-2-en-1-one;
60) 1-(4-(4-(4-chloro-3-methylphenylamino)-7-methoxyquinazolin-6-yloxy)piperidin-1-yl)prop-2-en-1-one;
61) 1-(4-(4-(4-bromo-3-chlorophenylamino)-7-methoxyquinazolin-6-yloxy)piperidin-1-yl)prop-2-en-1-one;
62) 1-(4-(4-(4-bromo-3-fluorophenylamino)-7-methoxyquinazolin-6-yloxy)piperidin-1-yl)prop-2-en-1-one;
63) 1-(4-(4-(3-chloro-2-methylphenylamino)-7-methoxyquinazolin-6-yloxy)piperidin-1-yl)prop-2-en-1-one;
64) 1-(4-(4-(3-(dimethylamino)phenylamino)-7-methoxyquinazolin-6-yloxy)piperidin-1-yl)prop-2-en-1-one;
65) 1-(4-(4-(2-fluoro-3-(trifluoromethyl)phenylamino)-7-methoxyquinazolin-6-yloxy)piperidin-1-yl)prop-2-en-1-one;
66) 5-(6-(1-acryloylpiperidin-4-yloxy)-7-methoxyquinazolin-4-ylamino)-2-fluorobenzonitrile;
67) 5-(6-(1-acryloylpiperidin-4-yloxy)-7-methoxyquinazolin-4-ylamino)-2-chlorobenzonitrile;
68) 1-(4-(7-methoxy-4-(3-(methylthio)phenylamino)quinazolin-6-yloxy)piperidin-1-yl)prop-2-en-1-one;
69) 1-(4-(4-(2-chlorophenylamino)-7-methoxyquinazolin-6-yloxy)piperidin-1-yl)prop-2-en-1-one;
70) 1-(4-(4-(4-chlorophenylamino)-7-methoxyquinazolin-6-yloxy)piperidin-1-yl)prop-2-en-1-one;
71) 1-(4-(4-(3-chloro-2,4-difluorophenylamino)quinazolin-6-yloxy)piperidin-1-yl)prop-2-en-1-one;
72) 1-(4-(4-(3-chlorobenzylamino)-7-methoxyquinazolin-6-yloxy)piperidin-1-yl)prop-2-en-1-one;
73) 1-(4-(7-methoxy-4-(3-vinylphenylamino)quinazolin-6-yloxy)piperidin-1-yl)prop-2-en-1-one;
74) 1-(4-(7-methoxy-4-(3-nitrophenylamino)quinazolin-6-yloxy)piperidin-1-yl)prop-2-en-1-one;
75) N-(3-(6-(1-acryloylpiperidin-4-yloxy)-7-quinazolin-4-ylamino)phenyl)acrylamide;
76) 1-(4-(4-(3-merchaptophenylamino)-7-methoxyquinazolin-6-yloxy)piperidin-1-yl)prop-2-en-1-one;
77) 1-(4-(4-(3-chloromethyl)phenylamino)-7-methoxyquinazolin-6-yloxy)piperidin-1-yl)prop-2-en-1-one;
78) 1-(4-(4-(3-chloro-4-hydroxyphenylamino)-7-methoxyquinazolin-6-yloxy)piperidin-1-yl)prop-2-en-1-one;
79) 1-(4-(4-(3-fluoro-4-hydroxyphenylamino)-7-methoxyquinazolin-6-yloxy)piperidin-1-yl)prop-2-en-1-one;
80) 1-(4-(4-(3-chloro-2,4-difluorophenylamino)-7-methoxyquinazolin-6-yloxy)piperidin-1-yl)but-2-yn-1-one;
81) 1-(4-(4-(3-chloro-2,4-difluorophenylamino)-7-methoxyquinazolin-6-yloxy)piperidin-1-yl)-3-methylbut-2-en-1-one;
82) (E)-4-(4-(4-(3-chloro-2,4-difluorophenylamino)-7-methoxyquinazolin-6-yloxy)piperidin-1-yl)-N-methyl-4-oxobut-2-enamide;
83) (Z)-methyl-(4-(4-(3-chloro-2,4-difluorophenylamino)-7-methoxyquinazolin-6-yloxy)piperidin-1-yl)-4-oxobut-2-enoate;
84) (Z)-methyl-(4-(4-(3,4-dichloro-2-difluorophenylamino)-7-methoxyquinazolin-6-yloxy)piperidin-1-yl)-4-oxobut-2-enoate;
85) (Z)-4-(4-(4-(3-chloro-2,4-difluorophenylamino)-7-methoxyquinazolin-6-yloxy)piperidin-1-yl)-4-oxobut-2-enoic acid;
86) (Z)-4-(4-(4-(3,4-dichloro-2-fluorophenylamino)-7-methoxyquinazolin-6-yloxy)piperidin-1-yl)-4-oxobut-2-enoic acid;
87) (E)-4-(4-(4-(3,4-dichloro-2-fluorophenylamino)-7-methoxyquinazolin-6-yloxy)piperidin-1-yl)-4-oxobut-2-enoic acid;
88) (E)-4-(4-(4-(3-chloro-2,4-difluorophenylamino)-7-methoxyquinazolin-6-yloxy)piperidin-1-yl)-N-hydroxy-4-oxobut-2-enamide;
89) (Z)-3-chloro-1-(4-(4-(3,4-dichloro-2-fluorophenylamino)-7-methoxyquinazolin-6-yloxy)piperidin-1-yl)prop-2-en-1-one;
90) (E)-3-chloro-1-(4-(4-(3,4-dichloro-2-fluorophenylamino)-7-methoxyquinazolin-6-yloxy)piperidin-1-yl)prop-2-en-1-one;
91) N-(3-(4-(4-(3,4-dichloro-2-fluorophenylamino)-7-methoxyquinazolin-6-yloxy)piperidin-1-yl)-3-oxoprop-1-en-2-yl)acetamide;
92) (E)-1-((3S)-3-(4-(3-chloro-2,4-difluorophenylamino)-7-methoxyquinazolin-6-yloxy)pyrrolidin-1-yl)-4-(dimethylamino)but-2-en-1-one;
93) (E)-1-((3S)-3-(4-(3-chloro-2,4-difluorophenylamino)-7-methoxyquinazolin-6-yloxy)pyrrolidin-1-yl)-4-(dimethylamino)but-2-en-1-one;
94) (E)-1-((3S)-3-(4-(3-chloro-2,4-difluorophenylamino)-7-methoxyquinazolin-6-yloxy)pyrrolidin-1-yl)-4-morpholinobut-2-en-1-one;
95) (E)-1-((3S)-3-(4-(3-chloro-2,4-difluorophenylamino)-7-methoxyquinazolin-6-yloxy)pyrrolidin-1-yl)-4-(pyrrolidin-1-yl)but-2-en-1-one;
96) (E)-1-((3S)-3-(4-(3-chloro-2-fluorophenylamino)-7-methoxyquinazolin-6-yloxy)pyrrolidin-1-yl)-4-(dimethylamino)but-2-en-1-one;
97) (E)-1-((3S)-3-(4-(3-chloro-2,4-fluorophenylamino)quinazolin-6-yloxy)pyrrolidin-1-yl)-4-(dimethylamino)but-2-en-1-one;
98) (E)-1-(4-(4-(3-chloro-2,4-difluorophenylamino)-7-methoxyquinazolin-6-yloxy)piperidin-1-yl)-4-(dimethylamino)but-2-en-1-one;
99) (E)-1-(4-(4-(3,4-dichloro-2-difluorophenylamino)-7-methoxyquinazolin-6-yloxy)piperidin-1-yl)-4-(dimethylamino)but-2-en-1-one;
100) (E)-1-(4-(4-(3-chloro-2-fluorophenylamino)-7-methoxyquinazolin-6-yloxy)piperidin-1-yl)-4-(dimethylamino)but-2-en-1-one;
101) (E)-1-(3-(4-(3-chloro-2,4-difluorophenylamino)-7-methoxyquinazolin-6-yloxy)azetidin-1-yl)-4-(dimethylamino)but-2-en-1-one;
102) (E)-1-(3-(4-(3-chloro-2-fluorophenylamino)-7-methoxyquinazolin-6-yloxy)azetidin-1-yl)-4-(dimethylamino)but-2-en-1-one;
103) (E)-N-(2-(4-(3-chloro-2,4-difluorophenylamino)-7-methoxyquinazolin-6-yloxy)ethyl)-4-(dimethylamino)but-2-enamide;
104) 1-(3-(4-(3-chloro-2,4-difluorophenylamino)-7-methoxyquinazolin-6-yloxy)azetidin-1-yl)-2-((dimethylamino)methyl)prop-2-en-1-one;
105) 1-(3-(4-(3-chloro-2,4-difluorophenylamino)-7-methoxyquinazolin-6-yloxy)azetidin-1-yl)-2-((morpholinomethyl)prop-2-en-1-one;
106) 1-(3-(4-(3-chloro-2,4-difluorophenylamino)-7-methoxyquinazolin-6-yloxy)azetidin-1-yl)-2-((4-methylpiperazin-1-yl)methyl)prop-2-en-1-one;

107) 1-(3-(4-(3-chloro-2-fluorophenylamino)-7-methoxyquinazolin-6-yloxy)azetidin-1-yl)-2-(piperidin-1-ylmethyl)prop-2-en-1-one;
108) 1-(3-(4-(3-chloro-2,4-difluorophenylamino)-7-methoxyquinazolin-6-yloxy)azetidin-1-yl)-2-(piperidin-1-ylmethyl)prop-2-en-1-one;
109) 1-(4-(4-(3-chloro-2,4-difluorophenylamino)-7-methoxyquinazolin-6-yloxy)piperidin-1-yl)-2-((dimethylamino)methyl)prop-2-en-1-one;
110) 1-(4-(4-(3-chloro-2,4-difluorophenylamino)-7-methoxyquinazolin-6-yloxy)piperidin-1-yl)-2-(morpholinomethyl)prop-2-en-1-one;
111) 1-(4-(4-(3,4-dichloro-2-fluorophenylamino)-7-methoxyquinazolin-6-yloxy)piperidin-1-yl)-2-((dimethylamino)methyl)prop-2-en-1-one;
112) (Z)-1-(3-(4-(3-chloro-2,4-difluorophenylamino)-7-methoxyquinazolin-6-yloxy)azetidin-1-yl)-4-(dimethylamino)but-2-en-1-one;
113) (Z)-1-(4-(4-(3-chloro-2,4-difluorophenylamino)-7-methoxyquinazolin-6-yloxy)piperidin-1-yl)-2-(dimethylamino)but-2-en-1-one;
114) 1-(4-(4-(3,4-dichloro-2-fluorophenylamino)-7-methoxyquinazolin-6-yloxy)piperidin-1-yl)-2-(hydroxymethyl)prop-2-en-1-one;
115) 1-(3-(4-(3-chloro-2,4-difluorophenylamino)-7-hydroxyquinazolin-6-yloxy)azetidin-1-yl)prop-2-en-1-one;
116) 1-(3-(4-(3-chloro-2,4-difluorophenylamino)-7-(2-methoxyethoxy)quinazolin-6-yloxy)azetidin-1-yl)prop-2-en-1-one;
117) 1-(4-(4-(3-chloro-2,4-difluorophenylamino)-7-(2-methoxyethoxy)quinazolin-6-yloxy)piperidin-1-yl)prop-2-en-1-one;
118) 1-(4-(4-(3-chloro-2,4-difluorophenylamino)-7-(3-morpholinopropoxy)quinazolin-6-yloxy)piperidin-1-yl)prop-2-en-1-one;
119) (2S,4S)-methyl-1-acryloyl-4-(4-(3-chloro-2,4-difluorophenylamino)-7-methoxyquinazolin-6-yloxy)piperidin-2-carboxylate;
120) (2S,4S)-1-acryloyl-4-(4-(3-chloro-2,4-difluorophenylamino)-7-methoxyquinazolin-6-yloxy)piperidin-2-carboxamide;
121) (2S,4S)-1-acryloyl-4-(4-(3-chloro-2,4-difluorophenylamino)-7-methoxyquinazolin-6-yloxy)-N-methylpiperidin-2-carboxamide;
122) (2S,4S)-1-acryloyl-4-(4-(3-chloro-2,4-difluorophenylamino)-7-methoxyquinazolin-6-yloxy)-N-ethylpiperidin-2-carboxamide;
123) (2S,4S)-1-acryloyl-4-(4-(3-chloro-2,4-difluorophenylamino)-7-methoxyquinazolin-6-yloxy)-N-propylpiperidin-2-carboxamide;
124) (2S,4S)-1-acryloyl-4-(4-(3-chloro-2,4-difluorophenylamino)-7-methoxyquinazolin-6-yloxy)-N-isopropylpiperidin-2-carboxamide;
125) (2S,4S)-1-acryloyl-4-(4-(3-chloro-2,4-difluorophenylamino)-7-methoxyquinazolin-6-yloxy)-N-hydroxypiperidin-2-carboxamide;
126) (2S,4S)-1-acryloyl-4-(4-(3-chloro-2,4-difluorophenylamino)-7-methoxyquinazolin-6-yloxy)-N-(2-hydroxyethyl)piperidin-2-carboxamide;
127) (2S,4S)-1-acryloyl-4-(4-(3-chloro-2,4-difluorophenylamino)-7-methoxyquinazolin-6-yloxy)-N-(2-methoxyethyl)piperidin-2-carboxamide;
128) (2S,4S)-1-acryloyl-4-(4-(3-chloro-2,4-difluorophenylamino)-7-methoxyquinazolin-6-yloxy)-N-(2-(methylthio)ethyl)piperidin-2-carboxamide;
129) (2S,4S)-1-acryloyl-4-(4-(3-chloro-2,4-difluorophenylamino)-7-methoxyquinazolin-6-yloxy)-N-(2-(methylsulphonyl)ethyl)piperidin-2-carboxamide;
130) (2S,4S)-1-acryloyl-4-(4-(3-chloro-2,4-difluorophenylamino)-7-methoxyquinazolin-6-yloxy)-N-(2-(dimethylamino)ethyl)piperidin-2-carboxamide;
131) (2S,4S)-1-acryloyl-4-(4-(3-chloro-2,4-difluorophenylamino)-7-methoxyquinazolin-6-yloxy)-N-(3-hydroxypropyl)piperidin-2-carboxamide;
132) (2S,4S)-1-acryloyl-4-(4-(3-chloro-2,4-difluorophenylamino)-7-methoxyquinazolin-6-yloxy)-N-(2-morpholinoethyl)piperidin-2-carboxamide;
133) (2R,4R)-methyl-1-acryloyl-4-(4-(3-chloro-2,4-difluorophenylamino)-7-methoxyquinazolin-6-yloxy)piperidin-2-carboxamide;
134) (2R,4R)-1-acryloyl-4-(4-(3-chloro-2,4-difluorophenylamino)-7-methoxyquinazolin-6-yloxy)piperidin-2-carboxyl acid;
135) (2R,4R)-1-acryloyl-4-(4-(3-chloro-2,4-difluorophenylamino)-7-methoxyquinazolin-6-yloxy)piperidin-2-carboxamide;
136) (2R,4R)-1-acryloyl-4-(4-(3-chloro-2,4-difluorophenylamino)-7-methoxyquinazolin-6-yloxy)-N-methylpiperidin-2-carboxamide;
137) (2R,4R)-1-acryloyl-4-(4-(3-chloro-2,4-difluorophenylamino)-7-methoxyquinazolin-6-yloxy)-N-hydroxypiperidin-2-carboxamide;
138) (2R,4R)-1-acryloyl-4-(4-(3-chloro-2,4-difluorophenylamino)-7-methoxyquinazolin-6-yloxy)-N-(2-(methylsulphonyl)ethyl)piperidin-2-carboxamide;
139) (2R,4R)-1-acryloyl-4-(4-(3,4-dichloro-2-fluorophenylamino)-7-methoxyquinazolin-6-yloxy)piperidin-2-carboxamide; and
140) (2R,4R)-1-acryloyl-4-(4-(4-bromo-2-fluorophenylamino)-7-methoxyquinazolin-6-yloxy)piperidin-2-carboxamide.

A compound of formula (I) of the present invention may be prepared, for example, by the procedure shown in Reaction Scheme (I) (see [Bioorg. Med. Chem. Lett., 2001; 11: 1911] and International Patent Publication WO 2003/082831):

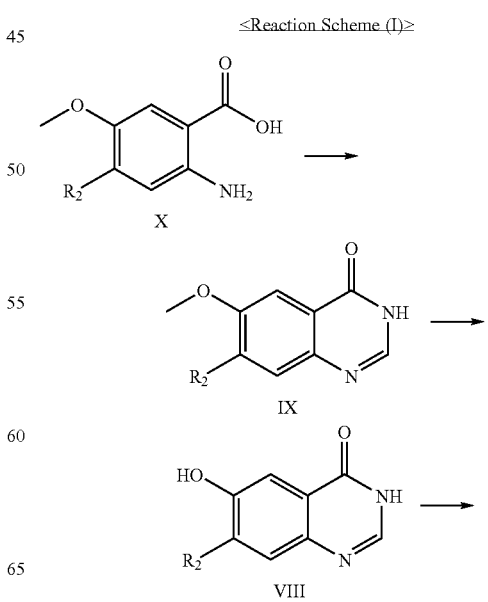

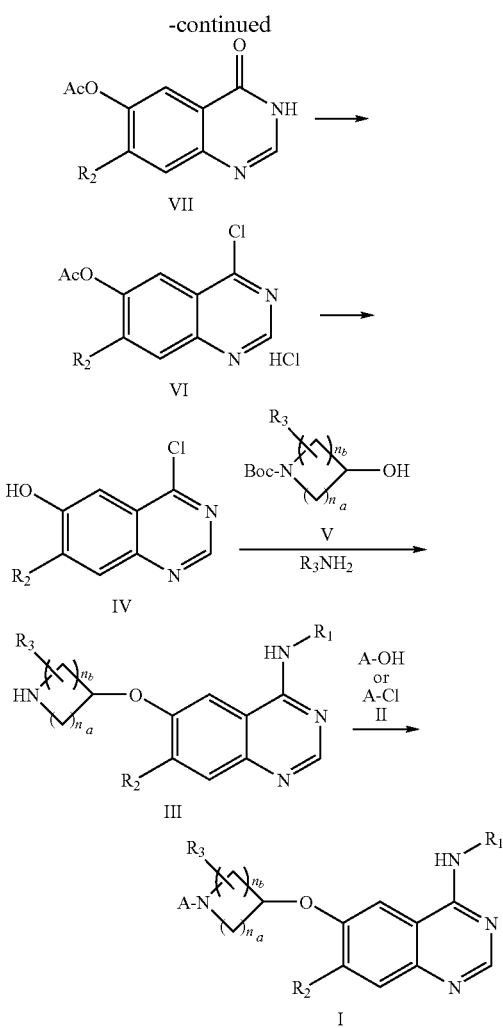

wherein,

A, $R_1$, $R_2$, $R_3$, $n_a$ and $n_b$ have the same meanings as defined above.

In Reaction Scheme (I), a compound of formula (X) is subjected to a condensation reaction with formamidine hydrochloride at a high temperature (e.g. 210° C.) to form a compound of formula (IX), followed by a reaction with L-methionine in an organic acid (e.g., methanesulfonic acid), inducing the removal of methyl at the position C-6 of the compound of formula (IX), to form a compound of formula (VIII).

Subsequently, the compound of formula (VIII) is subjected to a protection reaction in a base (e.g., pyridine) and an anhydrous acetic acid to form a compound of formula (VII), followed by a reaction with an inorganic acid (e.g., thionylchloride or phosphorous oxychloride) in the presence of a catalytic amount of dimethylformamide under a reflux condition, to form a compound of formula (VI) in a form of hydrochlorate.

The compound of formula (VI) is added to an ammonia-containing alcohol solution (e.g., a 7N ammonia-containing methanol solution), which was stirred, inducing the removal of acetyl therefrom, to form a compound of formula (IV). The compound of formula (IV) is subjected sequentially to Mitsunobu reaction with a compound of formula (V) and a substitution reaction with $R_1NH_2$ in an organic solvent (e.g., 2-propanol or acetonitrile) to introduce $R_1$ thereto. The resulting compound is subjected to a reaction with an organic or inorganic acid (e.g., trifluoroacetic acid or heavy hydrochloric acid) in an organic solvent (e.g., methylene chloride), inducing the removal of t-butoxycarbonyl, to form a compound of formula (II). In the Mitsunobu reaction, diisopropyl azodicarboxylate, diethyl azodicarboxylate, di-t-butyl azodicarboxylate or triphenylphosphine may be employed.

Subsequently, a compound of formula (I) of the present invention is prepared by subjecting the compound of formula (II) to a condensation reaction with a compound of formula (III), A-Cl, in a mixture of an organic solvent (e.g., tetrahydrofuran and water or methylene chloride in the presence of an inorganic or organic base (e.g., sodium bicarbonate, pyridine or triethylamine); or by subjecting the compound of formula (II) to a condensation reaction with a compound of formula (III), A-OH, in an organic solvent (e.g., tetrahydrofuran or methylene chloride) in the presence of a coupling agent (e.g., 1-ethyl-3-(3-dimethylaminopropyl)-carbodiimide (EDC) or 2-(1H-7-azabenzotriazol-1-yl)-1,1,3,3-tetramethyl europium hexafluorophosphate methanaminium (HATU)).

The compound of formula (I) of the present invention can also be used in the form of a pharmaceutically acceptable salt formed with an inorganic or organic acid such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

The inventive compound or a pharmaceutically acceptable salt thereof selectively and efficiently inhibits the growth of cancer cells induced by epidermal growth factor and its mutants, and provides enhanced anticancer effects when combined with another anticancer agent. Namely, the inventive compound or a pharmaceutically acceptable salt thereof is useful for enhancing the effects of an anticancer agent selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents and antiandrogen.

Therefore, the present invention provides a pharmaceutical composition for inhibiting cancer cell growth comprising the compound of formula (I) or a pharmaceutically acceptable salt thereof as an active ingredient.

The inventive compound or a pharmaceutically acceptable salt thereof may be administered orally or parenterally as an active ingredient in an effective amount ranging from about 0.01 to 100 mg/kg, preferably 0.2 to 50 mg/kg body weight per day in case of mammals including human in a single dose or in divided doses. The dosage of the active ingredient may be adjusted in light of various relevant factors such as the condition of the subject to be treated, type and seriousness of illness, administration rate, and opinion of doctor. In certain cases, an amount less than the above dosage may be suitable. An amount greater than the above dosage may be used unless it causes deleterious side effects and such amount can be administered in divided doses per day.

The inventive pharmaceutical composition may be formulated in accordance with any of the conventional methods in the form of tablet, granule, powder, capsule, syrup, emulsion or microemulsion for oral administration, or for parenteral administration including intramuscular, intravenous and subcutaneous routes.

The inventive pharmaceutical composition for oral administration may be prepared by mixing the active ingredient with a carrier such as cellulose, calcium silicate, corn starch, lactose, sucrose, dextrose, calcium phosphate, stearic acid, magnesium stearate, calcium stearate, gelatin, talc, surfactant, suspension agent, emulsifier and diluent. Examples of the carrier employed in the injectable composition of the present invention are water, a saline solution, a glucose solution, a glucose-like solution, alcohol, glycol ether (e.g., polyethylene glycol 400), oil, fatty acid, fatty acid ester, glyceride, a surfactant, a suspension agent and an emulsifier.

The following Examples are intended to further illustrate the present invention without limiting its scope.

Example 1

Preparation of 1-((3S)-3-(4-(3-chloro-2,4-difluorophenylamino)-7-methoxyquinazolin-6-yloxy)pyrrolidin-1-yl)pro-2-pen-1-one (1-1) 6,7-dimethoxyquinazolin-4(3H)-one 36.9 g of 4,5-dimethoxyanthranilic acid was mixed with 25.0 g of formamidine hydrochloride, and the mixture was stirred at 210° C. for 30 minutes. After completion of the reaction, the solid thus obtained was cooled to room temperature, stirred with 200 ml (0.33 M) of aqueous sodium hydroxide and filtered under a reduced pressure. The solid thus obtained was washed with water and air-dried to obtain the title compound (24.6 g, 64%).
$^1$H-NMR (300 MHz, DMSO-$d_6$) δ 7.99 (s, 1H), 7.44 (s, 1H), 7.13 (s, 1H), 3.90 (s, 3H), 3.87 (s, 3H).

(1-2) 6-hydroxy-7-methoxyquinazolin-4(3H)-one 3.06 g of the compound obtained in (1-1) was diluted with 20 ml of methanesulfonic acid. 2.66 g of L-methionine was added to the resulting solution and stirred at 100° C. for 22 hours. Ice was added to the reaction mixture and neutralized with 40% aqueous sodium hydroxide to induce the crystallization of the product. The solid was filtered under a reduced pressure, washed with water, and air-dried to obtain the title compound (2.67 g, 94%).
$^1$H-NMR (300 MHz, DMSO-$d_6$) δ 11.94 (s, 1H), 9.81 (s, 1H), 7.92 (s, 1H), 7.39 (s, 1H), 7.11 (s, 1H), 3.91 (s, 3H).

(1-3) 7-methoxy-4-oxo-3,4-dihydroquinazolin-6-yl acetate 6.08 g of the compound obtained in (1-2) was dissolved in a mixture of 550 ml of acetic acid and 7 ml of pyridine, and the resulting solution was stirred 100° C. for 3 hours. The reaction solution was cooled to room temperature, and ice was added thereto to induce the crystallization of the product. The solid was filtered under a reduced pressure, washed with water, and air-dried to obtain the title compound (4.87 g, 65%).
$^1$H-NMR (300 MHz, DMSO-$d_6$) δ 12.21 (s, 1H), 8.09 (s, 1H), 7.76 (s, 1H), 7.28 (s, 1H), 3.91 (s, 3H), 2.30 (s, 3H).

(1-4) 4-chloro-7-methoxyquinazolin-6-yl acetate hydrochloride salt 4.87 g of the compound obtained in (1-3) was dissolved in a mixture of 33 ml thionylchloride and 6 ml of phosphorus oxychloride. Two drops of dimethylformamide were added to the resulting solution and stirred at 120° C. for 7 hours. The reaction solution was cooled to room temperature and the solvent was removed therefrom under a reduced pressure, to obtain a residue. Toluene was added the residue, and the resulting solution was concentrated under a reduced pressure to remove the solvent, and this procedure was repeated 2 more times. The solid thus obtained was dried under a reduced pressure to obtain the title compound (5.16 g).
$^1$H-NMR (300 MHz, DMSO-$d_6$) δ 9.01 (s, 1H), 8.02 (s, 1H), 7.64 (s, 1H), 4.02 (s, 3H), 2.35 (s, 3H).

(1-5) 4-chloro-7-methoxyquinazolin-6-ol 2 g of the compound obtained in (1-4) was added to 25 ml of 7 N ammonia methanol solution. The mixture was stirred at room temperature for 1 hour, the solid formed in the reacting mixture was filtered, washed with diethylether, and dried to obtain the title compound (1.43 g, 98%).
$^1$H-NMR (300 MHz, DMSO-$d_6$) δ 8.78 (s, 1H), 7.41 (s, 1H), 7.37 (s, 1H), 4.00 (s, 3H).

(1-6) N-(3-chloro-2,4-difluorophenyl)-7-methoxy-6-((3S)-pyrrolidin-3-yloxy)quinazolin-4-amine 1.43 g of the compound obtained in (1-5), 1.91 g of (R)-(−)-N-Boc-3-pyrrolidinol and 1.96 g of triphenylphosphine were added to 20 ml of methylene chloride, and 2.01 ml of diisopropylazodicarboxylate was added thereto dropwise. The resulting mixture was stirred at room temperature for 1 hour and distilled under a reduced pressure, and the residue was briefly purified by column chromatography (ethylacetate:methylenechloride:methanol=20:20:1). The partially purified residue was then dissolved in 60 ml of 2-propanol, 1.17 g of 3-chloro-2,4-difluoroaniline was thereto, and the mixture was stirred at 100° C. for 3 hours. The resulting mixture was distilled under a reduced pressure to remove the solvent, and the residue was dissolved in 60 ml of methylenechloride. 60 ml of trifluoroacetic acid was added thereto and the mixture was stirred at room temperature for 1 hour. The resulting mixture was distilled under a reduced pressure to remove the solvent. Saturated sodium bicarbonate solution was added to the resulting residue to make it basic, followed by extraction with chloroform. The organic layer was dried over anhydrous sodium sulfate, filtered, and distilled under a reduced pressure. The resulting residue was subjected to column chromatography (chloroform:methanol=1:2) to obtain the title compound (2 g, 73%).
$^1$H-NMR (300 MHz, CDCl$_3$) δ 8.68 (s, 1H), 8.35 (m, 1H), 7.29 (s, 1H), 7.09 (s, 1H), 7.08 (m, 1H), 5.03 (bm, 1H), 4.02 (s, 3H), 3.37 (m, 1H), 3.27 (m, 1H), 3.11 (m, 1H), 3.00 (m, 1H), 2.24 (m, 1H), 2.12 (m, 1H);
MS (ESI$^+$): m/z=407.19 [M+H]$^+$.

(1-7) 1-((3S)-3-(4-(3-chloro-2,4-difluorophenylamino)-7-methoxyquinazolin-6-yloxy)pyrrolidin-1-yl)pro-2-pen-1-one 1.03 g of the compound obtained in (1-6) and 0.55 g of sodium bicarbonate were added to 40 ml of tetrahydrofuran and 6 ml of distilled water, 0.18 ml of acryloyl chloride was added thereto, and the mixture was stirred 0° C. for 30 minutes. After completion of the reaction, saturated sodium bicarbonate was added to the reaction mixture, and the resulting mixture was extracted with chloroform. The organic layer thus obtained was dried over anhydrous sodium sulfate, filtered, and distilled. The resulting residue was purified by column chromatography (chloroform:methanol=30:1) to obtain the title compound (0.7 g, 70%).

$^1$H-NMR (300 MHz, CDCl$_3$) δ 8.63 (s, 1H), 8.14 (m, 1H), 7.41 (s, 1H), 7.14 (s, 1H), 7.02 (t, 1H), 6.33 (m, 2H), 5.63 (m, 1H), 5.11 (bm, 1H), 4.03 (s, 1H), 3.94 (s, 3H), 3.78 (m, 4H), 2.46 (m, 1H), 2.28 (m, 1H);

MS (ESI$^+$): m/z=461.4 [M+H]$^+$.

Example 2

Preparation of (E)-1-((3S)-3-(4-(3-chloro-2,4-difluorophenylamino)-7-methoxyquinazolin-6-yloxy)pyrrolidin-1-yl)but-2-en-1-one The procedure of Example 1 was repeated except for using trans-crotonyl chloride instead of acryloyl chloride in step (1-7) to obtain the title compound (35 mg, 60%).

$^1$H-NMR (300 MHz, CDCl$_3$) δ 8.53 (s, 1H), 7.74 (m, 1H), 7.37 (s, 1H), 7.14 (s, 1H), 7.03 (m, 1H), 6.86 (m, 1H), 5.99 (m, 1H), 5.11 (bm, 1H), 4.09 (s, 1H), 3.94 (s, 3H), 3.81 (m, 4H), 2.46 (m, 1H), 2.29 (m, 1H), 1.83 (m, 3H);

MS (ESI$^+$): m/z=475.2 [M+H]$^+$.

Example 3

Preparation of 1-((3S)-3-(4-(3-chloro-2,4-difluorophenylamino)-7-methoxyquinazolin-6-yloxy)pyrrolidin-1-yl)but-2-yn-1-one The procedure of Example 1 was repeated except for using but-2-inoyl chloride instead of acryloyl chloride in step (1-7) to obtain the title compound (50 mg, 46%).

$^1$H-NMR (300 MHz, CDCl$_3$) δ 8.58 (s, 1H), 7.88 (m, 1H), 7.37 (s, 1H), 7.20 (s, 1H), 7.04 (t, 1H), 5.14 (bm, 1H), 3.98 (s, 3H), 3.82 (m, 4H), 2.39 (m, 1H), 2.27 (m, 1H), 1.92 (s, 3H);

MS (ESI$^+$): m/z=473.1 [M+H]$^+$.

Example 4

Preparation of 1-((3S)-3-(4-(3-chloro-2,4-difluorophenylamino)-7-methoxyquinazolin-6-yloxy)pyrrolidin-1-yl)-5-(4-methylpiperazin-1-yl)pent-2-yn-1-one The procedure of Example 1 was repeated except for using of 5-(4-methylpiperazin-1-yl)pent-2-inoyl chloride instead of acryloyl chloride in step (1-7) to obtain the title compound (65 mg, 47%).

$^1$H-NMR (300 MHz, CDCl$_3$) δ 8.60 (s, 1H), 7.98 (m, 1H), 7.33 (s, 1H), 7.23 (s, 1H), 7.05 (t, 1H), 5.14 (bm, 1H), 3.98 (s, 3H), 3.85 (m, 4H), 2.52 (m, 14H), 2.27 (s, 3H);

MS (ESI$^+$): m/z=585.2 [M+H]$^+$.

Example 5

Preparation of 1-((3S)-3-(4-(3-chloro-2,4-difluorophenylamino)-7-methoxyquinazolin-6-yloxy)pyrrolidin-1-yl)-4-(dimethylamino)but-2-yn-1-one The procedure of Example 1 was repeated except for using 4-(dimethylamino)but-2-inoyl chloride instead of acryloyl chloride in step (1-7) to obtain the title compound (50 mg, 41%).

$^1$H-NMR (300 MHz, CDCl$_3$) δ 8.59 (s, 1H), 7.97 (m, 1H), 7.37 (s, 1H), 7.23 (s, 1H), 7.04 (t, 1H), 5.15 (bm, 1H), 3.98 (s, 3H), 3.87 (m, 4H), 3.37 (s, 2H), 2.34 (m, 2H), 2.29 (s, 6H);

MS (ESI$^+$): m/z=516.2 [M+H]$^+$.

Example 6

Preparation of 1-((3S)-3-(4-(3-chloro-2-fluorophenylamino)-7-methoxyquinazolin-6-yloxy)pyrrolidin-1-yl)pro-2-pen-1-one The procedure of Example 1 was repeated except for using 3-chloro-2-fluoroaniline instead of 3-chloro-2,4-difluoroaniline in step (1-6) to obtain the title compound (10 mg, 39%).

$^1$H-NMR (300 MHz, CDCl$_3$) δ 9.82 (s, 1H), 8.77 (m, 1H), 8.64 (s, 1H), 7.11 (m, 2H), 6.93 (s, 1H), 6.46 (m, 3H), 5.72 (m, 1H), 4.00 (m, 7H), 3.75 (m, 1H), 2.50 (m, 1H);

MS (ESI$^+$): m/z=443.18 [M+H]$^+$.

Example 7

Preparation of 1-((3S)-3-(4-(4-bromo-3-chloro-2-fluorophenylamino)-7-methoxyquinazolin-6-yloxy)pyrrolidin-1-yl)pro-2-pen-1-one The procedure of Example 1 was repeated except for using 4-bromo-3-chloro-4-fluoroaniline instead of 3-chloro-2,4-difluoroaniline in step (1-6) to obtain the title compound (140 mg, 55%).

$^1$H-NMR (300 MHz, CDCl$_3$) δ 8.68 (s, 1H), 8.32 (m, 1H), 7.48 (m, 1H), 7.27 (s, 1H), 7.19 (s, 1H), 6.43 (m, 2H), 5.71 (m, 1H), 5.12 (bm, 1H), 4.03 (s, 1H), 3.99 (s, 3H), 3.83 (m, 4H), 2.49 (m, 1H), 2.31 (m, 1H);

MS (ESI$^+$): m/z=521.15 [M+H]$^+$.

Example 8

Preparation of 1-((3S)-3-(4-(3,4-dichloro-2-fluorophenylamino)-7-methoxyquinazolin-6-yloxy)pyrrolidin-1-yl)pro-2-pen-1-one The procedure of Example 1 was repeated except for using 3,4-dichloro-2-fluoroaniline instead of 3-chloro-2,4-difluoroaniline in step (1-6) to obtain the title compound (100 mg, 52%).

$^1$H-NMR (300 MHz, CDCl$_3$) δ 8.58 (s, 1H), 7.94 (m, 1H), 7.44 (s, 1H), 7.28 (s, 1H), 7.16 (s, 1H), 6.36 (m, 2H), 5.63 (m, 1H), 5.10 (bm, 1H), 3.99 (s, 1H), 3.94 (s, 3H), 3.79 (m, 4H), 2.47 (m, 1H), 2.27 (m, 1H);

MS (ESI$^+$): m/z=477.1 [M+H]$^+$.

Example 9

Preparation of 1-((3S)-3-(4-(4-bromo-2-fluorophenylamino)-7-methoxyquinazolin-6-yloxy)pyrrolidin-1-yl)pro-2-pen-1-one The procedure of Example 1 was repeated except for using 4-bromo-2-fluoroaniline instead of 3-chloro-2,4-difluoroaniline in step (1-6) to obtain the title compound (42 mg, 75%).

$^1$H-NMR (300 MHz, CDCl$_3$+CD$_3$OD) δ 8.33 (s, 1H), 7.73 (d, 1H), 7.53 (t, 1H), 7.41 (m, 2H), 7.16 (d, 1H), 6.60 (m, 1H), 6.30 (dt, 1H), 5.74 (td, 1H), 5.19 (m, 1H), 3.90 (s, 3H), 3.83 (m, 4H), 2.33 (m, 2H);

MS (ESI$^+$): m/z=487.1 [M+H]$^+$.

Example 10

Preparation of 1-((3S)-3-(4-(3-chloro-4-(pyridin-2-ylmethoxy)phenylamino)-7-methoxyquinazolin-6-yloxy)pyrrolidin-1-yl)pro-2-pen-1-one The procedure of Example 1 was repeated except for using 3-chloro-4-(pyridin-2-ylmethoxy)aniline instead of 3-chloro-2,4-difluoroaniline in step (1-6) to obtain the title compound (42 mg, 76%).

$^1$H-NMR (300 MHz, CD$_3$OD) δ 8.51 (d, 1H), 8.34 (d, 1H), 7.83 (m, 2H), 7.65 (t, 2H), 7.51 (m, 1H), 7.35 (m, 1H), 7.05 (m, 2H), 6.60 (m, 1H), 6.30 (dt, 1H), 5.73 (td, 1H), 5.18 (s, 2H), 4.85 (m, 1H), 3.90 (m, 4H), 3.89 (s, 3H), 2.31 (m, 2H);

MS (ESI$^+$): m/z=532.2 [M+H]$^+$.

Example 11

Preparation of (1-((3S)-3-(7-methoxy-4-((1R)-1-phenylethylamine)quinazolin-6-yloxy)pyrrolidin-1-yl)pro-2-pen-1-one The procedure of Example 1 was repeated except for using (R)-1-phenylethaneamine instead of 3-chloro-2,4-difluoroaniline in step (1-6) to obtain the title compound (44 mg, 67%).

$^1$H-NMR (300 MHz, CDCl$_3$) δ 8.27 (s, 1H), 7.75 (d, 1H), 7.41 (d, 2H), 7.28 (m, 2H), 7.19 (d, 1H), 7.06 (s, 1H), 6.58 (m, 1H), 6.30 (m, 1H), 5.74 (m, 1H), 5.58 (q, 1H), 5.15 (bm, 1H), 3.90 (s, 3H), 3.73 (m, 4H), 2.23 (m, 2H);

MS (ESI$^+$): m/z=419.2 [M+H]$^+$.

Example 12

Preparation of 1-((3S)-3-(4-(1-(3-fluorobenzyl)-1H-indazol-5-ylamino)-7-methoxyquinazolin-6-yloxy)pyrrolidin-1-yl)pro-2-pen-1-one The procedure of Example 1 was repeated except for using 1-(3-fluorobenzyl)-1H-indazol-5-amine instead of 3-chloro-2,4-difluoroaniline in step (1-6) to obtain the title compound (11 mg, 35%).

$^1$H-NMR (300 MHz, CDCl$_3$) δ 8.32 (s, 1H), 8.08 (s, 1H), 8.03 (m, 1H), 7.77 (d, 1H), 7.58 (m, 2H), 7.30 (m, 1H), 7.14 (d, 1H), 7.03 (m, 1H), 6.98 (m, 1H), 6.85 (m, 1H), 6.65 (m, 1H), 6.28 (m, 1H), 5.75 (m, 1H), 5.66 (s, 2H), 5.20 (bm, 1H), 3.96 (s, 3H), 3.85 (m, 4H), 2.34 (m, 2H);

MS (ESI$^+$): m/z=539.3 [M+H]$^+$.

Example 13

Preparation of 1-((3S)-3-(4-(3-chloro-4-fluorophenylamino)-7-methoxyquinazolin-6-yloxy)pyrrolidin-1-yl)pro-2-pen-1-one The procedure of Example 1 was repeated except for using 3-chloro-4-fluoroaniline instead of 3-chloro-2,4-difluoroaniline in step (1-6) to obtain the title compound (13 mg, 56%).

$^1$H-NMR (300 MHz, CD$_3$OD) δ 8.34 (s, 1H), 7.89 (m, 1H), 7.67 (d, 1H), 7.54 (m, 1H), 7.15 (t, 1H), 7.06 (m, 1H), 6.59 (m, 1H), 6.47 (m, 1H), 5.67 (m, 1H), 5.15 (m, 1H), 3.87 (s, 3H), 3.73 (m, 4H), 2.23 (m, 2H).

Example 14

Preparation of 1-((3R)-3-(4-(3-chloro-4-fluorophenylamino-7-methoxyquinazolin-6-yloxy)pyrrolidin-1-yl)pro-2-pen-1-one The procedure of Example 1 was repeated except for using (S)-(+)-N-Boc-3-pyrrolidinol instead of (R)-(−)-N-Boc-3-pyrrolidinol in step (1-6) to obtain the title compound (32 mg, 43%).

$^1$H-NMR (300 MHz, CDCl$_3$) δ 8.71 (s, 1H), 7.96 (s, 1H), 7.71 (m, 1H), 7.60 (m, 1H), 7.27 (m, 1H), 7.15 (m, 1H), 6.45 (m, 2H), 5.76 (m, 1H), 5.05 (m, 1H), 4.04 (s, 3H), 3.32 (m, 2H), 3.12 (m, 2H), 2.10 (m, 2H).

Example 15

Preparation of 1-((3S)-3-(4-(3-chloro-2,4-difluorophenylamino)quinazolin-6-yloxy)pyrrolidin-1-yl)pro-2-pen-1-one The procedure of Example 1 was repeated except for using 2-amino-5-methoxybenzoic acid instead of 4,5-dimethoxyanthranilic acid in step (1-1) to obtain the title compound (1.4 mg, 17%).

$^1$H-NMR (300 MHz, CDCl$_3$) δ 8.70 (s, 1H), 8.31 (m, 1H), 7.92 (s, 1H), 7.47 (m, 1H), 7.22 (m, 1H), 7.08 (m, 1H), 6.44 (m, 2H), 5.72 (m, 1H), 5.13 (bm, 1H), 3.99 (s, 1H), 3.76 (m, 4H), 2.30 (m, 2H);

MS (ESI$^+$): m/z=431.26 [M+H]$^+$.

Example 16

Preparation of 1-((3S)-3-(4-(3-chloro-4-(3-fluorobenzyloxy)phenylamino)quinazolin-6-yloxy)pyrrolidin-1-yl)pro-2-pen-1-one The procedure of Example 1 was repeated except for using 2-amino-5-methoxybenzoic acid instead of 4,5-dimethoxyanthranilic acid in step (1-1) and 3-chloro-4-(3-fluorobenzyloxy)-aniline instead of 3-chloro-2,4-difluoroaniline in step (1-6), respectively, to obtain the title compound (42 mg, 75%).

$^1$H-NMR (300 MHz, CD$_3$OD) δ 8.39 (d, 1H), 7.84 (t, 1H), 7.68 (m, 2H), 7.54 (m, 1H), 7.44 (m, 1H), 7.36 (dd, 1H), 7.27 (m, 2H), 7.06 (m, 2H), 6.60 (m, 1H), 6.30 (dt, 1H), 5.73 (td, 1H), 5.19 (m, 1H), 5.14 (s, 2H), 3.80 (m, 4H), 2.31 (m, 2H);

MS (ESI$^+$): m/z=519.2 [M+H]$^+$.

Example 17

Preparation of 1-(3-(4-(3-chloro-2,4-difluorophenylamino)-7-methoxyquinazolin-6-yloxy)azetidin-1-yl)pro-2-pen-1-one The procedure of Example 1 was repeated except for using N-Boc-3-hydroxy azetidine instead of (R)-(−)-N-Boc-3-pyrrolidinol in step (1-6) to obtain the title compound (90 mg, 44%).

$^1$H-NMR (300 MHz, CDCl$_3$) δ 8.62 (s, 1H), 8.16 (s, 1H), 7.87 (m, 1H), 7.30 (s, 1H), 7.20 (s, 1H), 7.03 (m, 1H), 6.21 (m, 2H), 5.65 (m, 1H), 5.13 (m, 1H), 4.66 (m, 2H), 4.51 (m, 1H), 4.21 (m, 1H), 4.03 (s, 3H);

MS (ESI$^+$): m/z=447.1 [M+H]$^+$.

Example 18

Preparation of 1-(3-(4-(3-chloro-2,4-difluorophenylamino)-7-methoxyquinazolin-6-yloxy)piperidin-1-yl)pro-2-pen-1-one The procedure of Example 1 was repeated except for using N-Boc-3-hydroxypiperidine instead of (R)-(−)-N-Boc-3-pyrrolidinol in step (1-6) to obtain the title compound (110 mg, 54%).

$^1$H-NMR (300 MHz, CDCl$_3$) δ 8.63 (s, 1H), 8.32 (s, 1H), 8.07 (s, 1H), 8.00 (m, 1H), 7.04 (m, 1H), 6.64 (m, 1H), 6.42 (m, 1H), 5.79 (dd, 1H), 4.63 (m, 1H), 4.31 (m, 1H), 4.02 (s, 3H), 3.84 (m, 1H), 3.72 (m, 1H), 3.43 (m, 1H), 3.16 (dd, 1H), 2.17 (m, 1H), 2.08 (m, 2H);

MS (ESI$^+$): m/z=475.2 [M+H]$^+$.

Example 19

Preparation of 1-(4-(4-(3-chloro-2,4-difluorophenylamino)-7-methoxyquinazolin-6-yloxy)piperidin-1-yl)pro-2-pen-1-one The procedure of Example 1 was repeated except for using N-Boc-4-hydroxypiperidine instead of (R)-(−)-N-Boc-3-pyrrolidinol in step (1-6) to obtain the title compound (25 mg, 32%).

$^1$H-NMR (300 MHz, CDCl$_3$) δ 8.63 (s, 1H), 8.09 (m, 1H), 7.79 (s, 1H), 7.42 (s, 1H), 7.29 (s, 1H), 7.04 (m, 1H), 6.58 (m, 1H), 6.25 (m, 1H), 5.68 (dd, 1H), 4.66 (m, 1H), 3.99 (s, 3H), 3.87 (m, 2H), 3.53 (m, 2H), 1.95 (m, 4H);

MS (ESI$^+$): m/z=475.2 [M+H]$^+$.

Example 20

Preparation of 1-((3R)-3-(4-(3-chloro-2,4-difluorophenylamino-7-methoxyquinazolin-6-yloxy)pyrrolidin-1-yl)pro-2-pen-1-one The procedure of Example 1 was repeated except for using (S)-(+)-N-Boc-3-pyrrolidinol instead of (R)-(−)-N-Boc-3-pyrrolidinol in step (1-6) to obtain the title compound (310 mg, 51%).

$^1$H-NMR (300 MHz, CDCl$_3$) δ 8.62 (s, 1H), 8.02 (m, 1H), 7.28 (s, 1H), 7.10 (s, 1H), 7.07 (s, 1H), 6.40 (m, 2H), 5.71 (m, 1H), 5.15 (bm, 1H), 4.08 (m, 1H), 3.99 (s, 3H), 3.86 (m, 3H), 2.32 (m, 2H);

MS (ESI$^+$): m/z=461.1 [M+H]$^+$.

Example 21

Preparation of N-(2-(4-(3-chloro-2,4-difluorophenylamino)-7-methoxyquinazolin-6-yloxy)ethyl)acrylamide The procedure of Example 1 was repeated except for using tent-butyl 2-hydroxyethylcarbamate instead of (R)-(−)-N-Boc-3-pyrrolidinol in step (1-6) to obtain the title compound (26 mg, 23%).

$^1$H-NMR (300 MHz, CDCl$_3$+CD$_3$OD) δ 9.12 (s, 1H), 8.49 (s, 1H), 7.73 (s, 1H), 7.48 (s, 1H), 7.21 (m, 1H), 6.47 (s, 2H), 5.71 (m, 1H), 4.48 (s, 2H), 4.15 (s, 3H), 3.78 (s, 2H), 3.16 (s, 2H).

Example 22

Preparation of (R)-1-(3-(7-methoxy-4-(1-phenylethylamino)quinazolin-6-yloxy)azetidin-1-yl)pro-2-pen-1-one The procedure of Example 17 was repeated except for using (R)-1-phenylethaneamine instead of 3-chloro-2,4-difluoroaniline to obtain the title compound (10 mg, 17%).

$^1$H-NMR (300 MHz, CDCl$_3$) δ 8.55 (s, 1H), 7.44 (m, 2H), 7.31 (m, 4H), 7.10 (m, 1H), 6.50 (m, 1H), 6.25 (m, 2H), 5.71 (m, 2H), 5.07 (m, 1H), 4.57 (m, 2H), 4.52 (m, 1H), 4.17 (m, 1H), 3.99 (s, 3H), 1.65 (d, 3H);

MS (ESI$^+$): m/z=405.2 [M+H]$^+$.

Example 23

Preparation of 1-(3-(4-(3-chloro-2-fluorophenylamino)-7-methoxyquinazolin-6-yloxy)azetidin-1-yl)pro-2-pen-1-one The procedure of Example 17 was repeated except for using 3-chloro-2-fluoroaniline instead of 3-chloro-2,4-difluoroaniline to obtain the title compound (20 mg, 36%).

$^1$H-NMR (300 MHz, CDCl$_3$) δ 8.67 (s, 1H), 8.09 (m, 1H), 7.35 (s, 1H), 7.28 (s, 1H), 7.16 (m, 3H), 6.23 (m, 2H), 5.68 (m, 1H), 5.13 (m, 1H), 4.66 (m, 2H), 4.47 (m, 1H), 4.24 (m, 1H), 4.04 (s, 3H);

MS (ESI$^+$): m/z=429.2 [M+H]$^+$.

Example 24

Preparation of 1-(3-(4-(3,4-dichloro-2-fluorophenylamino)-7-methoxyquinazolin-6-yloxy)azetidin-1-yl)pro-2-pen-1-one The procedure of Example 17 was repeated except for using 3,4-dichloro-2-fluoroaniline instead of 3-chloro-2,4-difluoroaniline to obtain the title compound (5 mg, 8%).

$^1$H-NMR (300 MHz, CDCl$_3$) δ 8.68 (s, 1H), 8.15 (m, 1H), 7.34 (m, 2H), 7.12 (s, 1H), 6.28 (m, 2H), 5.69 (m, 1H), 5.17 (m, 1H), 4.67 (m, 2H), 4.51 (m, 1H), 4.26 (m, 1H), 4.03 (s, 3H);

MS (ESI$^+$): m/z=463.1 [M+H]$^+$.

Example 25

Preparation of 1-(3-(4-(3-chloro-4-fluorophenylamino)-7-methoxyquinazolin-6-yloxy)azetidin-1-yl)pro-2-pen-1-one The procedure of Example 17 was repeated except for using 3-chloro-4-fluoroaniline instead of 3-chloro-2,4-difluoroaniline to obtain the title compound (50 mg, 44%).

$^1$H-NMR (300 MHz, CDCl$_3$) δ 8.44 (s, 1H), 7.94 (m, 1H), 7.61 (m, 1H), 7.48 (s, 1H), 7.24 (m, 2H), 6.29 (m, 2H), 5.74 (m, 1H), 5.22 (bm, 1H), 4.77 (m, 1H), 4.55 (m, 1H), 4.38 (m, 1H), 4.09 (m, 1H), 4.00 (s, 3H);

MS (ESI$^+$): m/z=429.2 [M+H]$^+$.

Example 26

Preparation of 1-(3-(4-(3-chlorophenylamino)-7-methoxyquinazolin-6-yloxy)azetidin-1-yl)pro-2-pen-1-one The procedure of Example 17 was repeated except for using 3-chloroaniline instead of 3-chloro-2,4-difluoroaniline to obtain the title compound (90 mg, 40%).

¹H-NMR (300 MHz, DMSO-d₆) δ 9.51 (s, 1H), 8.55 (s, 1H), 8.00 (s, 1H), 7.79 (d, 1H), 7.59 (s, 1H), 7.44 (t, 1H), 7.29 (s, 1H), 7.19 (d, 1H), 6.40 (m, 1H), 6.15 (d, 1H), 5.71 (d, 1H), 5.26 (s, 1H), 4.80 (t, 1H), 4.56 (s, 1H), 4.30 (d, 1H), 3.97 (s, 3H).

Example 27

Preparation of 3-(6-(1-acryloylazetidin-3-yloxy)-7-methoxyquinazolin-4-ylamino)benzonitrile The procedure of Example 17 was repeated except for using 3-aminobenzonitrile instead of 3-chloro-2,4-difluoroaniline to obtain the title compound (90 mg, 40%).
¹H-NMR (300 MHz, DMSO-d₆) δ 9.51 (s, 1H), 8.55 (s, 1H), 8.00 (s, 1H), 7.79 (d, 1H), 7.59 (s, 1H), 7.44 (t, 1H), 7.29 (s, 1H), 7.19 (d, 1H), 6.40 (m, 1H), 6.15 (d, 1H), 5.71 (d, 1H), 5.26 (s, 1H), 4.80 (t, 1H), 4.56 (s, 1H), 4.30 (d, 1H), 3.97 (s, 3H).

Example 28

Preparation of (E)-4-(3-(4-(3-chloro-2,4-difluorophenylamino)-7-methoxyquinazolin-6-yloxy)azetidin-1-yl)-N-methyl-4-oxobut-2-ene amide The procedure of Example 17 was repeated except for using (E)-4-(methylamino)-4-oxobut-2-enoyl chloride instead of acryloyl chloride to obtain the title compound (100 mg, 39%).
¹H-NMR (300 MHz, CDCl₃) δ 8.64 (s, 1H), 8.11 (s, 1H), 7.97 (m, 1H), 7.28 (s, 1H), 7.20 (s, 1H), 7.07 (m, 1H), 6.12 (m, 2H), 5.18 (m, 1H), 4.61 (m, 2H), 4.39 (m, 1H), 4.29 (m, 1H), 4.03 (s, 3H), 2.84 (s, 3H);
MS (ESI⁺): m/z=504.2 [M+H]⁺.

Example 29

Preparation of 1-(3-(4-(3-chloro-2,4-difluorophenylamino)-7-methoxyquinazolin-6-yloxy)azetidin-1-yl)-2-methylpro-2-pen-1-one The procedure of Example 17 was repeated except for using 2-methylacryloyl chloride instead of acryloyl chloride to obtain the title compound (58 mg, 62%).
¹H-NMR (300 MHz, CDCl₃) δ 8.68 (s, 1H), 8.10 (m, 1H), 7.71 (bs, 1H), 7.35 (s, 1H), 7.07 (m, 1H), 7.05 (s, 1H), 6.44 (d, 1H), 5.37 (s, 1H), 5.16 (m, 1H), 4.69 (m, 2H), 4.45 (m, 1H), 4.25 (m, 1H), 4.07 (s, 3H), 1.94 (s, 3H);
MS (ESI⁺): m/z=461.2 [M+H]⁺.

Example 30

Preparation of (Z)-methyl 4-(3-(4-(3-chloro-2-fluorophenylamino)-7-methoxyquinazolin-6-yloxy)azetidin-1-yl)-4-oxobut-2-enoate The procedure of Example 17 was repeated except for using 3-chloro-2-fluorophenylamine instead of 3-chloro-2,4-difluoroaniline and (Z)-methyl-4-chloro-4-oxobut-2-enoate instead of acryloyl chloride, respectively, to obtain the title compound (150 mg, 23%).
¹H-NMR (300 MHz, CDCl₃) δ 8.58 (s, 1H), 7.91 (m, 1H), 7.32 (s, 1H), 7.19 (m, 1H), 6.26 (d, 1H), 6.03 (d, 1H), 5.22 (m, 1H), 4.75 (m, 1H), 4.48 (m, 1H), 4.31 (m, 1H), 4.24 (m, 1H), 3.99 (s, 3H), 3.71 (s, 3H);
MS (ESI⁺): m/z=487.2 [M+H]⁺.

Example 31

Preparation of N-(3-(3-(4-(3-chloro-2,4-difluorophenylamino)-7-methoxyquinazolin-6-yloxy)azetidin-1-yl)-3-oxopro-1-en-2-yl)acetamide The procedure of Example 17 was repeated except for using 2-acetamido acryloyl chloride instead of acryloyl chloride to obtain the title compound (8 mg, 12%).
¹H-NMR (300 MHz, CDCl₃) δ 8.67 (s, 1H), 8.12 (m, 1H), 7.93 (s, 1H), 7.71 (s, 1H), 7.33 (s, 1H), 7.08 (m, 1H), 7.04 (s, 1H), 6.44 (s, 1H), 5.15 (m, 1H), 5.08 (s, 1H), 4.81 (m, 1H), 4.61 (m, 2H), 4.35 (m, 1H), 2.10 (s, 3H);
MS (ESI⁺): m/z=504.1 [M+H]⁺.

Example 32

Preparation of (Z)-3-chloro-1-(3-(4-(3-chloro-2,4-difluorophenylamino)-7-methoxyquinazolin-6-yloxy)azetidin-1-yl)pro-2-pen-1-one The procedure of Example 17 was repeated except for using (Z)-3-chloroacryloyl chloride instead of acryloyl chloride to obtain the title compound (20 mg, 33%).
¹H-NMR (300 MHz, CDCl₃) δ 8.65 (s, 1H), 8.06 (m, 1H), 7.70 (s, 1H), 7.32 (s, 1H), 7.05 (m, 2H), 6.50 (d, 1H), 6.15 (d, 1H), 5.18 (m, 1H), 4.72 (m, 1H), 4.60 (m, 1H), 4.47 (m, 1H), 4.26 (m, 1H), 4.04 (s, 3H);
MS (ESI⁺): m/z=481.2 [M+H]⁺.

Example 33

Preparation of (E)-3-chloro-1-(3-(4-(3-chloro-2,4-difluorophenylamino)-7-methoxyquinazolin-6-yloxy)azetidin-1-yl)pro-2-pen-1-one The procedure of Example 17 was repeated except for using (E)-3-chloroacryloyl chloride instead of acryloyl chloride to obtain the title compound (18 mg, 30%).
¹H-NMR (300 MHz, CDCl₃) δ 8.69 (s, 1H), 8.28 (m, 1H), 7.34 (s, 1H), 7.22 (s, 1H), 7.08 (m, 1H), 6.91 (s, 1H), 6.32 (d, 1H), 5.17 (m, 1H), 4.61 (m, 2H), 4.48 (m, 1H), 4.29 (m, 1H), 4.05 (s, 3H);
MS (ESI⁺): m/z=481.2 [M+H]⁺.

Example 34

Preparation of 1-(4-(4-(3-chloro-2-fluorophenylamino)-7-methoxyquinazolin-6-yloxy)piperidin-1-yl)pro-2-pen-1-one The procedure of Example 19 was repeated except for using 3-chloro-2-fluoroaniline instead of 3-chloro-2,4-difluoroaniline to obtain the title compound (7 mg, 23%).
¹H-NMR (300 MHz, CDCl₃) δ 8.69 (s, 1H), 8.36 (m, 1H), 7.32 (s, 2H), 7.16 (m, 2H), 6.61 (m, 1H), 6.29 (m, 1H), 5.71 (m, 1H), 4.72 (m, 1H), 4.01 (s, 3H), 3.90 (m, 2H), 3.72 (m, 1H), 3.57 (m, 1H), 1.97 (m, 4H);
MS (ESI⁺): m/z=457.2 [M+H]⁺.

Example 35

Preparation of (R)-1-(4-(7-methoxy-4-(1-phenylethylamino)quinazolin-6-yloxy)piperidin-1-yl)pro-2-pen-1-one The procedure of Example 19 was repeated except for using (R)-1-phenylethaneamine instead of 3-chloro-2,4-difluoroaniline to obtain the title compound (11 mg, 30%).

$^1$H-NMR (300 MHz, CDCl$_3$) δ 8.52 (s, 1H), 7.43 (m, 2H), 7.35 (m, 3H), 7.27 (m, 1H), 7.23 (s, 1H), 6.59 (m, 1H), 6.28 (m, 1H), 5.68 (m, 2H), 4.62 (m, 1H), 3.95 (s, 3H), 3.86 (m, 2H), 3.67 (m, 1H), 3.50 (m, 1H), 1.83 (m, 4H), 1.68 (d, 3H);

MS (ESI$^+$): m/z=433.3 [M+H]$^+$.

Example 36

Preparation of 1-(4-(4-(3,4-dichloro-2-fluorophenylamino)-7-methoxyquinazolin-6-yloxy)piperidin-1-yl)pro-2-pen-1-one The procedure of Example 19 was repeated except for using 3,4-dichloro-2-fluoroaniline instead of 3-chloro-2,4-difluoroaniline to obtain the title compound (3 mg, 13%).

$^1$H-NMR (300 MHz, CDCl$_3$) δ 8.68 (s, 1H), 8.39 (t, 3H), 7.31 (m, 3H), 6.61 (m, 1H), 6.29 (m, 1H), 5.72 (m, 1H), 4.75 (m, 1H), 4.02 (s, 3H), 3.89 (m, 2H), 3.60 (m, 2H), 1.86 (m, 4H);

MS (ESI$^+$): m/z=491.2 [M+H]$^+$.

Example 37

Preparation of 1-(4-(4-(3-ethynylphenylamino)-7-methoxyquinazolin-6-yloxy)piperidin-1-yl)pro-2-pen-1-one The procedure of Example 19 was repeated except for using 3-ethynylbenzeneamine instead of 3-chloro-2,4-difluoroaniline to obtain the title compound (64 mg, 30%).

$^1$H-NMR (300 MHz, DMSO-d$_6$) δ 7.90 (s, 1H), 7.75 (s, 1H), 6.96 (s, 1H), 6.93 (s, 1H), 6.80 (m, 1H), 6.57 (s, 1H), 6.08 (m, 1H), 5.65 (m, 1H), 4.63 (m, 1H), 4.29 (m, 2H), 3.71 (s, 3H), 3.60 (s, 3H), 2.61 (m, 2H), 1.94 (m, 2H), 1.61 (m, 2H).

Example 38

Preparation of 1-(4-(4-(4-chloro-2,5-dimethoxyphenylamino)-7-methoxyquinazolin-6-yloxy)piperidin-1-yl)pro-2-pen-1-one The procedure of Example 19 was repeated except for using 4-chloro-2,5-dimethoxybenzeneamine instead of 3-chloro-2,4-difluoroaniline to obtain the title compound (56 mg, 25%).

$^1$H-NMR (300 MHz, DMSO-d$_6$) δ 7.90 (s, 1H), 7.90 (s, 1H), 7.75 (s, 1H), 6.96 (s, 1H), 6.93 (s, 1H), 6.93 (s, 1H), 6.80 (m, 1H), 6.57 (s, 1H), 6.08 (m, 1H), 5.65 (m, 1H), 4.63 (m, 1H), 4.29 (m, 2H), 3.93 (s, 3H), 3.71 (s, 3H), 3.60 (s, 3H), 2.60 (m, 2H), 1.93 (m, 2H), 1.61 (m, 2H).

Example 39

Preparation of 1-(4-(4-(4-bromo-3-methylphenylamino)-7-methoxyquinazolin-6-yloxy)piperidin-1-yl)pro-2-pen-1-one The procedure of Example 19 was repeated except for using 4-bromo-3-methylbenzeneamine instead of 3-chloro-2,4-difluoroaniline to obtain the title compound (70 mg, 27%).

$^1$H-NMR (300 MHz, DMSO-d$_6$) δ 9.41 (s, 1H), 8.46 (s, 1H), 7.95 (s, 1H), 7.65 (m, 3H), 7.21 (s, 1H), 6.83 (m, 1H), 6.10 (m, 1H), 5.67 (m, 1H), 4.78 (m, 1H), 3.93 (s, 3H), 3.84 (m, 2H), 3.52 (m, 2H), 2.36 (s, 3H), 1.95 (m, 2H), 1.69 (m, 2H).

Example 40

Preparation of 1-(4-(4-(4-isopropylphenylamino)-7-methoxyquinazolin-6-yloxy)piperidin-1-yl)pro-2-pen-1-one The procedure of Example 19 was repeated except for using 4-isopropylbenzeneamine instead of 3-chloro-2,4-difluoroaniline to obtain the title compound (60 mg, 32%).

$^1$H-NMR (300 MHz, DMSO-d$_6$) δ 9.36 (s, 1H), 8.39 (s, 1H), 7.94 (s, 1H), 7.62 (d, 2H), 7.24 (d, 2H), 7.19 (s, 1H), 6.82 (m, 1H), 6.10 (m, 1H), 5.67 (m, 1H), 4.79 (m, 1H), 3.92 (s, 3H), 3.82 (m, 2H), 3.43 (m, 2H), 3.42 (m, 2H), 2.88 (m, 1H), 1.98 (m, 2H), 1.69 (m, 2H), 1.21 (d, 6H).

Example 41

Preparation of 1-(4-(4-(m-toluidino)-7-methoxyquinazolin-6-yloxy)piperidin-1-yl)pro-2-pen-1-one The procedure of Example 19 was repeated except for using m-toluidine instead of 3-chloro-2,4-difluoroaniline to obtain the title compound (70 mg, 33%).

$^1$H-NMR (300 MHz, DMSO-d$_6$) δ 8.42 (s, 1H), 8.18 (s, 1H), 7.94 (s, 1H), 7.57 (d, 1H), 7.52 (s, 1H), 7.24 (t, 1H), 6.92 (d, 1H), 6.81 (m, 1H), 6.07 (m, 1H), 5.65 (m, 1H), 4.78 (m, 1H), 3.90 (s, 3H), 3.82 (m, 2H), 3.47 (m, 2H), 2.31 (s, 3H), 1.97 (m, 2H), 1.67 (m, 2H).

Example 42

Preparation of 1-(4-(4-(3-bromophenylamino)-7-methoxyquinazolin-6-yloxy)piperidin-1-yl)pro-2-pen-1-one The procedure of Example 19 was repeated except for using 3-bromobenzeneamine instead of 3-chloro-2,4-difluoroaniline to obtain the title compound (31 mg, 34%).

$^1$H-NMR (300 MHz, CDCl$_3$) δ 8.53 (s, 1H), 7.89 (s, 1H), 7.69 (m, 1H), 7.14 (m, 2H), 6.61 (m, 1H), 6.21 (m, 1H), 5.67 (m, 1H), 4.83 (m, 1H), 3.94 (s, 3H), 3.71 (m, 1H), 3.58 (m, 2H), 1.98 (m, 2H), 1.85 (m, 2H).

Example 43

Preparation of 1-(4-(4-(3-chlorophenylamino)-7-methoxyquinazolin-6-yloxy)piperidin-1-yl)pro-2-pen-1-one The procedure of Example 19 was repeated except for using 3-chlorobenzeneamine instead of 3-chloro-2,4-difluoroaniline to obtain the title compound (19 mg, 40%).

¹H-NMR (300 MHz, CDCl₃) δ 8.64 (s, 1H), 7.81 (s, 1H), 7.62 (m, 2H), 7.29 (m, 2H), 7.09 (m, 1H), 6.59 (m, 1H), 6.28 (m, 1H), 5.71 (m, 1H), 4.68 (m, 1H), 3.94 (s, 3H), 3.88 (m, 2H), 3.48 (m, 2H), 2.29 (m, 2H), 1.94 (m, 2H).

Example 44

Preparation of 1-(4-(4-(3,4-dichlorophenylamino)-7-methoxyquinazolin-6-yloxy)piperidin-1-yl)pro-2-pen-1-one The procedure of Example 19 was repeated except for using 3,4-dichlorobenzeneamine instead of 3-chloro-2,4-difluoroaniline to obtain the title compound (47 mg, 46%).

¹H-NMR (300 MHz, CDCl₃) δ 8.51 (s, 1H), 7.92 (m, 2H), 7.62 (m, 1H), 7.30 (m, 2H), 6.62 (m, 1H), 6.28 (m, 1H), 5.69 (m, 1H), 4.98 (m, 1H), 3.97 (s, 3H), 3.86 (m, 2H), 3.58 (m, 2H), 1.88 (m, 4H).

Example 45

Preparation of 1-(4-(7-methoxy-4-(2,3,4-trifluorophenylamino)quinazolin-6-yloxy)piperidin-1-yl)pro-2-pen-1-one The procedure of Example 19 was repeated except for using 2,3,4-trifluorobenzeneamine instead of 3-chloro-2,4-difluoroaniline to obtain the title compound (3.2 mg, 3%).

¹H-NMR (300 MHz, CDCl₃) δ 8.70 (s, 1H), 8.46 (t, 1H), 7.34 (m, 2H), 7.22 (s, 1H), 6.63 (m, 1H), 6.27 (m, 1H), 5.73 (m, 1H), 4.72 (m, 1H), 4.02 (s, 3H), 3.89 (m, 2H), 3.71 (m, 1H), 3.58 (m, 1H), 2.01 (m, 2H);

MS (ESI⁺): m/z=459.3 [M+H]⁺.

Example 46

Preparation of 1-(4-(4-(4-fluoro-3-methylphenylamino)-7-methoxyquinazolin-6-yloxy)piperidin-1-yl)pro-2-pen-1-one The procedure of Example 19 was repeated except for using 4-fluoro-3-methylbenzeneamine instead of 3-chloro-2,4-difluoroaniline to obtain the title compound (57 mg, 30%).

¹H-NMR (300 MHz, DMSO-d₆) δ 9.50 (s, 1H), 8.43 (s, 1H), 7.95 (s, 1H), 7.65 (d, 2H), 7.22 (s, 1H), 7.17 (t, 1H), 6.85 (m, 1H), 6.13 (m, 1H), 5.69 (m, 1H), 4.80 (m, 1H), 3.94 (s, 3H), 3.84 (m, 2H), 3.52 (m, 2H), 3.32 (s, 3H), 2.28 (s, 3H), 1.94 (m, 2H), 1.70 (m, 2H).

Example 47

Preparation of 1-(4-(4-(3,4-dimethylphenylamino)-7-methoxyquinazolin-6-yloxy)piperidin-1-yl)pro-2-pen-1-one The procedure of Example 19 was repeated except for using 3,4-dimethylbenzeneamine instead of 3-chloro-2,4-difluoroaniline to obtain the title compound (55 mg, 24%).

¹H-NMR (300 MHz, DMSO-d₆) δ 9.29 (s, 1H), 8.39 (s, 1H), 7.94 (s, 1H), 7.48 (m, 2H), 7.18 (s, 1H), 7.12 (d, 1H), 6.82 (m, 1H), 6.09 (m, 1H), 5.67 (m, 1H), 4.78 (m, 1H), 3.92 (s, 3H), 3.84 (m, 2H), 3.49 (m, 2H), 2.24 (s, 3H), 2.21 (s, 3H), 1.99 (m, 2H), 1.68 (m, 2H).

Example 48

Preparation of 1-(4-(7-methoxy-4-(4-phenoxyphenylamino)quinazolin-6-yloxy)piperidin-1-yl)pro-2-pen-1-one The procedure of Example 19 was repeated except for using 4-phenoxybenzeneamine instead of 3-chloro-2,4-difluoroaniline to obtain the title compound (81 mg, 30%).

¹H-NMR (300 MHz, DMSO-d₆) δ 9.43 (s, 1H) 8.42 (s, 1H), 7.94 (s, 1H), 7.74 (d, 1H), 7.83 (t, 2H), 7.20 (s, 1H), 7.05 (m, 5H), 6.83 (m, 1H), 6.10 (m, 1H), 5.67 (m, 1H), 4.79 (m, 2H), 3.93 (s, 3H), 3.85 (m, 2H), 3.46 (m, 2H), 2.01 (m, 2H), 1.69 (m, 2H).

Example 49

Preparation of 1-(4-(4-(2,3-dihydro-1H-inden-5-ylamino)-7-methoxyquinazolin-6-yloxy)piperidin-1-yl)pro-2-pen-1-one The procedure of Example 19 was repeated except for using 2,3-dihydro-1H-inden-5-amine instead of 3-chloro-2,4-difluoroaniline to obtain the title compound (63 mg, 25%).

¹H-NMR (300 MHz, DMSO-d₆) δ 9.32 (s, 1H), 8.40 (s, 1H), 7.94 (s, 1H), 7.62 (s, 1H), 7.44 (d, 1H), 7.21 (d, 1H), 7.18 (s, 1H), 6.82 (m, 1H), 6.10 (d, 1H), 5.67 (d, 1H), 4.78 (m, 1H), 3.92 (s, 3H), 3.84 (m, 2H), 3.48 (m, 2H), 2.86 (q, 4H), 1.99 (m, 4H), 1.69 (m, 2H).

Example 50

Preparation of 1-(4-(4-(3,5-dichloro-4-hydroxyphenylamino)-7-methoxyquinazolin-6-yloxy)piperidin-1-yl)pro-2-pen-1-one The procedure of Example 19 was repeated except for using 4-amino-2,6-dichlorophenol instead of 3-chloro-2,4-difluoroaniline to obtain the title compound (2.1 mg, 7%).

¹H-NMR (300 MHz, CDCl₃) δ 9.05 (s, 1H), 8.87 (s, 1H), 8.66 (m, 1H), 7.83 (s, 1H), 7.36 (m, 1H), 6.82 (m, 1H), 6.24 (m, 1H), 5.61 (m, 1H), 4.79 (m, 1H), 3.99 (s, 3H), 3.52 (m, 4H), 2.24 (m, 2H), 1.93 (m, 2H).

Example 51

Preparation of 1-(4-(4-(4-chloro-3-hydroxyphenylamino)-7-methoxyquinazolin-6-yloxy)piperidin-1-yl)pro-2-pen-1-one The procedure of Example 19 was repeated except for using 5-amino-2-chlorophenol instead of 3-chloro-2,4-difluoroaniline to obtain the title compound (8 mg, 15%).

¹H-NMR (300 MHz, CDCl₃) δ 8.87 (s, 1H), 8.48 (s, 1H), 7.57 (m, 1H), 7.37 (s, 1H), 7.17 (s, 1H), 7.07 (m, 1H), 6.80 (m, 2H), 6.09 (m, 1H), 5.71 (m, 1H), 4.93 (s, 1H), 4.00 (s, 3H), 3.69 (m, 2H), 3.28 (m, 2H), 2.04 (m, 2H), 1.63 (m, 2H).

Example 52

Preparation of 1-(4-(4-(2-chloro-4-hydroxyphenylamino)-7-methoxyquinazolin-6-yloxy)piperidin-1-yl)pro-2-pen-1-one The procedure of Example 19 was repeated except for using 4-amino-3-chlorophenol instead of 3-chloro-2,4-difluoroaniline to obtain the title compound (26 mg, 40%).
$^1$H-NMR (300 MHz, DMSO-$d_6$) δ 9.92 (s, 1H), 9.33 (s, 1H), 8.31 (s, 1H), 7.87 (m, 1H), 7.27 (d, 1H), 6.96 (s, 1H), 6.83 (m, 1H), 6.80 (m, 2H), 6.09 (m, 1H), 5.71 (m, 1H), 4.74 (m, 1H), 3.92 (s, 3H), 3.46 (m, 2H), 3.26 (m, 2H), 2.02 (m, 2H), 1.67 (m, 2H).

Example 53

Preparation of 1-(4-(4-(4-chloro-2-hydroxyphenylamino)-7-methoxyquinazolin-6-yloxy)piperidin-1-yl)pro-2-pen-1-one The procedure of Example 19 was repeated except for using 2-amino-5-chlorophenol instead of 3-chloro-2,4-difluoroaniline to obtain the title compound (7.9 mg, 17%).
$^1$H-NMR (300 MHz, CD$_3$OD) δ 8.35 (s, 1H), 7.87 (m, 1H), 7.46 (d, 1H), 7.23 (s, 1H), 7.00 (m, 1H), 6.83 (m, 1H), 6.81 (m, 1H), 6.26 (m, 1H), 5.77 (m, 1H), 5.71 (m, 1H), 4.02 (s, 3H), 3.66 (m, 2H), 3.39 (m, 2H), 2.10 (m, 2H), 1.90 (m, 2H);
MS (ESI$^+$): m/z=455.2 [M+H]$^+$.

Example 54

Preparation of 1-(4-(4-(3-chloro-4-(3-fluorobenzyloxy)phenylamino)-7-methoxyquinazolin-6-yloxy)piperidin-1-yl)pro-2-pen-1-one The procedure of Example 19 was repeated except for using 3-chloro-4-(3-fluorobenzyloxy)benzeneamine instead of 3-chloro-2,4-difluoroaniline to obtain the title compound (75 mg, 27%).
$^1$H-NMR (300 MHz, DMSO-$d_6$) δ 8.39 (s, 1H), 7.81 (d, 1H), 7.80 (s, 1H), 7.03-7.68 (m, 7H), 6.80 (m, 1H), 6.23 (m, 1H), 5.76 (m, 1H), 5.20 (s, 2H), 4.82 (m, 1H), 3.99 (s, 3H), 3.96 (m, 2H), 3.68 (m, 2H), 2.04 (m, 2H), 1.92 (m, 2H).

Example 55

Preparation of 1-(4-(4-(3-chloro-4-(pyridin-2-ylmethoxy)phenylamino)-7-methoxyquinazolin-6-yloxy)piperidin-1-yl)pro-2-pen-1-one The procedure of Example 19 was repeated except for using 3-chloro-4-(pyridin-2-ylmethoxy)benzeneamine instead of 3-chloro-2,4-difluoroaniline to obtain the title compound (75 mg, 16%).
$^1$H-NMR (300 MHz, DMSO-$d_6$) δ 8.56 (d, 1H), 8.40 (s, 1H), 7.90 (m, 2H), 7.86 (d, 1H), 7.80 (s, 1H), 7.72 (d, 1H), 7.55 (m, 1H), 7.40 (t, 1H), 7.15 (m, 2H), 6.81 (m, 1H), 6.22 (m, 1H), 5.75 (m, 1H), 5.26 (s, 2H), 4.84 (m, 1H), 3.99 (s, 3H), 3.92 (m, 2H), 3.49 (m, 2H), 2.03 (m, 2H), 2.07 (m, 2H), 1.91 (m, 2H).

Example 56

Preparation of 3-(6-(1-acryloylpiperidin-4-yloxy)-7-methoxyquinazolin-4-ylamino)benzonitrile The procedure of Example 19 was repeated except for using 3-aminobenzonitrile instead of 3-chloro-2,4-difluoroaniline to obtain the title compound (27 mg, 28%).
$^1$H-NMR (300 MHz, DMSO-$d_6$) δ 9.71 (s, 1H), 8.58 (s, 1H), 8.40 (s, 1H), 8.16 (m, 1H), 8.01 (s, 1H), 7.59 (m, 2H), 7.29 (s, 1H), 6.88 (m, 1H), 6.12 (m, 1H), 5.71 (m, 1H), 4.86 (m, 1H), 3.98 (s, 3H), 3.90 (m, 2H), 3.55 (m, 1H), 2.08 (m, 1H), 1.76 (m, 1H);
MS (ESI$^+$): m/z=430.3 [M+H]$^+$.

Example 57

Preparation of 1-(4-(4-(3-chloro-4-fluorophenylamino)-7-methoxyquinazolin-6-yloxy)piperidin-1-yl)pro-2-pen-1-one The procedure of Example 19 was repeated except for using 3-chloro-4-fluoroaniline instead of 3-chloro-2,4-difluoroaniline to obtain the title compound (14 mg, 31%).
$^1$H-NMR (300 MHz, DMSO-$d_6$) δ 8.60 (s, 1H), 8.42 (s, 1H), 8.22 (m, 1H), 8.12 (m, 1H), 7.29 (s, 1H), 7.22 (m, 1H), 6.88 (m, 1H), 6.24 (m, 1H), 5.72 (m, 1H), 4.81 (m, 1H), 3.81 (s, 3H), 3.65 (m, 2H), 3.31 (m, 2H), 1.95 (m, 1H);
MS (ESI$^+$): m/z=457.2 [M+H]$^+$.

Example 58

Preparation of 1-(4-(7-methoxy-4-(3-(trifluoromethyl)phenylamino)quinazolin-6-yloxy)piperidin-1-yl)pro-2-pen-1-one The procedure of Example 19 was repeated except for using 3-(trifluoromethyl)benzeneamine instead of 3-chloro-2,4-difluoroaniline to obtain the title compound (18 mg, 21%).
$^1$H-NMR (300 MHz, DMSO-$d_6$) δ 9.66 (s, 1H), 8.63 (m, 1H), 8.41 (m, 2H), 8.02 (m, 1H), 7.46 (m, 1H), 7.26 (m, 1H), 7.13 (m, 1H), 6.86 (m, 1H), 6.12 (m, 2H), 5.79 (m, 1H), 4.95 (m, 1H), 3.96 (s, 3H), 3.87 (m, 2H), 3.53 (m, 2H), 2.03 (m, 2H), 1.21 (m, 2H);
MS (ESI$^+$): m/z=473.0 [M+H]$^+$.

Example 59

Preparation of 1-(4-(4-(3-chloro-2-methoxyphenylamino)-7-methoxyquinazolin-6-yloxy)piperidin-1-yl)pro-2-pen-1-one The procedure of Example 19 was repeated except for using 3-chloro-2-methoxybenzeneamine instead of 3-chloro-2,4-difluoroaniline to obtain the title compound (11 mg, 27%).
$^1$H-NMR (300 MHz, DMSO-$d_6$) δ 8.91 (s, 1H), 8.53 (s, 1H), 7.92 (s, 1H), 7.58 (m, 2H), 7.37 (m, 1H), 6.88 (m, 1H), 6.21 (m, 1H), 5.82 (m, 1H), 4.90 (m, 1H), 3.99 (s, 3H), 3.73 (s, 3H), 3.82 (m, 2H), 3.60 (m, 2H), 2.11 (m, 2H), 1.25 (m, 2H);
MS (ESI$^+$): m/z=469.3 [M+H]$^+$.

Example 60

Preparation of 1-(4-(4-(4-chloro-3-methylphenylamino)-7-methoxyquinazolin-6-yloxy)piperidin-1-yl)pro-2-pen-1-one The procedure of Example 19 was repeated except for using 4-chloro-3-methylbenzeneamine instead of 3-chloro-2,4-difluoroaniline to obtain the title compound (13 mg, 10%).
$^1$H-NMR (300 MHz, DMSO-$d_6$) δ 9.50 (s, 1H), 8.43 (s, 1H), 7.95 (s, 1H), 7.65 (d, 2H), 7.22 (s, 1H), 7.17 (t, 1H), 6.85

(m, 1H), 6.13 (m, 1H), 5.69 (m, 1H), 4.80 (m, 1H), 3.94 (s, 3H), 3.84 (m, 2H), 3.51 (m, 2H), 3.32 (s, 3H), 2.28 (s, 3H), 1.96 (m, 2H), 1.70 (m, 2H);
MS (ESI$^+$): m/z=453.3 [M+H]$^+$.

Example 61

Preparation of 1-(4-(4-(4-bromo-3-chlorophenylamino)-7-methoxyquinazolin-6-yloxy)piperidin-1-yl)pro-2-pen-1-one The procedure of Example 19 was repeated except for using 4-bromo-3-chlorobenzeneamine instead of 3-chloro-2,4-difluoroaniline to obtain the title compound (14 mg, 37%).
$^1$H-NMR (300 MHz, CDCl$_3$) δ 8.68 (s, 1H), 7.98 (s, 1H), 7.56 (m, 2H), 7.39 (m, 1H), 7.28 (m, 1H), 6.62 (m, 1H), 6.29 (m, 1H), 5.71 (m, 1H), 4.67 (m, 1H), 3.99 (s, 3H), 3.82 (m, 2H), 3.60 (m, 2H), 2.11 (m, 2H), 1.25 (m, 2H);
MS (ESI$^+$): m/z=517.2 [M+H]$^+$.

Example 62

Preparation of 1-(4-(4-(4-bromo-3-fluorophenylamino)-7-methoxyquinazolin-6-yloxy)piperidin-1-yl)pro-2-pen-1-one The procedure of Example 19 was repeated except for using 4-bromo-3-fluorobenzeneamine instead of 3-chloro-2,4-difluoroaniline to obtain the title compound (22 mg, 41%).
$^1$H-NMR (300 MHz, CDCl$_3$) δ 8.69 (s, 1H), 7.90 (m, 1H), 7.51 (m, 1H), 7.36 (m, 1H), 7.28 (m, 2H), 6.62 (m, 1H), 6.29 (m, 1H), 5.70 (m, 1H), 4.68 (m, 1H), 3.99 (s, 3H), 3.82 (m, 2H), 3.67 (m, 2H), 2.01 (m, 4H);
MS (ESI$^+$): m/z=501.2 [M+H]$^+$.

Example 63

Preparation of 1-(4-(4-(3-chloro-2-methylphenylamino)-7-methoxyquinazolin-6-yloxy)piperidin-1-yl)pro-2-pen-1-one The procedure of Example 19 was repeated except for using 3-chloro-2-methylbenzeneamine instead of 3-chloro-2,4-difluoroaniline to obtain the title compound (15 mg, 14%).
$^1$H-NMR (300 MHz, CDCl$_3$) δ 8.59 (s, 1H), 7.43 (m, 1H), 7.34 (m, 1H), 7.28 (m, 1H), 7.26 (m, 1H), 7.19 (m, 1H), 6.61 (m, 1H), 6.31 (m, 1H), 5.69 (m, 1H), 4.54 (m, 1H), 4.00 (s, 3H), 3.87 (m, 2H), 3.72 (m, 2H), 2.34 (s, 3H), 1.93 (m, 4H).

Example 64

Preparation of 1-(4-(4-(3-(dimethylamino)phenylamino)-7-methoxyquinazolin-6-yloxy)piperidin-1-yl)pro-2-pen-1-one The procedure of Example 19 was repeated except for using N$^1$,N$^1$-dimethylbenzen-1,3-diamine instead of 3-chloro-2,4-difluoroaniline to obtain the title compound (8 mg, 14%).
$^1$H-NMR (300 MHz, CDCl$_3$) δ 8.64 (s, 1H), 7.26 (m, 3H), 6.93 (m, 1H), 6.99 (m, 1H), 6.59 (m, 1H), 6.55 (m, 1H), 6.31 (m, 1H), 5.68 (m, 1H), 4.58 (m, 1H), 3.98 (s, 3H), 3.87 (m, 2H), 3.48 (m, 2H), 2.96 (s, 6H), 1.32 (m, 4H).

Example 65

Preparation of 1-(4-(4-(2-fluoro-3-(trifluoromethyl)phenylamino)-7-methoxyquinazolin-6-yloxy)piperidin-1-yl)pro-2-pen-1-one The procedure of Example 19 was repeated except for using 2-fluoro-3-(trifluoromethyl)benzeneamine instead of 3-chloro-2,4-difluoroaniline to obtain the title compound (29 mg, 23%).
$^1$H-NMR (300 MHz, CDCl$_3$) δ 8.87 (s, 1H), 8.63 (s, 1H), 7.87 (s, 1H), 7.50 (m, 2H), 7.43 (m, 1H), 6.85 (m, 1H), 6.26 (m, 1H), 5.82 (m, 1H), 4.90 (m, 1H), 3.99 (s, 3H), 3.82 (m, 2H), 3.60 (m, 2H), 2.11 (m, 2H), 1.25 (m, 2H).

Example 66

Preparation of 5-(6-(1-acryloylpiperidin-4-yloxy)-7-methoxyquinazolin-4-ylamino)-2-fluorobenzonitrile The procedure of Example 19 was repeated except for using 5-amino-2-fluorobenzonitrile instead of 3-chloro-2,4-difluoroaniline to obtain the title compound (28 mg, 28%).
$^1$H-NMR (300 MHz, CDCl$_3$) δ 8.69 (s, 1H), 8.65 (s, 1H), 8.18 (m, 1H), 8.07 (m, 1H), 7.29 (s, 1H), 7.21 (t, 1H), 6.61 (m, 1H), 6.20 (m, 1H), 5.68 (m, 1H), 4.71 (m, 1H), 3.92 (s, 3H), 3.71 (m, 2H), 3.48 (m, 2H), 1.19 (m, 4H);
MS (ESI$^+$): m/z=448.3 [M+H]$^+$.

Example 67

Preparation of 5-(6-(1-acryloylpiperidin-4-yloxy)-7-methoxyquinazolin-4-ylamino)-2-chlorobenzonitrile The procedure of Example 19 was repeated except for using 5-amino-2-chlorobenzonitrile instead of 3-chloro-2,4-difluoroaniline to obtain the title compound (14 mg, 21%).
$^1$H-NMR (300 MHz, CDCl$_3$) δ 8.78 (s, 1H), 8.64 (s, 1H), 8.16 (m, 1H), 8.01 (m, 1H), 7.32 (s, 1H), 7.21 (t, 1H), 6.61 (m, 1H), 6.21 (m, 1H), 5.66 (m, 1H), 4.71 (m, 1H), 3.96 (s, 3H), 3.71 (m, 2H), 3.48 (m, 2H), 1.19 (m, 4H);
MS (ESI$^+$): m/z=464.3 [M+H]$^+$.

Example 68

Preparation of 1-(4-(7-methoxy-4-(3-(methylthio)phenylamino)quinazolin-6-yloxy)piperidin-1-yl)pro-2-pen-1-one The procedure of Example 19 was repeated except for using 3-(methylthio)benzeneamine instead of 3-chloro-2,4-difluoroaniline to obtain the title compound (35 mg, 15%).
$^1$H-NMR (300 MHz, CDCl$_3$) δ 8.66 (s, 1H), 8.62 (s, 1H), 7.40 (m, 2H), 7.28 (m, 2H), 7.05 (m, 1H), 6.62 (m, 1H), 6.26 (m, 1H), 5.72 (m, 1H), 4.67 (m, 1H), 3.99 (s, 3H), 3.90 (m, 2H), 3.54 (m, 2H), 1.94 (m, 4H).

Example 69

Preparation of 1-(4-(4-(2-chlorophenylamino)-7-methoxyquinazolin-6-yloxy)piperidin-1-yl)pro-2-pen-1-one The procedure of Example 19 was repeated except for using 2-chlorobenzeneamine instead of 3-chloro-2,4-difluoroaniline to obtain the title compound (93 mg, 19%).

¹H-NMR (300 MHz, CDCl₃) δ 8.72 (s, 1H), 7.72 (m, 1H), 7.26 (m, 5H), 6.63 (m, 1H), 6.27 (m, 1H), 5.72 (m, 1H), 4.93 (m, 1H), 3.95 (s, 3H), 3.73 (m, 2H), 3.57 (m, 2H), 1.25 (m, 4H).

Example 70

Preparation of 1-(4-(4-(4-chlorophenylamino)-7-methoxyquinazolin-6-yloxy)piperidin-1-yl)pro-2-pen-1-one The procedure of Example 19 was repeated except for using 4-chlorobenzeneamine instead of 3-chloro-2,4-difluoroaniline to obtain the title compound (40 mg, 27%).

¹H-NMR (300 MHz, CDCl₃) δ 8.65 (s, 1H), 8.00 (s, 1H), 7.67 (d, 2H), 7.36 (s, 1H), 7.33 (d, 2H), 6.61 (m, 1H), 6.23 (m, 1H), 5.68 (m, 1H), 4.64 (m, 1H), 3.97 (s, 3H), 3.76 (m, 2H), 3.65 (m, 2H), 1.70 (m, 4H).

Example 71

Preparation of 1-(4-(4-(3-chloro-2,4-difluorophenylamino)quinazolin-6-yloxy)piperidin-1-yl)pro-2-pen-1-one The procedure of Example 19 was repeated except for using 2-amino-5-methoxybenzoic acid instead of 4,5-dimethoxyanthranilic acid to obtain the title compound (10 mg, 10%).

¹H-NMR (300 MHz, CDCl₃) δ 8.71 (s, 1H), 8.44-8.42 (s, 1H), 7.92 (d, 1H), 7.54-7.50 (m, 1H), 7.21 (m, 1H), 7.11-7.06 (m, 1H), 6.64 (dd, 1H), 5.74 (d, 1H), 4.77 (m, 1H), 3.84-3.63 (m, 4H), 2.04-1.91 (m, 4H).

Example 72

Preparation of 1-(4-(4-(3-chlorobenzylamino)-7-methoxyquinazolin-6-yloxy)piperidin-1-yl)pro-2-pen-1-one The procedure of Example 19 was repeated except for using (3-chlorophenyl)methaneamine instead of 3-chloro-2,4-difluoroaniline to obtain the title compound (8 mg, 29%).

¹H-NMR (300 MHz, CDCl₃) δ 8.58 (s, 1H), 8.40 (s, 1H), 8.16 (m, 1H), 8.01 (s, 1H), 7.59 (m, 2H), 7.29 (s, 1H), 6.59 (m, 1H), 6.28 (m, 1H), 5.68 (m, 2H), 4.62 (m, 1H), 3.95 (s, 3H), 3.86 (m, 2H), 3.67 (m, 2H), 3.50 (m, 2H), 1.83 (m, 4H).

Example 73

Preparation of 1-(4-(7-methoxy-4-(3-vinylphenylamino)quinazolin-6-yloxy)piperidin-1-yl)pro-2-pen-1-one The procedure of Example 19 was repeated except for using 3-vinylbenzeneamine instead of 3-chloro-2,4-difluoroaniline to obtain the title compound (25 mg, 28%).

¹H-NMR (300 MHz, CDCl₃) δ 8.65 (s, 1H), 7.67 (s, 1H), 7.60 (d, 1H), 7.48 (m, 1H) 7.32 (t, 3H), 7.19 (d, 1H), 6.64 (m, 2H), 6.27 (d, 1H), 5.70 (t, 2H), 5.26 (d, 1H), 4.56 (s, 1H), 3.99 (s, 3H), 3.85 (s, 2H), 3.62 (s, 1H), 3.48 (s, 1H).

Example 74

Preparation of 1-(4-(7-methoxy-4-(3-nitrophenylamino)quinazolin-6-yloxy)piperidin-1-yl)pro-2-pen-1-one The procedure of Example 19 was repeated except for using 3-nitrobenzeneamine instead of 3-chloro-2,4-difluoroaniline to obtain the title compound (35 mg, 89%).

¹H-NMR (300 MHz, DMSO-d₆) δ 9.84 (bs, 1H), 8.82 (s, 1H), 8.55 (s, 1H), 8.37 (d, 1H), 8.03 (s, 1H), 7.92 (d, 1H), 7.66 (t, 1H), 7.25 (s, 1H), 6.87-6.78 (m, 1H), 6.13-6.07 (m, 1H), 5.68-5.64 (m, 1H), 4.85-4.82 (m, 1H), 3.94 (s, 3H), 3.88-3.85 (m, 2H), 3.51 (m, 2H), 2.01 (m, 2H), 1.71 (m, 2H).

Example 75

Preparation of N-(3-(6-(1-acryloylpiperidin-4-yloxy)-7-methoxyquinazolin-4-ylamino)phenyl)acrylamide 0.12 g of iron was dissolved in 5 ml of 50% ethanol. 0.01 ml of 35% concentrated hydrochloric acid was added to the solution, and the resulting mixture was heated to 100° C. for activation. 0.2 g of the compound obtained in Example 74 was added thereto, and the resulting mixture was refluxed. After completion of the reaction, the hot reaction solution was filtered through a celite pad under a reduced pressure. The filtrate was distilled under a reduced pressure and dried. The resulting residue was dissolved in 10 ml of 50% tetrahydrofuran, and 75 mg of sodium bicarbonate and 0.05 ml of acryloyl chloride were added to the resulting solution in order, and stirred at room temperature for 30 minutes. After completion of the reaction, saturated sodium bicarbonate was added to the reaction mixture, and the reaction mixture was extracted with chloroform 3 times. The organic layer thus obtained was washed water and saturated sodium bicarbonate, dried over anhydrous sodium sulfate, filtered, and distilled under a reduced pressure. The resulting residue was purified by column chromatography (chloroform:methanol=30:1) to obtain the title compound (10 mg, 21%).

¹H-NMR (300 MHz, CDCl₃) δ 8.62-8.54 (m, 2H), 8.37 (bs, 1H), 7.96 (s, 1H), 7.66 (s, 1H), 7.39 (d, 1H), 7.23-7.18 (m, 3H), 6.61-6.52 (m, 1H), 6.38-6.19 (m, 2H), 5.69-5.65 (m, 2H), 4.61 (s, 1H), 3.91 (s, 3H), 3.80-3.78 (m, 2H), 3.54-3.43 (m, 2H), 2.05-1.85 (m, 4H).

Example 76

Preparation of 1-(4-(4-(3-mercaptophenylamino)-7-methoxyquinazolin-6-yloxy)piperidin-1-yl)pro-2-pen-1-one The procedure of Example 19 was repeated except for using 3-aminobenzenethiol instead of 3-chloro-2,4-difluoroaniline to obtain the title compound (11 mg, 37%).

¹H-NMR (300 MHz, CDCl₃) δ 8.67 (s, 1H), 7.87 (m, 3H), 7.48 (s, 1H), 7.35 (m, 3H) 6.62 (m, 1H), 6.30 (d, 1H), 5.71 (d, 1H), 4.66 (s, 1H), 3.99 (s, 3H), 3.90 (s, 4H), 3.65 (d, 4H).

Example 77

Preparation of 1-(4-(4-(3-(chloromethyl)phenylamino)-7-methoxyquinazolin-6-yloxy)piperidin-1-yl)pro-2-pen-1-one The procedure of Example 19 was repeated except for using 3-(chloromethyl)benzeneamine instead of 3-chloro-2,4-difluoroaniline to obtain the title compound (17 mg, 29%).

¹H-NMR (300 MHz, CDCl₃) δ 8.68 (s, 1H), 7.71 (m, 1H), 7.59 (s, 1H), 7.24 (m, 1H), 7.22 (m, 3H), 6.66 (m, 1H), 6.32 (m, 1H), 5.69 (m, 1H), 4.65 (m, 1H), 4.55 (m, 2H), 3.91 (s, 3H), 3.78 (s, 2H), 3.60 (m, 2H), 1.96 (m, 4H).

Example 78

Preparation of 1-(4-(4-(3-chloro-4-hydroxyphenylamino)-7-methoxyquinazolin-6-yloxy)piperidin-1-yl)pro-2-pen-1-one The procedure of Example 19 was repeated except for using 4-amino-2-chlorophenol instead of 3-chloro-2,4-difluoroaniline to obtain the title compound (109 mg, 28%).
MS (ESI⁺): m/z=455.3 [M+H]⁺.

Example 79

Preparation of 1-(4-(4-(3-fluoro-4-hydroxyphenylamino)-7-methoxyquinazolin-6-yloxy)piperidin-1-yl)prop-2-en-1-one The procedure of Example 19 was repeated except for using 4-amino-2-fluorophenol instead of 3-chloro-2,4-difluoroaniline to obtain the title compound (373 mg, 67%).
MS (ESI⁺): m/z=439.2 [M+H]⁺.

Example 80

Preparation of 1-(4-(4-(3-chloro-2,4-difluorophenylamino)-7-methoxyquinazolin-6-yloxy)piperidin-1-yl)but-2-yn-1-one The procedure of Example 19 was repeated except for using but-2-inoyl chloride instead of acryloyl chloride to obtain the title compound (38 mg, 33%).
¹H-NMR (300 MHz, CDCl₃) δ 8.34 (s, 1H), 7.78 (s, 1H), 7.52 (m, 1H), 7.17 (m, 2H), 4.80 (m, 1H), 4.03 (m, 1H), 3.99 (s, 3H), 3.83 (m, 2H), 3.64 (m, 1H), 2.02 (s, 3H), 2.00 (m, 4H);
MS (ESI⁺): m/z=487.3 [M+H]⁺.

Example 81

Preparation of 1-(4-(4-(3-chloro-2,4-difluorophenylamino)-7-methoxyquinazolin-6-yloxy)piperidin-1-yl)-3-methylbut-2-en-1-one The procedure of Example 19 was repeated except for using 2-methylacryloyl chloride instead of acryloyl chloride to obtain the title compound (86 mg, 36%).
¹H-NMR (300 MHz, CDCl₃) δ 8.67 (s, 1H), 8.08 (s, 1H), 7.55 (m, 1H), 7.31 (s, 1H), 7.24 (m, 1H), 5.90 (m, 1H), 4.94 (m, 1H), 4.08 (s, 3H), 3.92 (m, 2H), 3.58 (m, 2H), 2.09 (m, 2H), 1.85 (s, 3H), 1.84 (m, 2H), 1.73 (s, 3H);
MS (ESI⁺): m/z=503.3 [M+H]⁺.

Example 82

Preparation of (E)-4-(4-(4-(3-chloro-2,4-difluorophenylamino)-7-methoxyquinazolin-6-yloxy)piperidin-1-yl)-N-methyl-4-oxobut-2-enamide The procedure of Example 19 was repeated except for using (E)-4-(methylamino)-4-oxobut-2-enoyl chloride instead of acryloyl chloride to obtain the title compound (60 mg, 24%).

¹H-NMR (300 MHz, CDCl₃) δ 8.65 (s, 1H), 8.19 (m, 1H), 7.54 (s, 1H), 7.31 (s, 1H), 7.30 (s, 1H), 7.07 (m, 1H), 6.39 (d, 1H), 6.09 (d, 1H), 4.70 (m, 1H), 4.00 (s, 3H), 3.79 (m, 3H), 3.50 (m, 1H), 2.85 (d, 3H);
MS (ESI⁺): m/z=532.3 [M+H]⁺.

Example 83

Preparation of (Z)-methyl 4-(4-(4-(3-chloro-2,4-difluorophenylamino)-7-methoxyquinazolin-6-yloxy)piperidin-1-yl)-4-oxobut-2-enoate The procedure of Example 19 was repeated except for using (Z)-methyl-4-chloro-4-oxobut-2-enoate instead of acryloyl chloride to obtain the title compound (23 mg, 9%).
¹H-NMR (300 MHz, CDCl₃) δ 8.66 (s, 1H), 8.24 (m, 1H), 7.40 (bs, 1H), 7.30 (m, 2H), 7.06 (m, 1H), 6.58 (d, 1H), 6.03 (d, 1H), 4.71 (m, 1H), 4.01 (s, 3H), 3.90 (m, 1H), 3.83 (m, 1H), 3.75 (s, 3H), 3.70 (m, 1H), 3.44 (m, 1H), 2.02 (m, 4H);
MS (ESI⁺): m/z=533.3 [M+H]⁺.

Example 84

Preparation of (Z)-methyl 4-(4-(4-(3,4-dichloro-2-fluorophenylamino)-7-methoxyquinazolin-6-yloxy)piperidin-1-yl)-4-oxobut-2-enoate The procedure of Example 19 was repeated except for using 3,4-dichloro-2-fluoroaniline instead of 3-chloro-2,4-difluoroaniline to obtain the title compound (9 mg, 7%).
¹H-NMR (300 MHz, CDCl₃) δ 8.70 (s, 1H), 8.44 (t, 1H), 7.42 (m, 2H), 7.23 (s, 1H), 6.58 (d, 1H), 6.04 (d, 1H), 4.73 (bm, 1H), 4.01 (s, 3H), 3.89 (m, 2H), 3.76 (s, 3H), 3.71 (m, 1H), 3.43 (m, 1H), 2.01 (m, 4H);
MS (ESI⁺): m/z=549.3 [M+H]⁺.

Example 85

Preparation of (Z)-4-(4-(4-(3-chloro-2,4-difluorophenylamino)-7-methoxyquinazolin-6-yloxy)piperidin-1-yl)-4-oxobut-2-enoic acid 0.1 g of the compound obtained in Example 83 was diluted in 2 ml of tetrahydrofuran, and 0.1 ml of a 3M lithium hydroxide solution was added thereto at 0° C. The resulting mixture was stirred at room temperature for two hours and extracted with chloroform. The aqueous layer was acidified with a 1N HCl and extracted three times with chloroform. The organic layer was dried over anhydrous sodium sulfate, filtered and distilled under a reduced pressure. The resulting residue was purified by column chromatography (methylene chloride: methanol=5:1) to obtain the title compound (118 mg, 48%).
¹H-NMR (300 MHz, CDCl₃) δ 8.48 (s, 1H), 7.80 (m, 2H), 7.22 (s, 1H), 7.09 (t, 1H), 6.33 (d, 1H), 6.10 (d, 1H), 4.99 (m, 1H), 4.00 (s, 3H), 3.70 (m, 4H), 1.90 (m, 4H);
MS (ESI⁺): m/z=519.2 [M+H]⁺.

Example 86

Preparation of (Z)-4-(4-(4-(3,4-dichloro-2-fluorophenylamino)-7-methoxyquinazolin-6-yloxy)piperidin-1-yl)-4-oxobut-2-enoic acid The procedure of Example 85 was repeated except for using 3,4-dichloro-2-fluoroaniline instead of 3-chloro-2,4-difluoroaniline to obtain the title compound (100 mg, 41%).

¹H-NMR (300 MHz, CDCl₃) δ 8.48 (s, 1H), 7.68 (t, 1H), 7.21 (m, 1H), 7.20 (s, 1H), 6.33 (d, 1H), 5.01 (d, 1H), 4.69 (bm, 1H), 3.95 (s, 3H), 3.66 (m, 3H), 3.35 (m, 1H), 1.87 (m, 4H);
MS (ESI⁺): m/z=535.2 [M+H]⁺.

Example 87

Preparation of (E)-4-(4-(4-(3,4-dichloro-2-fluorophenylamino)-7-methoxyquinazolin-6-yloxy)piperidin-1-yl)-4-oxobut-2-enoic acid The procedure of Example 86 was repeated except for using (E)-methyl-4-chloro-4-oxobut-2-enoate instead of (Z)-methyl-4-chloro-4-oxobut-2-enoate to obtain the title compound (10 mg, 20%).
¹H-NMR (300 MHz, CDCl₃) δ 8.49 (s, 1H), 7.74 (t, 1H), 7.56 (s, 1H), 7.31 (m, 2H), 7.23 (s, 1H), 6.65 (d, 1H), 4.68 (bm, 1H), 3.95 (s, 3H), 3.79 (m, 2H), 3.66 (m, 1H), 3.49 (m, 1H), 1.90 (m, 4H);
MS (ESI⁺): m/z=535.2 [M+H]⁺.

Example 88

Preparation of (E)-4-(4-(4-(3-chloro-2,4-difluorophenylamino)-7-methoxyquinazolin-6-yloxy)piperidin-1-yl)-N-hydroxy-4-oxobut-2-enamide 0.1 g of (E)-4-(4-(4-(3-chloro-2,4-difluorophenylamino)-7-methoxyquinazolin-6-yloxy)piperidin-1-yl)-4-oxobut-2-enoic acid obtained by repeating the procedure of Example 87 except for using 3-chloro-2,4-difluoroaniline instead of 3,4-dichloro-2-fluoroaniline was diluted with 1 ml of tetrahydrofuran, and 0.03 ml of N-methylmorpholine and 0.03 ml of isobutyl chloroformate were added thereto at −15° C. The resulting mixture was stirred for 30 minutes, and 0.03 ml of hydroxylamine was added thereto. The resulting solution was heated to room temperature and incubated for two hours. After the reaction terminated, water was added, and the resulting solution was extracted three times with ethyl acetate. The organic layer was dried over anhydrous sodium sulfate, filtered and distilled under a reduced pressure. The resulting residue was purified by column chromatography (ethyl acetate:methylene chloride:methanol=7:7:1) to obtain the title compound (30 mg, 30%).
¹H-NMR (300 MHz, CDCl₃) δ 8.33 (s, 1H), 7.80 (s, 1H), 7.49 (m, 1H), 7.44 (d, 1H), 7.22 (s, 1H), 7.19 (m, 1H), 6.77 (d, 1H), 4.00 (s, 3H), 3.94 (m, 1H), 3.70 (m, 2H), 3.06 (m, 2H), 2.08 (m, 2H), 1.89 (m, 2H);
MS (ESI⁺): m/z=534.2 [M+H]⁺.

Example 89

Preparation of (Z)-3-chloro-1-(4-(4-(3,4-dichloro-2-fluorophenylamino)-7-methoxyquinazolin-6-yloxy)piperidin-1-yl)prop-2-en-1-one The procedure of Example 19 was repeated except for using (Z)-3-chloroacryloyl chloride instead of acryloyl chloride to obtain the title compound (5 mg, 8%).
¹H-NMR (300 MHz, CDCl₃) δ 8.71 (s, 1H), 8.40 (t, 1H), 7.51 (bs, 1H), 7.33 (m, 3H), 6.42 (d, 1H), 6.36 (d, 1H), 4.73 (bm, 1H), 4.03 (s, 3H), 3.93 (m, 1H), 3.81 (m, 2H), 3.53 (m, 1H), 2.03 (m, 4H);
MS (ESI⁺): m/z=525.1 [M+H]⁺.

Example 90

Preparation of (E)-3-chloro-1-(4-(4-(3,4-dichloro-2-fluorophenylamino)-7-methoxyquinazolin-6-yloxy)piperidin-1-yl)prop-2-en-1-one The procedure of Example 19 was repeated except for using (E)-3-chloroacryloyl chloride instead of acryloyl chloride to obtain the title compound (8 mg, 13%).
¹H-NMR (300 MHz, CDCl₃) δ 8.70 (s, 1H), 8.46 (t, 1H), 7.34 (m, 4H), 7.23 (s, 1H), 6.74 (d, 1H), 4.72 (bm, 1H), 4.01 (s, 3H), 3.82 (m, 3H), 3.55 (m, 1H), 1.99 (m, 4H);
MS (ESI⁺): m/z=525.1 [M+H]⁺.

Example 91

Preparation of N-(3-(4-(4-(3,4-dichloro-2-fluorophenylamino)-7-methoxyquinazolin-6-yloxy)piperidin-1-yl)-3-oxoprop-1-en-2-yl)acetamide The procedure of Example 19 was repeated except for using 2-acetamidoacryloyl chloride instead of acryloyl chloride to obtain the title compound (7 mg, 3%).
¹H-NMR (300 MHz, CDCl₃) δ 8.66 (s, 1H), 8.22 (m, 1H), 7.80 (s, 1H), 7.33 (m, 3H), 5.66 (s, 1H), 4.84 (s, 1H), 4.69 (bm, 1H), 4.00 (s, 3H), 3.90 (m, 2H), 3.69 (m, 2H), 2.07 (s, 3H), 1.97 (m, 4H);
MS (ESI⁺): m/z=548.3 [M+H]⁺.

Example 92

Preparation of (E)-1-((3S)-3-(4-(3-chloro-2,4-difluorophenylamino)-7-methoxyquinazolin-6-yloxy)pyrrolidin-1-yl)-4-(dimethylamino)but-2-en-1-one Step 1) (E)-4-bromo-1-((3S)-3-(4-(3-chloro-2,4-difluorophenylamino)-7-methoxyquinazolin-6-yloxy)pyrrolidin-1-yl)but-2-en-1-one The procedure of Example 1 was repeated except for using (E)-4-bromobut-2-enoyl chloride instead of acryloyl chloride in step 7) to obtain the title compound (75 mg, 58%).
¹H-NMR (300 MHz, CDCl₃) δ 8.63 (s, 1H), 8.09 (m, 1H), 7.53 (s, 1H), 7.38 (s, 1H), 7.18 (s, 1H), 6.91 (m, 2H), 5.20 (bm, 1H), 4.08 (m, 2H), 3.92 (s, 3H), 3.72 (m, 4H), 2.28 (m, 2H).

Step 2) (E)-1-((3S)-3-(4-(3-chloro-2,4-difluorophenylamino)-7-methoxyquinazolin-6-yloxy)pyrrolidin-1-yl)-4-(dimethylamino)but-2-en-1-one 580 mg of the compound obtained in step 1) was dissolved in 10 ml of tetrahydrofuran at 0° C., and 5 ml of a 1.0 M dimethylamine-containing tetrahydrofuran solution was added thereto. The resulting mixture was stirred at room temperature for one hour, a saturated sodium bicarbonate was added thereto, and the resulting solution was extracted with chloroform. The organic layer was dried over anhydrous sodium sulfate, filtered and distilled under a reduced pressure. The resulting residue was purified by column chromatography (chloroform:methanol=30:1) to obtain the title compound (175 mg, 32%).
¹H-NMR (300 MHz, CDCl₃) δ 8.56 (s, 1H), 7.84 (m, 1H), 7.40 (s, 1H), 7.17 (s, 1H), 7.01 (t, 1H), 6.85 (m, 1H), 6.24 (m, 1H), 5.12 (bm, 1H), 4.03 (m, 1H), 3.95 (s, 3H), 3.75 (m, 4H), 3.03 (m, 2H), 2.32 (m, 2H), 2.22 (s, 6H);
MS (ESI⁺): m/z=518.3 [M+H]⁺.

Example 93

Preparation of (E)-1-((3S)-3-(4-(3-chloro-2,4-difluorophenylamino)-7-methoxyquinazolin-6-yloxy)pyrrolidin-1-yl)-4-(diethylamino)but-2-en-1-one The procedure of Example 92 was repeated except for using diethylamine instead of a 1.0 M dimethylamine-containing tetrahydrofuran solution to obtain the title compound (4 mg, 16%).

$^1$H-NMR (300 MHz, CDCl$_3$) δ 8.60 (s, 1H), 8.02 (m, 1H), 7.30 (s, 1H), 7.22 (s, 1H), 7.05 (t, 1H), 6.93 (m, 1H), 6.29 (m, 1H), 5.11 (bm, 1H), 4.03 (s, 1H), 3.98 (s, 3H), 3.82 (m, 4H), 3.23 (d, 2H), 2.52 (q, 4H), 1.01 (m, 6H);

MS (ESI$^+$): m/z=546.2 [M+H]$^+$.

Example 94

Preparation of (E)-1-((3S)-3-(4-(3-chloro-2,4-difluorophenylamino)-7-methoxyquinazolin-6-yloxy)pyrrolidin-1-yl)-4-morpholinobut-2-en-1-one The procedure of Example 92 was repeated except for using morpholine instead of a 1.0M dimethylamine-containing tetrahydrofuran solution to obtain the title compound (8 mg, 26%).

$^1$H-NMR (300 MHz, CDCl$_3$) δ 8.61 (s, 1H), 8.05 (m, 1H), 7.31 (s, 1H), 7.22 (s, 1H), 7.06 (t, 1H), 6.91 (m, 1H), 6.29 (m, 1H), 5.12 (bm, 1H), 4.06 (s, 1H), 3.97 (s, 3H), 3.84 (m, 4H), 3.70 (m, 4H), 3.10 (d, 2H), 2.44 (m, 4H), 2.26 (m, 2H);

MS (ESI$^+$): m/z=560.2 [M+H]$^+$.

Example 95

Preparation of (E)-1-((3S)-3-(4-(3-chloro-2,4-difluorophenylamino)-7-methoxyquinazolin-6-yloxy)pyrrolidin-1-yl)-4-(pyrrolidin-1-yl)but-2-en-1-one The procedure of Example 92 was repeated except for using pyrrolidin instead of a 1.0M dimethylamine-containing tetrahydrofuran solution to obtain the title compound (5 mg, 18%).

$^1$H-NMR (300 MHz, CDCl$_3$) δ 8.61 (s, 1H), 8.02 (m, 1H), 7.28 (s, 1H), 7.22 (s, 1H), 7.05 (t, 1H), 6.95 (m, 1H), 6.27 (m, 1H), 5.11 (bm, 1H), 4.04 (s, 1H), 3.98 (s, 3H), 3.87 (m, 4H), 3.23 (d, 2H), 2.50 (m, 4H), 2.27 (m, 2H), 1.78 (m, 4H);

MS (ESI$^+$): m/z=544.2 [M+H]$^+$.

Example 96

Preparation of (E)-1-((3S)-3-(4-(3-chloro-2-fluorophenylamino)-7-methoxyquinazolin-6-yloxy)pyrrolidin-1-yl)-4-(dimethylamino)but-2-en-1-one The procedure of Example 92 was repeated except for using 3-chloro-2-fluoroaniline instead of 3-chloro-2,4-difluoroaniline to obtain the title compound (2 mg, 5%).

$^1$H-NMR (300 MHz, CDCl$_3$) δ 8.70 (s, 1H), 8.38 (m, 1H), 7.31 (s, 1H), 7.18 (m, 2H), 6.97 (m, 1H), 6.95 (m, 1H), 6.33 (m, 1H), 5.07 (bm, 1H), 4.00 (s, 3H), 3.82 (m, 4H), 3.13 (m, 2H), 2.32 (m, 2H), 2.29 (s, 6H);

MS (ESI$^+$): m/z=500.35 [M+H]$^+$.

Example 97

Preparation of (E)-1-((3S)-3-(4-(3-chloro-2,4-difluorophenylamino)quinazolin-6-yloxy)pyrrolidin-1-yl)-4-(dimethylamino)but-2-en-1-one The procedure of Example 92 was repeated except for using 2-amino-5-methoxybenzoic acid instead of 4,5-dimethoxyanthranilic acid to obtain the title compound (26 mg, 39%).

$^1$H-NMR (300 MHz, CDCl$_3$) δ 8.59 (s, 1H), 7.88 (m, 1H), 7.80 (m, 1H), 7.57 (m, 1H), 7.39 (m, 1H), 7.02 (m, 1H), 6.85 (m, 1H), 6.26 (m, 1H), 5.08 (bm, 1H), 3.85 (m, 4H), 3.00 (d, 2H), 2.43 (m, 2H), 2.21 (s, 6H);

MS (ESI$^+$): m/z=488.2 [M+H]$^+$.

Example 98

Preparation of (E)-1-(4-(4-(3-chloro-2,4-difluorophenylamino)-7-methoxyquinazolin-6-yloxy)piperidin-1-yl)-4-(dimethylamino)but-2-en-1-one The procedure of Example 92 was repeated except for using N-Boc-4-hydroxypiperidine instead of (R)-(−)-N-Boc-3-pyrrolidinol to obtain the title compound (50 mg, 16%).

$^1$H-NMR (300 MHz, CDCl$_3$) δ 8.66 (s, 1H), 8.28 (m, 1H), 7.31 (m, 2H), 7.06 (m, 1H), 6.85 (m, 1H), 6.50 (m, 1H), 4.71 (bm, 1H), 4.02 (s, 3H), 3.89 (m, 2H), 3.71 (m, 1H), 3.60 (m, 1H), 3.12 (d, 2H), 2.30 (s, 6H), 2.00 (m, 4H);

MS (ESI$^+$): m/z=532.2 [M+H]$^+$.

Example 99

Preparation of (E)-1-(4-(4-(3,4-dichloro-2-fluorophenylamino)-7-methoxyquinazolin-6-yloxy)piperidin-1-yl)-4-(dimethylamino)but-2-en-1-one The procedure of Example 98 was repeated except for using 3,4-dichloro-2-fluoroaniline instead of 3-chloro-2,4-difluoroaniline to obtain the title compound (20 mg, 16%).

$^1$H-NMR (300 MHz, CDCl$_3$) δ 8.65 (s, 1H), 8.22 (t, 1H), 7.45 (s, 1H), 7.30 (d, 1H), 7.29 (s, 1H), 6.83 (m, 1H), 6.54 (d, 1H), 4.71 (bm, 1H), 3.99 (s, 3H), 3.85 (m, 2H), 3.50 (m, 2H), 3.16 (d, 2H), 2.33 (s, 6H), 1.98 (m, 4H);

MS (ESI$^+$): m/z=548.2 [M+H]$^+$.

Example 100

Preparation of (E)-1-(4-(4-(3-chloro-2-fluorophenylamino)-7-methoxyquinazolin-6-yloxy)piperidin-1-yl)-4-(dimethylamino)but-2-en-1-one The procedure of Example 98 was repeated except for using 3-chloro-2-fluoroaniline instead of 3-chloro-2,4-difluoroaniline to obtain the title compound (50 mg, 27%).

$^1$H-NMR (300 MHz, CDCl$_3$) δ 8.63 (s, 1H), 8.09 (t, 1H), 7.51 (s, 1H), 7.27 (s, 1H), 7.13 (m, 2H), 6.79 (m, 1H), 6.44 (d, 1H), 4.66 (bm, 1H), 3.96 (s, 3H), 3.84 (m, 2H), 3.50 (m, 2H), 3.05 (m, 2H), 2.24 (s, 6H), 1.93 (m, 4H);

MS (ESI$^+$): m/z=514.2 [M+H]$^+$.

Example 101

Preparation of (E)-1-(3-(4-(3-chloro-2,4-difluorophenylamino)-7-methoxyquinazolin-6-yloxy)azetidin-1-yl)-4-(dimethylamino)but-2-en-1-one The procedure of Example 92 was repeated except for using N-Boc-3-hydroxyazetidine instead of (R)-(−)-N-Boc-3-pyrrolidinol to obtain the title compound (60 mg, 47%).

$^1$H-NMR (300 MHz, CD$_3$OD) δ 8.33 (s, 1H), 7.53 (m, 1H), 7.37 (s, 1H), 7.17 (m, 2H), 6.79 (m, 1H), 6.20 (m, 1H), 5.18 (bm, 1H), 4.79 (m, 1H), 4.56 (m, 1H), 4.42 (m, 1H), 4.14 (m, 1H), 3.99 (s, 3H), 3.12 (m, 2H), 2.45 (s, 6H);

MS (ESI$^+$): m/z=504.3 [M+H]$^+$.

Example 102

Preparation of (E)-1-(3-(4-(3-chloro-2-fluorophenylamino)-7-methoxyquinazolin-6-yloxy)azetidin-1-yl)-4-(dimethylamino)but-2-en-1-one The procedure of Example 101 was repeated except for using 3-chloro-2-fluoroaniline instead of 3-chloro-2,4-difluoroaniline to obtain the title compound (20 mg, 21%).

$^1$H-NMR (300 MHz, CD$_3$OD) δ 8.36 (s, 1H), 7.54 (t, 1H), 7.44 (s, 1H), 7.37 (m, 1H), 7.20 (m, 2H), 6.80 (m, 1H), 6.23 (m, 1H), 5.22 (bm, 1H), 4.82 (m, 1H), 4.55 (m, 1H), 4.40 (m, 1H), 4.15 (m, 1H), 4.01 (s, 3H), 3.20 (m, 2H), 2.31 (s, 6H);

MS (ESI$^+$): m/z=486.3 [M+H]$^+$.

Example 103

Preparation of (E)-N-(2-(4-(3-chloro-2,4-difluorophenylamino)-7-methoxyquinazolin-6-yloxy)ethyl)-4-(dimethylamino)but-2-enamide The procedure of Example 92 was repeated except for using tent-butyl 2-hydroxyethylcarbamate instead of (R)-(−)-N-Boc-3-pyrrolidinol to obtain the title compound (46 mg, 34%).

$^1$H-NMR (300 MHz, CDCl$_3$) δ 8.73 (s, 1H), 7.99 (s, 1H), 7.26 (s, 1H), 7.19 (s, 1H), 7.01 (m, 1H), 6.81 (m, 1H), 6.68 (m, 1H), 6.03 (d, 1H), 4.25 (s, 2H), 3.96 (s, 3H), 3.75 (s, 2H), 2.93 (s, 2H), 2.25 (s, 6H).

Example 104

Preparation of 1-(3-(4-(3-chloro-2,4-difluorophenylamino)-7-methoxyquinazolin-6-yloxy)azetidin-1-yl)-2-((dimethylamino)methyl)prop-2-en-1-one Step 1) 2-((dimethylamino)methyl)acrylic acid 1 g of malonic acid and 0.63 g of paraformaldehyde were diluted with 10 ml of 1,3-dioxane, and 4.8 ml of a 2.0M dimethylamine-containing tetrahydrofuran solution was added thereto. The resulting mixture was heated to 70° C. and stirred for one hour. After the reaction terminated, the resulting solution was distilled under a reduced pressure. The resulting residue was crystallized with acetone and filtered under a reduced pressure to obtain the title compound (0.4 g, 32%) in the form of white crystal.

$^1$H-NMR (300 MHz, D$_2$O) δ 6.62 (s, 1H), 6.11 (s, 1H), 4.16 (s, 2H), 2.88 (s, 6H);

MS (ESI$^+$): m/z=130.0 [M+H]$^+$.

Step 2) 1-(3-(4-(3-chloro-2,4-difluorophenylamino)-7-methoxyquinazolin-6-yloxy)azetidin-1-yl)-2-((dimethylamino)methyl)prop-2-en-1-one 50 mg of 6-(azetidin-3-yloxy)-N-(3-chloro-2,4-difluorophenyl)-7-methoxyquinazolin-4-amine obtained by repeating the procedure of step 6) of Example 1 except for using N-Boc-3-hydroxyazetidine instead of (R)-(−)-N-Boc-3-pyrrolidinol was diluted with 2 ml of tetrahydrofuran, and 25 mg of the compound obtained in step 1), 37 mg of N-(3-dimethylaminopropyl)-N'-ethylcarbodiimide hydrochloride, and 5 µl of pyridine were added thereto. The resulting mixture was incubated at room temperature for two hours. After the reaction terminated, water was added, and the resulting solution was extracted with chloroform. The organic layer was dried over anhydrous sodium sulfate, filtered and distilled under a reduced pressure. The resulting residue was purified by column chromatography (chloroform:methanol=15:1) to obtain the title compound (2 mg, 3%).

$^1$H-NMR (300 MHz, CDCl$_3$) δ 9.38 (s, 1H), 8.54 (s, 1H), 8.14 (s, 1H), 7.54 (m, 1H), 6.99 (m, 1H), 6.04 (bm, 1H), 5.96 (s, 1H), 5.49 (s, 1H), 4.91 (m, 2H), 4.03 (s, 3H), 3.96 (m, 2H), 3.84 (s, 2H);

MS (ESI$^+$): m/z=504.3 [M+H]$^+$.

Example 105

Preparation of 1-(3-(4-(3-chloro-2,4-difluorophenylamino)-7-methoxyquinazolin-6-yloxy)azetidin-1-yl)-2-(morpholinomethyl)prop-2-en-1-one The procedure of Example 104 was repeated except for using morpholine instead of a 2.0M dimethylamine-containing tetrahydrofuran solution in step 1) to obtain the title compound (4 mg, 6%).

$^1$H-NMR (300 MHz, CDCl$_3$) δ 8.64 (s, 1H), 8.04 (m, 1H), 7.79 (s, 1H), 7.31 (s, 1H), 7.07 (s, 1H), 7.04 (m, 1H), 5.56 (s, 1H), 5.51 (s, 1H), 5.18 (m, 1H), 4.65 (m, 2H), 4.50 (m, 1H), 4.25 (m, 1H), 4.03 (s, 3H), 3.69 (m, 4H), 3.25 (m, 1H), 3.11 (m, 1H), 2.45 (m, 4H);

MS (ESI$^+$): m/z=546.3 [M+H]$^+$.

Example 106

Preparation of 1-(3-(4-(3-chloro-2,4-difluorophenylamino)-7-methoxyquinazolin-6-yloxy)azetidin-1-yl)-2-((4-methylpiperazin-1-yl)methyl)prop-2-en-1-one The procedure of Example 104 was repeated except for using 1-methyl piperazine instead of a 2.0M dimethylamine-containing tetrahydrofuran solution in step 1) to obtain the title compound (7 mg, 3%).

$^1$H-NMR (300 MHz, CDCl$_3$) δ 8.61 (s, 1H), 8.43 (s, 1H), 7.84 (m, 1H), 7.30 (s, 1H), 7.27 (s, 1H), 7.02 (m, 1H), 5.53 (s, 1H), 5.49 (s, 1H), 5.23 (m, 1H), 4.70 (m, 2H), 4.23 (m, 1H), 4.16 (m, 1H), 4.04 (s, 3H), 3.42 (m, 1H), 3.00 (m, 1H), 2.43 (m, 8H), 2.27 (s, 3H);

MS (ESI$^+$): m/z=559.3 [M+H]$^+$.

Example 107

Preparation of 1-(3-(4-(3-chloro-2-fluorophenylamino)-7-methoxyquinazolin-6-yloxy)azetidin-1-yl)-2-(piperidin-1-ylmethyl)prop-2-en-1-one The procedure of Example 104 was repeated except for using piperidine instead of a 2.0M dimethylamine-containing tetrahydrofuran solution in step 1) and 3-chloro-2-fluoroaniline instead of 3-chloro-2,4-difluoroaniline in step 2) to obtain the title compound (35 mg, 25%).

¹H-NMR (300 MHz, CDCl₃) δ 8.64 (s, 1H), 8.54 (bs, 1H), 7.87 (m, 1H), 7.29 (s, 1H), 7.27 (s, 1H), 7.18 (m, 1H), 7.09 (m, 1H), 5.46 (s, 1H), 5.42 (s, 1H), 5.23 (m, 1H), 4.88 (m, 1H), 4.60 (m, 1H), 4.53 (m, 1H), 4.19 (m, 1H), 4.03 (s, 3H), 3.29 (m, 1H), 2.85 (m, 1H), 2.30 (m, 4H), 1.51 (m, 4H), 1.40 (m, 2H);

MS (ESI⁺): m/z=526.3 [M+H]⁺.

Example 108

Preparation of 1-(3-(4-(3-chloro-2,4-difluorophenylamino)-7-methoxyquinazolin-6-yloxy)azetidin-1-yl)-2-(piperidin-1-ylmethyl)prop-2-en-1-one The procedure of Example 104 was repeated except for using piperidine instead of a 2.0M dimethylamine-containing tetrahydrofuran solution in step 1) to obtain the title compound (4 mg, 3%).

¹H-NMR (300 MHz, CDCl₃) δ 8.56 (s, 1H), 7.68 (m, 1H), 7.20 (m, 2H), 6.93 (m, 1H), 5.36 (s, 1H), 5.32 (s, 1H), 5.17 (m, 1H), 4.67 (m, 1H), 4.58 (m, 1H), 4.48 (m, 1H), 4.07 (m, 1H), 3.94 (s, 3H), 3.31 (m, 1H), 2.70 (m, 1H), 2.20 (m, 4H), 1.45 (m, 4H), 1.34 (m, 2H);

MS (ESI⁺): m/z=544.3 [M+H]⁺.

Example 109

Preparation of 1-(4-(4-(3-chloro-2,4-difluorophenylamino)-7-methoxyquinazolin-6-yloxy)piperidin-1-yl)-2-((dimethylamino)methyl)prop-2-en-1-one The procedure of Example 104 was repeated except for using N-Boc-4-hydroxypiperidine instead of N-Boc-3-hydroxyazetidine in step 2) to obtain the title compound (6 mg, 3%).

¹H-NMR (300 MHz, CDCl₃) δ 8.54 (s, 1H), 7.87 (m, 1H), 7.46 (s, 1H), 7.24 (s, 1H), 7.04 (m, 1H), 5.51 (s, 1H), 5.34 (s, 1H), 4.74 (m, 1H), 3.99 (s, 3H), 3.88 (m, 2H), 3.62 (m, 2H), 3.33 (s, 2H), 2.41 (s, 6H), 1.91 (m, 4H);

MS (ESI⁺): m/z=532.3 [M+H]⁺.

Example 110

Preparation of 1-(4-(4-(3-chloro-2,4-difluorophenylamino)-7-methoxyquinazolin-6-yloxy)piperidin-1-yl)-2-(morpholinomethyl)prop-2-en-1-one The procedure of Example 104 was repeated except for using morpholine instead of a 2.0M dimethylamine-containing tetrahydrofuran solution in step 1) and N-Boc-4-hydroxypiperidine instead of N-Boc-3-hydroxyazetidine in step 2) to obtain the title compound (180 mg, 33%).

¹H-NMR (300 MHz, CDCl₃) δ 8.62 (s, 1H), 8.10 (m, 1H), 7.40 (s, 1H), 7.29 (s, 1H), 7.04 (m, 1H), 5.39 (s, 1H), 5.22 (s, 1H), 4.71 (m, 1H), 3.99 (s, 3H), 3.89 (m, 2H), 3.68 (m, 4H), 3.59 (m, 2H), 3.22 (s, 2H), 2.51 (m, 4H), 1.93 (m, 4H);

MS (ESI⁺): m/z=574.3 [M+H]⁺.

Example 111

Preparation of 1-(4-(4-(3,4-dichloro-2-fluorophenylamino)-7-methoxyquinazolin-6-yloxy)piperidin-1-yl)-2-((dimethylamino)methyl)prop-2-en-1-one The procedure of Example 104 was repeated except for using N-Boc-4-hydroxypiperidine instead of N-Boc-3-hydroxyazetidine and 3,4-dichloro-2-fluoroaniline instead of 3-chloro-2,4-difluoroaniline in step 2) to obtain the title compound (10 mg, 4%).

¹H-NMR (300 MHz, CDCl₃) δ 8.72 (s, 1H), 8.47 (m, 1H), 7.36 (s, 3H), 7.25 (s, 1H), 5.40 (s, 1H), 5.24 (s, 1H), 4.74 (m, 1H), 4.04 (s, 3H), 3.95 (m, 2H), 3.64 (m, 2H), 3.17 (s, 2H), 2.29 (s, 6H), 2.01 (m, 4H);

MS (ESI⁺): m/z=548.3 [M+H]⁺.

Example 112

Preparation of (Z)-1-(3-(4-(3-chloro-2,4-difluorophenylamino)-7-methoxyquinazolin-6-yloxy)azetidin-1-yl)-4-(dimethylamino)but-2-en-1-one Step 1) 4-(dimethylamino)but-2-inoic acid 3.0 ml of 3-dimethylamino-1-propyne was diluted with 30 ml of tetrahydrofuran, and 27 ml of a 1.6M n-butyl lithium-containing tetrahydrofuran solution was gradually dropwise added thereto at −78° C. The resulting mixture was stirred at −78° C. for 30 minutes and heated to room temperature while bubbling with CO₂ gas for one hour. After the reaction terminated, the resulting solution was acidified to pH 3-4 with a 35% HCl, distilled under a reduced pressure and dried in vacuum. The resulting residue was dissolved in hot ethanol, and the resulting solution was stirred at 0° C. The resulting solid was filtered under a reduced pressure to obtain the title compound (2 g, 56%) in a crystal form.

¹H-NMR (300 MHz, D₂O) δ 4.07 (s, 2H), 2.89 (s, 6H).

Step 2) (Z)-4-(dimethylamino)but-2-enoic acid 2 g of the compound obtained in step 1) was diluted with 120 ml of a mixed solvent of ethyl acetate and methanol (1:1), and 450 mg of calcium carbonate on palladium was added thereto. The resulting mixture was stirred under a hydrogen gas for two hours. After the reaction terminated, the resulting solution was filtered through a cellite pad and distilled under a reduced pressure. The resulting residue was purified by column chromatography (methylene chloride:methanol=2:1) to obtain the title compound (800 mg, 39%).

¹H-NMR (300 MHz, CDCl₃) δ 6.23 (d, 1H), 5.97 (m, 1H), 3.56 (d, 2H), 2.67 (s, 6H).

Step 3) (Z)-1-(3-(4-(3-chloro-2,4-difluorophenylamino)-7-methoxyquinazolin-6-yloxy)azetidin-1-yl)-4-(dimethylamino)but-2-en-1-one The procedure of step 2) of Example 104 was repeated except for using the compound obtained in step 2) instead of 2-((dimethylamino)methyl)acrylic acid to obtain the title compound (80 mg, 31%).

¹H-NMR (300 MHz, CDCl₃) δ 8.68 (s, 1H), 8.29 (m, 1H), 7.33 (s, 1H), 7.07 (m, 1H), 6.89 (s, 1H), 6.22 (m, 1H), 5.85 (s, 1H), 5.15 (m, 1H), 4.56 (m, 2H), 4.41 (m, 1H), 4.26 (m, 1H), 4.04 (s, 3H), 3.57 (d, 2H), 2.28 (s, 6H);

MS (ESI⁺): m/z=504.2 [M+H]⁺.

Example 113

Preparation of (Z)-1-(4-(4-(3-chloro-2,4-difluorophenylamino)-7-methoxyquinazolin-6-yloxy)piperidin-1-yl)-4-(dimethylamino)but-2-en-1-one The procedure of Example 112 was repeated except for using N-Boc-4-hydroxypiperidine instead of N-Boc-3-hydroxyazetidine in step 3) to obtain the title compound (8 mg, 44%).

¹H-NMR (300 MHz, CDCl₃) δ 8.54 (s, 1H), 7.82 (m, 1H), 7.55 (s, 1H), 7.32 (s, 1H), 7.06 (m, 1H), 6.25 (d, 1H), 6.08 (m, 1H), 4.72 (m, 1H), 4.01 (s, 3H), 3.88 (m, 2H), 3.65 (m, 1H), 3.49 (m, 1H), 3.40 (d, 2H), 2.37 (s, 6H), 2.00 (m, 4H);
MS (ESI⁺): m/z=532.3 [M+H]⁺.

Example 114

Preparation of 1-(4-(4-(3,4-dichloro-2-fluorophenylamino)-7-methoxyquinazolin-6-yloxy)piperidin-1-yl)-2-(hydroxymethyl)prop-2-en-1-one Step 1) Ethyl 2-((tert-butyldimethylsilyloxy)methyl)acrylate 10.8 g of ethyl 2-(hydroxymethyl)acrylate (*Organic Synthesis, Coll, Vol 8*, 265, 1993) was diluted with 80 ml of N,N'-dimethylformamide, and 18.8 g of tert-butyldimethylsilyl chloride and 11.3 g of imidazole were added thereto. The resulting mixture was incubated at room temperature for two hours. After the reaction terminated, water was added, and the resulting solution was extracted with ethyl acetate. The organic layer was washed five times with water and saturated chloride water, dried over anhydrous sodium sulfate, filtered and distilled under a reduced pressure. The resulting residue was purified by column chromatography (ethyl acetate:n-hexane=1:30) to obtain the title compound (14.7 g, 73%).
¹H-NMR (300 MHz, CDCl₃) δ 6.24 (d, 1H), 5.89 (d, 1H), 4.36 (t, 2H), 4.21 (m, 2H), 1.30 (t, 3H), 0.91 (s, 9H), 0.08 (s, 6H).

Step 2) 2-((tent-butyldimethylsilyloxy)methyl)acrylic acid 4 g of the compound of step 1) was dissolved in 80 ml of a mixed solution of tetrahydrofuran and methanol (1:1), and 27 ml of a 3M lithium hydroxide solution was gradually added thereto at 0° C. while stirring. The resulting mixture was stirred at room temperature for 17 hours, acidified to pH 4 with a 3N HCl, and extracted three times with ether. The organic layer was dried over anhydrous magnesium sulfate, filtered and distilled under a reduced pressure to obtain the title compound (0.5 g, 14%).
¹H-NMR (300 MHz, CDCl₃) δ 6.21 (d, 1H), 5.79 (d, 1H), 4.26 (m, 2H), 0.91 (s, 9H), 0.08 (s, 6H).

Step 3) 2-((tert-butyldimethylsilyloxy)methyl)-1-(4-(4-(3,4-dichloro-2-fluorophenylamino)-7-methoxyquinazolin-6-yloxy)piperidin-1-yl)prop-2-en-1-one The procedure of Example 104 was repeated except for using the compound of step 2) instead of 2-((dimethylamino)methyl)acrylic acid, N-Boc-4-hydroxypiperidine instead of N-Boc-3-hydroxyazetidine, and 3,4-dichloro-2-fluoroaniline instead of 3-chloro-2,4-difluoroaniline in step 2) to obtain the title compound (160 mg, 55%).
¹H-NMR (300 MHz, CDCl₃) δ 8.69 (s, 1H), 8.42 (m, 1H), 7.71 (m, 1H), 7.35 (m, 2H), 7.23 (m, 1H), 6.35 (d, 1H), 5.95 (d, 1H), 4.77 (m, 1H), 4.42 (s 1H), 4.35 (s, 1H), 4.01 (s, 3H), 3.83 (m, 2H), 3.65 (m, 2H), 2.04 (m, 4H), 0.91 (s, 9H), 0.11 (s, 6H);
MS (ESI⁺): m/z=635.1 [M+H]⁺.

Step 4) 1-(4-(4-(3,4-dichloro-2-fluorophenylamino)-7-methoxyquinazolin-6-yloxy)piperidin-1-yl)-2-(hydroxymethyl)prop-2-en-1-one 140 mg of the compound obtained in step 3) was diluted with 3 ml of tetrahydrofuran, and 1.1 ml of a 1.0M tetra-n-butyl ammonium fluoride-containing tetrahydrofuran solution was added thereto. The resulting mixture was incubated at room temperature for three hours. After the reaction terminated, a saturated sodium hydrogen carbonate was added, and the resulting solution was extracted twice with chloroform. The organic layer was dried over anhydrous sodium sulfate, filtered and distilled under a reduced pressure. The resulting residue was purified by column chromatography (ethyl acetate:methylene chloride:methanol=7:7:1) to obtain the title compound (58 mg, 51%).
¹H-NMR (300 MHz, CDCl₃) δ 8.64 (s, 1H), 8.13 (m, 1H), 7.44 (s, 1H), 7.30 (m, 2H), 7.27 (m, 1H), 5.44 (s, 1H), 5.18 (s, 1H), 4.64 (m, 1H), 4.31 (s 2H), 3.99 (s, 3H), 3.89 (m, 2H), 3.59 (m, 2H), 1.94 (m, 4H);
MS (ESI⁺): m/z=521.3 [M+H]⁺.

Example 115

Preparation of 1-(3-(4-(3-chloro-2,4-difluorophenylamino)-7-hydroxyquinazolin-6-yloxy)azetidin-1-yl)prop-2-en-1-one Step 1) tent-butyl 3-(4-(3-chloro-2,4-difluorophenylamino)-7-hydroxyquinazolin-6-yloxy)azetidin-1-carboxylate 1.3 g of 6-(azetidin-3-yloxy)-N-(3-chloro-2,4-difluorophenyl)-7-methoxyquinazolin-4-amine obtained by repeating the procedure of step 6) of Example 1 except for using N-Boc-3-hydroxyazetidine instead of (R)-(-)-N-Boc-3-pyrrolidin, and 0.77 g of pyridine hydrochloride were stirred at 170° C. for three hours. Methylene chloride and methanol were added, and the resulting mixture was distilled and dried under a reduced pressure. The resulting product was diluted with 10 ml of methanol, 0.8 ml of triethylamine and 1.38 g of di-tert-butyl dicarboxylate were gradually added, and the resulting mixture was refluxed at 60° C. for three hours. After the reaction terminated, water was added, and the resulting solution was extracted three times with a mixed solvent of chloroform and 2-propanol (3:1). The organic layer was dried over anhydrous sodium sulfate, filtered and distilled under a reduced pressure. The resulting residue was purified by column chromatography (methylene chloride:methanol=20:1) to obtain the title compound (342 mg, 22%).
¹H-NMR (300 MHz, CDCl₃) δ 8.65 (s, 1H), 7.53-8.45 (m, 1H), 7.41 (s, 1H), 7.31 (s, 1H), 7.18 (bs, 1H), 7.10-7.03 (m, 1H), 4.98 (m, 1H), 4.48-4.40 (m, 2H), 3.57-3.48 (m, 2H), 1.47 (s, 9H).

Step 2) 6-(azetidin-3-yloxy)-4-(3-chloro-2,4-difluorophenylamino)quinazolin-7-ol 100 mg of the compound obtained in step 1) was diluted with 2 ml of methylene chloride, and 0.2 ml of trifluoroacetic acid was added thereto. The resulting mixture was stirred at room temperature for one hour. After the reaction terminated, the resulting solution was distilled under a reduced pressure to remove a solvent. The resulting residue was alkalinized with a saturated sodium bicarbonate and extracted with a mixed solvent of chloroform and 2-propanol (3:1). The organic layer was dried over anhydrous sodium sulfate, filtered and distilled under a reduced pressure. The resulting residue was purified by column chromatography (methylene chloride:methanol=10:1) to obtain the title compound (69 mg, 87%).

¹H-NMR (300 MHz, CDCl₃) δ 8.84 (s, 1H), 8.62-8.54 (m, 1H), 7.48 (s, 1H), 7.41 (s, 1H), 7.25 (bs, 1H), 7.17-7.12 (m, 1H), 4.53 (d, 1H), 4.36-4.24 (m, 2H), 3.21-3.16 (d, 2H).

Step 3) 1-(3-(4-(3-chloro-2,4-difluorophenylamino)-7-hydroxyquinazolin-6-yloxy)azetidin-1-yl)prop-2-en-1-one The procedure of step 7) of Example 1 was repeated except for using the compound obtained in step 2) instead of N-(3-chloro-2,5-difluorophenyl)-7-methoxy-6-((3S)-pyrrolidin-3-yloxy)quinazolin-4-amine to obtain the title compound (20 mg, 25%).

¹H-NMR (300 MHz, CDCl₃+CD₃OD) δ 8.43 (s, 1H), 7.71 (d, 2H), 7.47 (d, 2H), 7.32 (m, 1H), 7.12 (m, 1H), 6.29 (dd, 1H), 5.73 (d, 1H), 5.38 (d, 1H), 4.91 (m, 1H), 3.69 (d, 2H), 3.38 (d, 2H);
MS (ESI⁺): m/z=433.2 [M+H].

Example 116

Preparation of 1-(3-(4-(3-chloro-2,4-difluorophenylamino)-7-(2-methoxyethoxy)quinazolin-6-yloxy)azetidin-1-yl)prop-2-en-1-one Step 1) tert-butyl 3-(4-(3-chloro-2,4-difluorophenylamino)-7-(2-methoxyethy)quinazolin-6-yloxy)azetidin-1-carboxylate 110 mg of the compound obtained in step 1) of Example 115 was diluted with 2 ml of N,N'-dimethylformamide, and 26 µl of 1-bromo-2-methoxyethane, 38 mg of potassium carbonate and 1 mg of potassium iodide were added thereto. The resulting mixture was incubated at 80° C. for six hours. After the reaction terminated, water was added, and the resulting solution was extracted three times with ethyl acetate. The organic layer was washed five times with water and saturated chloride water, dried over anhydrous sodium sulfate, filtered and distilled under a reduced pressure. The resulting residue was purified by column chromatography (methylene chloride:methanol=20:1) to obtain the title compound (40 mg, 32%).

¹H-NMR (300 MHz, CDCl₃) δ 8.00 (s, 1H), 7.67 (s, 1H), 6.99-6.88 (m, 2H), 6.68 (s, 1H), 4.97 (m, 1H), 4.41-4.38 (m, 1H), 4.37-4.29 (m, 1H), 4.08-3.99 (m, 2H), 3.65-3.62 (m, 2H), 3.45-3.40 (m, 2H), 3.31 (s, 3H), 1.45 (s, 9H).

Step 2) 6-(azetidin-3-yloxy)-N-(3-chloro-2,4-difluorophenyl)-7-(2-methoxyethoxy)quinazolin-4-amine The procedure of step 2) of Example 115 was repeated except for using the compound obtained in step 1) instead of tert-butyl 3-(4-(3-chloro-2,4-difluorophenylamino)-7-hydroxyquinazolin-6-yloxy)azetidin-1-carboxylate to obtain the title compound (37 mg, 100%).

¹H-NMR (300 MHz, CDCl₃) δ 8.00 (s, 1H), 7.72 (s, 1H), 7.05-6.89 (m, 2H), 6.73 (s, 1H), 4.38 (m, 1H), 4.36 (d, 1H), 4.13 (d, 1H), 4.04 (t, 2H), 3.66 (t, 2H), 3.31 (s, 3H), 3.06 (m, 2H).

Step 3) 1-(3-(4-(3-chloro-2,4-difluorophenylamino)-7-(2-methoxyethoxy)quinazolin-6-yloxy)azetidin-1-yl)prop-2-en-1-one The procedure of step 3) of Example 115 was repeated except for using the compound obtained in step 2) instead of 6-(azetidin-3-yloxy)-4-(3-chloro-2,4-difluorophenylamino)quinazolin-7-ol to obtain the title compound (21 mg, 50%).

¹H-NMR (300 MHz, CDCl₃) δ 7.91 (s, 1H), 7.67 (s, 1H), 6.98-6.90 (m, 2H), 6.56 (m, 1H), 6.33 (d, 1H), 6.20 (dd, 1H), 5.69 (d, 1H), 4.41 (m, 1H), 4.31 (m, 1H), 4.04-3.98 (m, 3H), 3.74-3.70 (m, 1H), 3.64-3.55 (m, 2H), 3.30 (s, 3H);
MS (ESI⁺): m/z=491.3 [M+H]⁺.

Example 117

Preparation of 1-(4-(4-(3-Chloro-2,4-difluorophenylamino)-7-(2-methoxyethoxy)quinazolin-6-yloxy)piperidin-1-yl)prop-2-en-1-one The procedure of Example 116 was repeated except for using N-Boc-4-hydroxypiperidine instead of N-Boc-3-hydroxyazetidine to obtain the title compound (20 mg, 22%).

¹H-NMR (300 MHz, CDCl₃) δ 8.67 (s, 1H), 8.16 (d, 1H), 7.50 (s, 1H), 7.34 (s, 1H), 6.65 (t, 1H), 6.62 (dd, 1H), 6.31 (d, 1H), 5.73 (d, 1H), 4.72 (m, 1H), 4.33 (m, 2H), 3.89 (m, 6H), 3.59 (s, 3H), 2.07 (m, 2H), 1.99 (m, 2H);
MS (ESI⁺): m/z=519.3 [M+H]⁺.

Example 118

Preparation of 1-(4-(4-(3-chloro-2,4-difluorophenylamino)-7-(3-morpholinopropoxy)quinazolin-6-yloxy)piperidin-1-yl)prop-2-en-1-one The procedure of Example 117 was repeated except for using 4-(3-chloropropyl)morpholine instead of 1-bromo-2-methoxyethane to obtain the title compound (8 mg, 27%).

¹H-NMR (300 MHz, CDCl₃) δ 8.64 (s, 1H), 8.25-8.24 (m, 1H), 7.31-7.29 (s, 2H), 7.09-7.06 (t, 1H), 6.65-6.50 (m, 1H), 6.28 (dd, 1H), 5.70 (dd, 1H), 4.68 (m, 1H), 4.22 (t, 2H), 3.82 (m, 3H), 3.72 (m, 5H), 2.56 (t, 2H), 2.48-2.47 (m, 4H), 2.11-2.06 (m, 2H), 1.96-1.94 (m, 1H);
MS (ESI⁺): m/z=588.4 [M+H]⁺.

Example 119

Preparation of (2S,4S)-methyl 1-acryloyl-4-(4-(3-chloro-2,4-difluorophenylamino)-7-methoxyquinazolin-6-yloxy)piperidin-2-carboxylate The procedure of Example 1 was repeated except for using (2S,4R)-1-tert-butyl 2-methyl 4-hydroxypiperidin-1,2-dicarboxylate (*J. Org. Chem.* 1996, 61, 2226-2231) instead of (R)-(-)-N-Boc-3-pyrrolidinol in step 6) to obtain the title compound (45 mg, 32%).

¹H-NMR (300 MHz, CDCl₃) δ 9.00 (s, 1H), 8.64 (m, 1H), 8.27 (bs, 1H), 8.22 (s, 1H), 7.04 (td, 1H), 6.67 (m, 1H), 6.34 (m, 1H), 5.82 (m, 2H), 4.80 (m, 1H), 4.56 (m, 1H), 4.03 (s, 3H), 3.84 (s, 3H), 3.28 (m, 1H), 3.07 (m, 1H), 2.21 (m, 2H), 2.03 (m, 1H), 1.69 (m, 1H);
MS (ESI⁺): m/z=533.3 [M+H]⁺.

Example 120

Preparation of (2S,4S)-1-acryloyl-4-(4-(3-chloro-2,4-difluorophenylamino)-7-methoxyquinazolin-6-yloxy)piperidin-2-carboxamide Step 1) (2S,4S)-1-tent-butyl 2-methyl 4-(4-(3-chloro-2,4-difluorophenylamino)-7-methoxyquinazolin-6-yloxy)piperidin-1,2-dicarboxylate The procedure of step 6) of Example 1 was repeated except that (2S,4R)-1-tert-butyl 2-methyl 4-hydroxypiperidin-1,2- dicarboxylate (*J. Org. Chem.* 1996, 61, 2226-2231) was used instead of (R)-(−)-N-Boc-3-pyrrolidinol and the deprotection reaction using trifluoroacetic acid was omitted to thereby obtain the title compound (1.7 g, 40%).

$^1$H-NMR (300 MHz, CDCl$_3$) δ 8.59 (s, 1H), 7.94 (m, 1H), 7.85 (s, 1H), 7.25 (s, 1H), 6.95 (td, 1H), 5.10 (m, 1H), 4.41 (m, 1H), 4.13 (m, 1H), 3.98 (s, 3H), 3.78 (s, 3H), 2.89 (m, 2H), 2.08 (m, 1H), 1.78 (m, 2H), 1.47 (s, 3H).

Step 2) (2S,4S)-1-(tert-butoxycarbonyl)-4-(4-(3-chloro-2,4-difluorophenylamino)-7-methoxyquinazolin-6-yloxy)piperidin-2-carboxylic acid 1.66 g of the compound obtained in step 1) was diluted with 18 ml of a 50% tetrahydrofuran, and 145 mg of lithium hydroxide monohydrate was added thereto. The resulting mixture was stirred at room temperature for three hours. After the reaction terminated, the resulting solution was acidified with acetic acid and extracted twice with ethyl acetate. The organic layer was dried over anhydrous sodium sulfate, filtered and distilled under a reduced pressure. The resulting residue was purified by column chromatography (methylene chloride:ethyl acetate:methanol=5:5:1) to obtain the title compound (1.5 g, 92%).

$^1$H-NMR (300 MHz, CDCl$_3$) δ 8.31 (s, 1H), 7.74 (s, 1H), 7.60 (m, 2H), 7.12 (m, 2H), 4.60 (m, 1H), 4.09 (m, 2H), 3.94 (s, 3H), 3.29 (m, 1H), 2.70 (m, 1H), 2.31 (m, 1H), 2.07 (m, 1H), 1.92 (m, 1H), 1.43 (s, 9H).

Step 3) (2S,4S)-tert-butyl 2-carbamoyl-4-(4-(3-chloro-2,4-difluorophenylamino)-7-methoxyquinazolin-6-yloxy)piperidin-1-carboxylate 1.93 g of the compound obtained in step 1) was diluted with 17 ml of tetrahydrofuran, and 0.53 ml of N-methyl morpholine and 0.58 ml of isobutyl chloroformate were added thereto at −15° C. The resulting mixture was stirred for 10 minutes, and 1.0 ml of 28% aqueous ammonia was added thereto. While gradually heating to room temperature, the resulting mixture was incubated for one hour. After the reaction terminated, water was added, and the resulting solution was extracted with chloroform. The organic layer was washed with water and saturated chloride water, dried over anhydrous sodium sulfate, filtered and distilled under a reduced pressure. The resulting residue was purified by column chromatography (methylene chloride:ethyl acetate=1:3) to obtain the title compound (1.0 g, 52%).

$^1$H-NMR (300 MHz, CDCl$_3$) δ 8.61 (s, 1H), 8.02 (m, 2H), 7.05 (m, 1H), 6.48 (s, 1H), 5.52 (m, 1H), 4.74 (m, 1H), 4.33 (m, 1H), 4.02 (s, 3H), 3.06 (m, 2H), 1.90 (m, 2H), 1.49 (m, 1H).

Step 4) (2S,4S)-4-(4-(3-chloro-2,4-difluorophenylamino)-7-methoxyquinazolin-6-yloxy)piperidin-2-carboxamide The procedure of step 2) of Example 115 was repeated except for using the compound obtained in step 3) instead of tent-butyl 3-(4-(3-chloro-2,4-difluorophenylamino)-7-hydroxyquinazolin-6-yloxy)azetidin-1-carboxylate to obtain the title compound (580 mg, 71%).

$^1$H-NMR (300 MHz, CDCl$_3$) δ 8.32 (s, 1H), 7.76 (s, 1H), 7.53 (s, 1H), 7.19 (m, 1H), 6.71 (s, 1H), 4.92 (m, 2H), 4.00 (s, 3H), 3.12 (m, 1H), 2.96 (m, 1H), 2.23 (m, 1H), 1.87 (m, 3H), 1.26 (s, 9H).

Step 5) (2S,4S)-1-acryloyl-4-(4-(3-chloro-2,4-difluorophenylamino)-7-methoxyquinazolin-6-yloxy)piperidin-2-carboxamide The procedure of step (1-7) was repeated except for using the compound obtained in step 4) instead of N-(3-chloro-2,4-difluorophenyl)-7-methoxy-6-((3S)-pyrrolidin-3-yloxy)quinazolin-4-amine to obtain the title compound (10 mg, 69%).

$^1$H-NMR (300 MHz, CDCl$_3$) δ 8.58 (s, 1H), 8.08 (bs, 1H), 7.99 (bs, 2H), 7.24 (s, 1H), 7.00 (td, 1H), 6.66 (m, 2H), 6.36 (d, 1H), 5.82 (d, 2H), 5.49 (m, 1H), 4.88 (m, 1H), 4.15 (m, 1H), 4.00 (s, 3H), 3.28 (m, 1H), 3.01 (m, 1H), 2.22 (m, 1H), 2.15 (m, 1H), 2.02 (m, 1H), 1.55 (m, 1H);

MS (ESI$^+$): m/z=518.2 [M+H]$^+$.

Example 121

Preparation of (2S,4S)-1-acryloyl-4-(4-(3-chloro-2,4-difluorophenylamino)-7-methoxyquinazolin-6-yloxy)-N-methylpiperidin-2-carboxamide The procedure of Example 120 was repeated except for using a 2.0M methylamine-containing tetrahydrofuran solution instead of 28% aqueous ammonia in step 3) to obtain the title compound (240 mg, 66%).

$^1$H-NMR (300 MHz, CDCl$_3$) δ 8.63 (s, 1H), 8.34 (s, 1H), 8.19 (s, 1H), 8.13 (m, 1H), 7.04 (td, 1H), 6.70 (dd, 2H), 6.45 (dd, 1H), 5.88 (dd, 1H), 5.50 (m, 1H), 4.99 (m, 1H), 4.21 (m, 1H), 4.02 (s, 3H), 3.30 (t, 1H), 3.07 (d, 2H), 2.25 (m, 1H), 2.02 (m, 1H), 1.80 (m, 3H), 1.58 (m, 1H);

MS (ESI$^+$): m/z=532.3 [M+H]$^+$.

Example 122

Preparation of (2S,4S)-1-acryloyl-4-(4-(3-chloro-2,4-difluorophenylamino)-7-methoxyquinazolin-6-yloxy)-N-ethylpiperidin-2-carboxamide The procedure of Example 120 was repeated except for using a 2.0M ethylamine-containing tetrahydrofuran solution instead of 28% aqueous ammonia in step 3) to obtain the title compound (25 mg, 60%).

$^1$H-NMR (300 MHz, CDCl$_3$) δ 8.63 (s, 1H), 8.37 (s, 1H), 8.21 (s, 1H), 8.16 (m, 1H), 7.08 (td, 1H), 6.71 (dd, 2H), 6.45 (dd, 1H), 5.88 (dd, 1H), 5.51 (m, 1H), 4.99 (m, 1H), 4.22 (m, 1H), 4.08 (s, 3H), 3.41 (m, 1H), 3.26 (d, 2H), 2.26 (m, 1H), 2.02 (m, 1H), 1.57 (m, 1H), 1.25 (m, 2H), 1.14 (m, 3H);

MS (ESI$^+$): m/z=546.2 [M+H]$^+$.

Example 123

Preparation of (2S,4S)-1-acryloyl-4-(4-(3-chloro-2,4-difluorophenylamino)-7-methoxyquinazolin-6-yloxy)-N-propylpiperidin-2-carboxamide The procedure of Example 120 was repeated except for using propylamine instead of 28% aqueous ammonia in step 3) to obtain the title compound (3.8 mg, 11%).

$^1$H-NMR (300 MHz, CDCl$_3$) δ 8.63 (s, 1H), 8.38 (s, 1H), 8.21 (s, 1H), 8.16 (m, 1H), 7.06 (td, 1H), 6.71 (dd, 2H), 6.44 (dd, 1H), 5.88 (dd, 1H), 5.51 (m, 1H), 4.99 (m, 1H), 4.18 (m, 1H), 4.03 (s, 3H), 3.25 (m, 3H), 3.07 (d, 1H), 2.22 (m, 1H), 2.04 (m, 1H), 1.55 (m, 4H), 1.25 (m, 2H), 0.89 (t, 3H);

MS (ESI$^+$): m/z=560.0 [M+H]$^+$.

Example 124

Preparation of (2S,4S)-1-acryloyl-4-(4-(3-chloro-2, 4-difluorophenylamino)-7-methoxyquinazolin-6-yloxy)-N-isopropylpiperidin-2-carboxamide The procedure of Example 120 was repeated except for using isopropylamine instead of 28% aqueous ammonia in step 3) to obtain the title compound (10.6 mg, 16%).

$^1$H-NMR (300 MHz, CDCl$_3$) δ 8.63 (s, 1H), 8.38 (s, 1H), 8.21 (s, 1H), 8.16 (m, 1H), 7.06 (td, 1H), 6.68 (dd, 1H), 6.48 (m, 2H), 5.87 (dd, 1H), 5.48 (m, 1H), 4.98 (m, 1H), 4.12 (m, 2H), 4.02 (s, 3H), 3.23 (m, 1H), 3.07 (m, 1H), 2.24 (m, 1H), 2.02 (m, 1H), 1.85 (m, 2H), 1.51 (m, 1H), 1.03 (m, 6H);

MS (ESI$^+$): m/z=560.0 [M+H]$^+$.

Example 125

Preparation of (2S,4S)-1-acryloyl-4-(4-(3-chloro-2, 4-difluorophenylamino)-7-methoxyquinazolin-6-yloxy)-N-hydroxypiperidin-2-carboxamide The procedure of Example 120 was repeated except for using hydroxylamine instead of 28% aqueous ammonia in step 3) to obtain the title compound (13 mg, 18%).

$^1$H-NMR (300 MHz, CDCl$_3$) δ 8.32 (s, 1H), 7.79 (s, 1H), 7.52 (m, 1H), 7.18 (m, 2H), 6.82 (m, 1H), 6.25 (d, 1H), 5.77 (m, 1H), 5.38 (m, 1H), 4.85 (m, 1H), 4.15 (m, 1H), 3.97 (s, 3H), 2.70 (m, 1H), 2.31 (m, 1H), 1.90 (m, 1H), 1.67 (m, 1H), 1.28 (m, 1H);

MS (ESI$^+$): m/z=534.2 [M+H]$^+$.

Example 126

Preparation of (2S,4S)-1-acryloyl-4-(4-(3-chloro-2, 4-difluorophenylamino)-7-methoxyquinazolin-6-yloxy)-N-(2-hydroxyethyl)piperidin-2-carboxamide The procedure of Example 120 was repeated except for using ethanolamine instead of 28% aqueous ammonia in step 3) to obtain the title compound (10 mg, 25%).

$^1$H-NMR (300 MHz, CDCl$_3$) δ 8.32 (s, 1H), 7.80 (s, 1H), 7.52 (m, 1H), 7.18 (m, 2H), 6.82 (m, 1H), 6.25 (d, 1H), 5.80 (m, 1H), 5.40 (m, 1H), 4.85 (m, 1H), 4.15 (m, 1H), 3.97 (s, 3H), 3.89 (m, 2H), 3.26 (m, 2H), 2.70 (m, 1H), 2.31 (m, 1H), 1.95 (m, 1H), 1.71 (m, 1H), 1.20 (m, 1H);

MS (ESI$^+$): m/z=562.3 [M+H]$^+$.

Example 127

Preparation of (2S,4S)-1-acryloyl-4-(4-(3-chloro-2, 4-difluorophenylamino)-7-methoxyquinazolin-6-yloxy)-N-(2-methoxyethyl)piperidin-2-carboxamide The procedure of Example 120 was repeated except for using 2-methyloxyethylamine instead of 28% aqueous ammonia in step 3) to obtain the title compound (12 mg, 25%).

$^1$H-NMR (300 MHz, CDCl$_3$) δ 8.46 (s, 1H), 7.87 (s, 1H), 7.65 (m, 1H), 7.13 (s, 1H), 6.96 (m, 1H), 6.68 (m, 1H), 6.40 (dd, 1H), 5.85 (d, 1H), 4.45 (m, 1H), 3.92 (m, 4H), 3.26 (m, 7H), 2.83 (m, 1H), 2.59 (m, 1H), 1.91 (m, 2H), 1.76 (m, 1H);

MS (ESI$^+$): m/z=576.2 [M+H]$^+$.

Example 128

Preparation of (2S,4S)-1-acryloyl-4-(4-(3-chloro-2, 4-difluorophenylamino)-7-methoxyquinazolin-6-yloxy)-N-(2-(methylthio)ethyl)piperidin-2-carboxamide The procedure of Example 120 was repeated except for using 2-(methylthio)ethylamine instead of 28% aqueous ammonia in step 3) to obtain the title compound (40 mg, 47%).

$^1$H-NMR (300 MHz, CDCl$_3$) δ 8.63 (s, 1H), 8.30 (s, 1H), 8.12 (m, 2H), 7.12 (m, 1H), 7.09 (m, 1H), 6.86 (m, 1H), 6.54 (dd, 1H), 5.92 (d, 1H), 5.63 (m, 1H), 4.95 (m, 1H), 4.15 (m, 1H), 4.03 (s, 3H), 3.78 (m, 1H), 3.57 (m, 2H), 3.15 (m, 1H), 2.87 (m, 2H), 2.21 (m, 1H), 2.06 (s, 3H), 1.65 (m, 2H), 1.60 (m, 1H);

MS (ESI$^+$): m/z=592.3 [M+H]$^+$.

Example 129

Preparation of (2S,4S)-1-acryloyl-4-(4-(3-chloro-2, 4-difluorophenylamino)-7-methoxyquinazolin-6-yloxy)-N-(2-(methylsulfonyl)ethyl)piperidin-2-carboxamide 41 mg of the compound obtained in Example 128 was diluted with 1 ml of tetrahydrofuran and 1 ml of a saturated sodium bicarbonate, and 34 mg of 3-chloroperoxybenzoic acid was added thereto. The resulting mixture was incubated at room temperature for two hours. After the reaction terminated, water was added, and the resulting solution was extracted twice with ethyl acetate. The organic layer was washed with water and saturated chloride water, dried over anhydrous sodium sulfate, filtered and distilled under a reduced pressure. The resulting residue was purified by column chromatography (methylene chloride:ethyl acetate: methanol=10:10:1) to obtain the title compound (20 mg, 47%).

$^1$H-NMR (300 MHz, CDCl$_3$) δ 8.64 (s, 1H), 8.26 (m, 1H), 8.18 (s, 1H), 8.09 (s, 1H), 7.28 (s, 1H), 7.09 (m, 1H), 6.68 (dd, 1H), 6.42 (d, 1H), 5.82 (d, 1H), 5.56 (m, 1H), 4.85 (m, 1H), 4.21 (m, 1H), 4.02 (s, 3H), 3.98 (m, 1H), 3.75 (m, 1H), 3.37 (m, 2H), 3.10 (m, 1H), 2.95 (s, 3H), 2.24 (m, 1H), 2.02 (m, 1H), 1.52 (m, 1H);

MS (ESI$^+$): m/z=624.3 [M+H]$^+$.

Example 130

Preparation of (2S,4S)-1-acryloyl-4-(4-(3-chloro-2, 4-difluorophenylamino)-7-methoxyquinazolin-6-yloxy)-N-(2-(dimethylamino)ethyl)piperidin-2-carboxamide The procedure of Example 120 was repeated except for using N,N-dimethylethylene diamine instead of 28% aqueous ammonia in step 3) to obtain the title compound (39 mg, 44%).

$^1$H-NMR (300 MHz, CDCl$_3$) δ 8.62 (s, 1H), 8.25 (s, 2H), 8.12 (m, 1H), 7.30 (m, 1H), 7.05 (td, 1H), 6.68 (m, 1H), 6.41

(dd, 1H), 5.85 (d, 1H), 5.59 (m, 1H), 4.83 (m, 1H), 4.15 (m, 1H), 4.02 (s, 3H), 3.30 (m, 2H), 3.14 (m, 1H), 2.55 (m, 3H), 2.29 (m, 8H), 2.01 (m, 1H), 1.50 (m, 1H);
MS (ESI$^+$): m/z=589.3 [M+H]$^+$.

Example 131

Preparation of (2S,4S)-1-acryloyl-4-(4-(3-chloro-2,4-difluorophenylamino)-7-methoxyquinazolin-6-yloxy)-N-(3-hydroxypropyl)piperidin-2-carboxamide The procedure of Example 120 was repeated except for using 3-amino-1-propanol instead of 28% aqueous ammonia in step 3) to obtain the title compound (50 mg, 27%).
$^1$H-NMR (300 MHz, CDCl$_3$) δ 8.62 (s, 1H), 8.19 (s, 1H), 8.10 (s, 1H), 7.26-7.01 (m, 2H), 6.67 (m, 1H), 6.38 (d, 1H), 5.84 (d, 1H), 4.92 (m, 1H), 4.17 (m, 1H), 4.02 (s, 3H), 3.98 (m, 1H), 3.68 (m, 2H), 3.46 (m, 2H), 3.33 (m, 1H), 3.11 (m, 2H), 2.21 (m 1H), 2.04 (m, 1H), 1.60 (m, 1H);
MS (ESI$^+$): m/z=576.2 [M+H]$^+$.

Example 132

Preparation of (2S,4S)-1-acryloyl-4-(4-(3-chloro-2,4-difluorophenylamino)-7-methoxyquinazolin-6-yloxy)-N-(2-morpholinoethyl)piperidin-2-carboxamide The procedure of Example 120 was repeated except for using N-(2-aminoethyl)morpholine instead of 28% aqueous ammonia in step 3) to obtain the title compound (100 mg, 43%).
$^1$H-NMR (300 MHz, CDCl$_3$) δ 8.63 (s, 1H), 8.32 (s, 1H), 8.17 (s, 1H), 7.08-7.02 (m, 2H), 6.67-6.65 (m, 1H), 6.45 (d, 1H), 5.87 (d, 1H), 5.56 (m, 1H), 4.95 (m, 1H), 4.02 (s, 3H), 3.70-3.65 (m, 4H), 3.55-3.25 (m, 2H), 3.02 (d, 1H), 2.49-2.41 (m, 8H), 2.35 (m, 1H), 2.21 (m 1H), 1.55 (m, 1H);
MS (ESI$^+$): m/z=631.4 [M+H]$^+$.

Example 133

Preparation of (2R,4R)-methyl 1-acryloyl-4-(4-(3-chloro-2,4-difluorophenylamino)-7-methoxyquinazolin-6-yloxy)piperidin-2-carboxylate The procedure of Example 1 was repeated except for using (2R,4S)-1-tert-butyl 2-methyl 4-hydroxypiperidin-1,2-dicarboxylate (J. Org. Chem. 1996, 61, 2226-2231) instead of (R)-(−)-N-Boc-3-pyrrolidinol in step 6) to obtain the title compound (42 mg, 34%).
$^1$H-NMR (300 MHz, CDCl$_3$) δ 9.00 (s, 1H), 8.64 (m, 1H), 8.27 (bs, 1H), 8.22 (s, 1H), 7.04 (td, 1H), 6.67 (m, 1H), 6.34 (m, 1H), 5.82 (m, 2H), 4.80 (m, 1H), 4.56 (m, 1H), 4.03 (s, 3H), 3.84 (s, 3H), 3.28 (m, 1H), 3.07 (m, 1H), 2.21 (m, 1H), 2.03 (m, 1H), 1.69 (m, 2H);
MS (ESI$^+$): m/z=533.3 [M+H]$^+$.

Example 134

Preparation of (2R,4R)-1-acryloyl-4-(4-(3-chloro-2,4-difluorophenylamino)-7-methoxyquinazolin-6-yloxy)piperidin-2-carboxylic acid 15 mg of the compound obtained in Example 133 was dissolved in 0.2 ml of a mixed solvent of tetrahydrofuran and methanol (1:1), and 1.4 mg of lithium hydroxide monohydrate was added thereto at 0° C. The resulting mixture was incubated at room temperature for one hour. After the reaction terminated, the resulting solution was acidified to pH 4 with a 3N HCl and extracted twice with methylene chloride. The organic layer was dried over anhydrous magnesium sulfate, filtered and distilled under a reduced pressure. The resulting residue was purified by column chromatography (methylene chloride:ethyl acetate:methanol=1:1:1) to obtain the title compound (10 mg, 69%).
$^1$H-NMR (300 MHz, CDCl$_3$) δ 8.41 (s, 1H), 7.83 (s, 1H), 7.51 (m, 1H), 7.19 (m, 2H), 6.81 (m, 1H), 6.20 (m, 1H), 5.74 (m, 1H), 4.65 (m, 1H), 4.15 (m, 1H), 3.99 (s, 3H), 3.49 (m, 1H), 2.84 (m, 1H), 2.34 (m, 1H), 2.00 (m, 1H), 1.27 (m, 2H);
MS (ESI$^+$): m/z=519.3 [M+H]$^+$.

Example 135

Preparation of (2R,4R)-1-acryloyl-4-(4-(3-chloro-2,4-difluorophenylamino)-7-methoxyquinazolin-6-yloxy)piperidin-2-carboxamide The procedure of Example 120 was repeated except for using (2R,4S)-1-tent-butyl 2-methyl 4-hydroxypiperidin-1,2-dicarboxylate instead of (2S,4R)-1-tert-butyl 2-methyl 4-hydroxypiperidin-1,2-dicarboxylate in step 1) to obtain the title compound (50 mg, 45%).
$^1$H-NMR (300 MHz, CDCl$_3$) δ 8.63 (s, 1H), 8.36 (s, 1H), 8.15 (m, 2H), 7.27 (s, 1H), 7.04 (td, 1H), 6.70 (m, 2H), 6.45 (dd, 1H), 5.89 (dd, 1H), 5.51 (m, 1H), 5.00 (m, 1H), 4.22 (m, 1H), 4.03 (s, 3H), 3.26 (m, 1H), 3.07 (m, 1H), 2.25 (m, 1H), 2.04 (m, 1H), 1.55 (m, 1H), 0.85 (m, 1H);
MS (ESI$^+$): m/z=518.2 [M+H]$^+$.

Example 136

Preparation of (2R,4R)-1-acryloyl-4-(4-(3-chloro-2,4-difluorophenylamino)-7-methoxyquinazolin-6-yloxy)-N-methylpiperidin-2-carboxamide The procedure of Example 135 was repeated except for using a 2.0M methylamine-containing tetrahydrofuran solution instead of 28% aqueous ammonia to obtain the title compound (37 mg, 35%).
$^1$H-NMR (300 MHz, CDCl$_3$) δ 8.60 (s, 1H), 8.12 (s, 1H), 8.01 (m, 1H), 7.94 (s, 1H), 7.03 (td, 1H), 6.70 (m, 2H), 6.44 (d, 1H), 5.87 (d, 1H), 5.55 (m, 1H), 4.95 (m, 1H), 4.22 (m, 1H), 4.01 (s, 3H), 3.29 (t, 1H), 3.07 (d, 2H), 2.26 (m, 1H), 2.01 (m, 3H), 1.56 (m, 1H);
MS (ESI$^+$): m/z=532.3 [M+H]$^+$.

Example 137

Preparation of (2R,4R)-1-acryloyl-4-(4-(3-chloro-2,4-difluorophenylamino)-7-methoxyquinazolin-6-yloxy)-N-hydroxypiperidin-2-carboxamide The procedure of Example 135 was repeated except for using hydroxylamine instead of 28% aqueous ammonia to obtain the title compound (15 mg, 9.8%).
$^1$H-NMR (300 MHz, CDCl$_3$) δ 8.30 (s, 1H), 7.75 (s, 1H), 7.51 (m, 1H), 7.18 (m, 2H), 6.80 (m, 1H), 6.20 (d, 1H), 5.77 (m, 1H), 5.33 (m, 1H), 4.80 (m, 1H), 4.11 (m, 1H), 3.97 (s, 3H), 2.69 (m, 1H), 2.31 (m, 1H), 1.90 (m, 1H), 1.67 (m, 1H), 1.28 (m, 1H);
MS (ESI$^+$): m/z=534.2 [M+H]$^+$.

Example 138

Preparation of (2R,4R)-1-acryloyl-4-(4-(3-chloro-2,4-difluorophenylamino)-7-methoxyquinazolin-6-yloxy)-N-(2-(methylsulfonyl)ethyl)piperidin-2-carboxamide The procedure of Example 129 was repeated except for using (2R,4S)-1-tert-butyl 2-methyl 4-hydroxypiperidin-1,2-dicarboxylate instead of (2S,4R)-1-tert-butyl 2-methyl 4-hydroxypiperidin-1,2-dicarboxylate to obtain the title compound (18 mg, 33%).

$^1$H-NMR (300 MHz, CDCl$_3$) δ 8.70 (s, 1H), 8.26 (s, 1H), 8.11 (s, 1H), 7.54-7.53 (m, 1H), 7.13-7.10 (m, 1H), 6.68 (dd, 1H), 6.66 (d, 1H), 5.87 (d, 1H), 4.87 (m, 1H), 4.02 (m, 1H), 4.07 (s, 3H), 3.98 (m, 1H), 3.88 (m, 1H), 3.43 (m, 2H), 3.29 (m, 1H), 3.09 (m 1H), 2.98 (s, 3H), 2.24 (m, 1H), 2.05 (m, 2H), 1.60-1.54 (m, 1H).

Example 139

Preparation of (2R,4R)-1-acryloyl-4-(4-(3,4-dichloro-2-fluorophenylamino)-7-methoxyquinazolin-6-yloxy)piperidin-2-carboxamide The procedure of Example 129 was repeated except for using 3,4-dichloro-2-fluoroaniline instead of 3-chloro-2,4-difluoroaniline to obtain the title compound (70 mg, 60%).

$^1$H-NMR (300 MHz, CDCl$_3$) δ 8.61 (s, 1H), 8.02 (s, 1H), 7.85 (t, 1H), 7.38 (s, 2H), 7.37 (dd, 1H), 6.73 (dd, 1H), 6.34 (dd, 1H), 5.88 (d, 1H), 5.55 (m, 1H), 4.92 (m, 1H), 4.16 (m, 1H), 4.03 (s, 3H), 3.36 (m, 2H), 2.98 (m, 1H), 2.29 (m, 1H), 1.68 (m, 1H), 1.56 (m, 1H);

MS (ESI$^+$): m/z=534.5 [M+H]$^+$.

Example 140

Preparation of (2R,4R)-1-acryloyl-4-(4-(4-bromo-2-fluorophenylamino)-7-methoxyquinazolin-6-yloxy)piperidin-2-carboxamide The procedure of Example 129 was repeated except for using 4-bromo-2-fluoroaniline instead of 3-chloro-2,4-difluoroaniline to obtain the title compound (40 mg, 32%).

$^1$H-NMR (300 MHz, CDCl$_3$) δ 8.36 (s, 1H), 7.41 (s, 1H), 7.24 (s, 1H), 6.95 (m, 1H), 6.89 (s, 1H), 6.33 (d, 1H), 6.62 (m, 1H), 6.12 (d, 1H), 5.55 (d, 1H), 4.37 (m, 1H), 4.28 (m, 2H), 3.73 (s, 3H), 3.34 (m, 2H), 2.12 (m, 2H);

MS (ESI$^+$): m/z=544.1 [M+H]$^+$.

The compounds obtained in Examples 1 to 140 are represented by the following structural formulae, as shown in Table 1 below.

TABLE 1

| Example | Compound | Structure |
|---|---|---|
| 1 | 1-((3S)-3-(4-(3-chloro-2,4-difluorophenylamino)-7-methoxyquinazolin-6-yloxy)pyrrolidin-1-yl)prop-2-en-1-one | 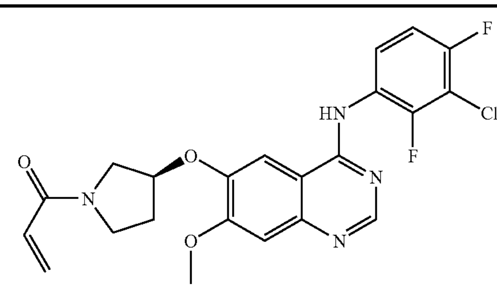 |
| 2 | (E)-1-((3S)-3-(4-(3-chloro-2,4-difluorophenylamino)-7-methoxyquinazolin-6-yloxy)pyrrolidin-1-yl)but-2-en-1-one | 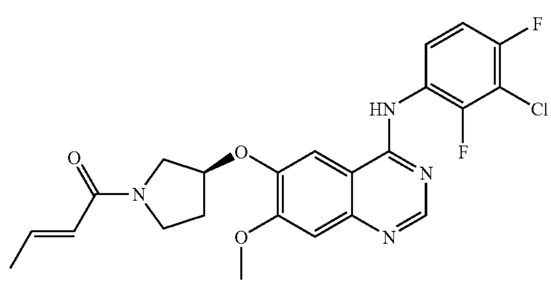 |
| 3 | 1-((3S)-3-(4-(3-chloro-2,4-difluorophenylamino)-7-methoxyquinazolin-6-yloxy)pyrrolidin-1-yl)but-2-yn-1-one | 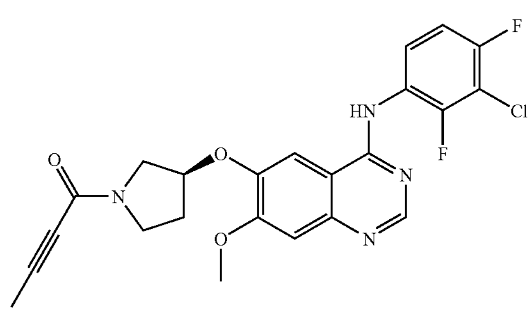 |

TABLE 1-continued

| Example | Compound | Structure |
|---|---|---|
| 4 | 1-((3S)-3-(4-(3-chloro-2,4-difluorophenylamino)-7-methoxyquinazolin-6-yloxy)pyrrolidin-1-yl)-5-(4-methylpiperazin-1-yl)pent-2-yn-1-one | 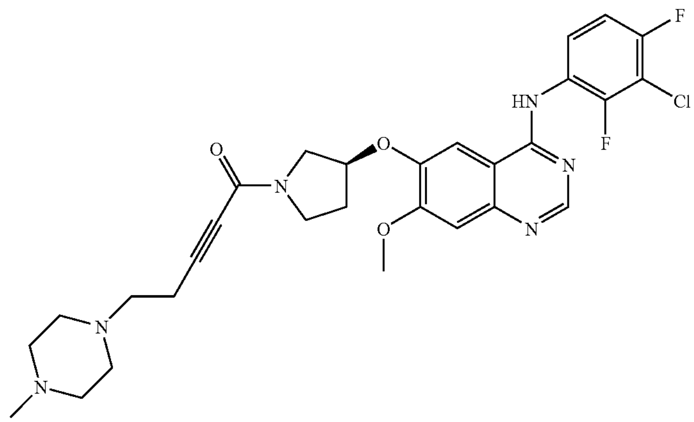 |
| 5 | 1-((3S)-3-(4-(3-chloro-2,4-difluorophenylamino)-7-methoxyquinazolin-6-yloxy)pyrrolidin-1-yl)-4-(dimethylamino)but-2-yn-1-one | 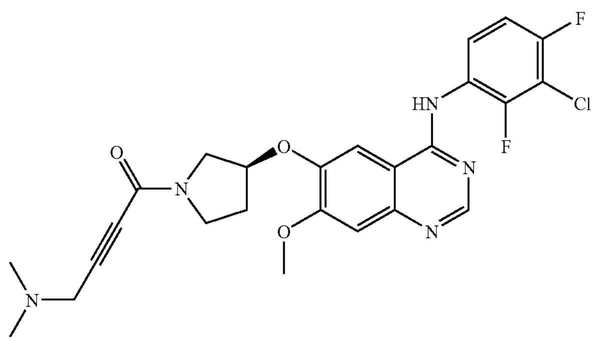 |
| 6 | 1-((3S)-3-(4-(3-chloro-2-fluorophenylamino)-7-methoxyquinazolin-6-yloxy)pyrrolidin-1-yl)prop-2-en-1-one | 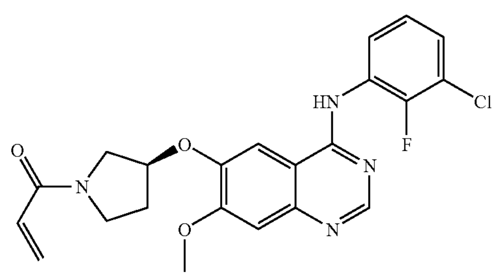 |
| 7 | 1-((3S)-3-(4-(4-bromo-3-chloro-2-fluorophenylamino)-7-methoxyquinazolin-6-yloxy)pyrrolidin-1-yl)prop-2-en-1-one | 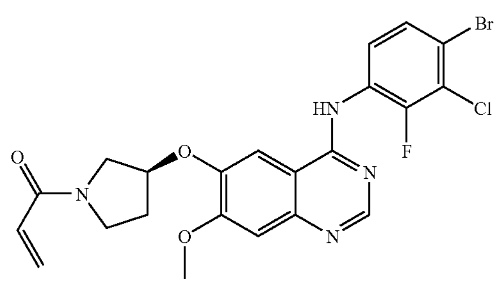 |
| 8 | 1-((3S)-3-(4-(3,4-dichloro-2-fluorophenylamino)-7-methoxyquinazolin-6-yloxy)pyrrolidin-1-yl)prop-2-en-1-one | 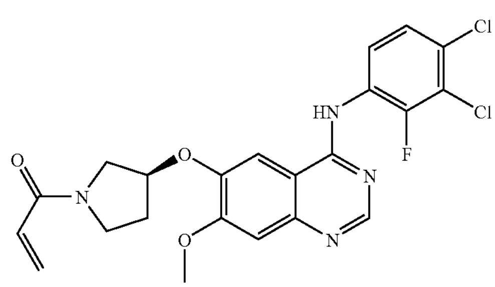 |

TABLE 1-continued

| Example | Compound | Structure |
|---|---|---|
| 9 | 1-((3S)-3-(4-(4-bromo-2-fluorophenylamino)-7-methoxyquinazolin-6-yloxy)pyrrolidin-1-yl)prop-2-en-1-one | 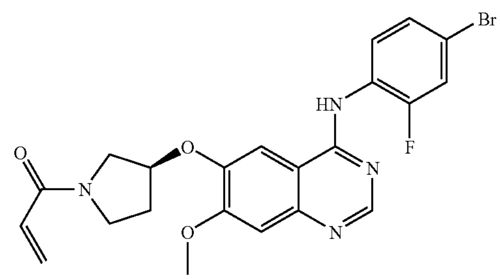 |
| 10 | 1-((3S)-3-(4-(3-chloro-4-(pyridin-2-ylmethoxy)phenylamino)-7-methoxyquinazolin-6-yloxy)pyrrolidin-1-yl)prop-2-en-1-one | 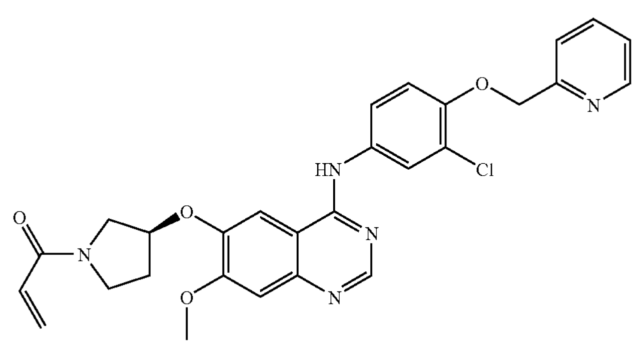 |
| 11 | 1-((3S)-3-(7-methoxy-4-((1R)-1-phenylethylamine)quinazolin-6-yloxy)pyrrolidin-1-yl)prop-2-en-1-one | 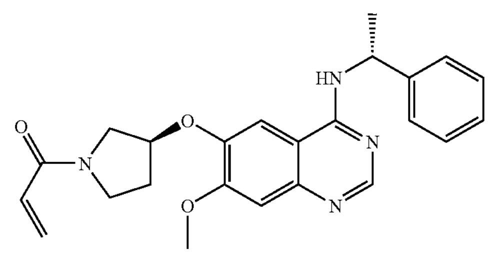 |
| 12 | 1-((3S)-3-(4-(1-(3-fluorobenzyl)-1H-indazol-5-ylamino)-7-methoxyquinazolin-6-yloxy)pyrrolidin-1-yl)prop-2-en-1-one | 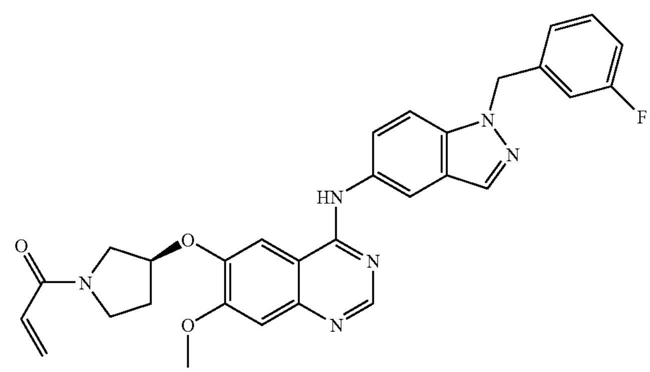 |
| 13 | 1-((3S)-3-(4-(3-chloro-4-fluorophenylamino)-7-methoxyquinazolin-6-yloxy)pyrrolidin-1-yl)prop-2-en-1-one | 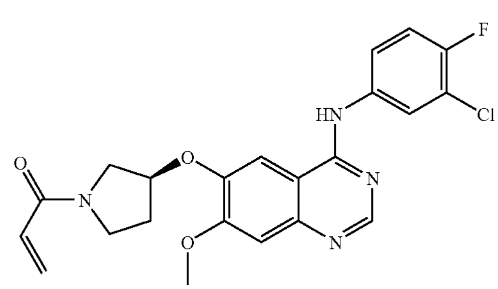 |

TABLE 1-continued

| Example | Compound | Structure |
|---|---|---|
| 14 | 1-((3R)-3-(4-(3-chloro-4-fluorophenylamino)-7-methoxyquinazolin-6-yloxy)pyrrolidin-1-yl)prop-2-en-1-one | 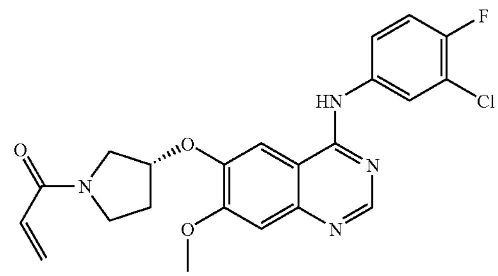 |
| 15 | 1-((3S)-3-(4-(3-chloro-2,4-difluorophenylamino)quinazolin-6-yloxy)pyrrolidin-1-yl)prop-2-en-1-one | 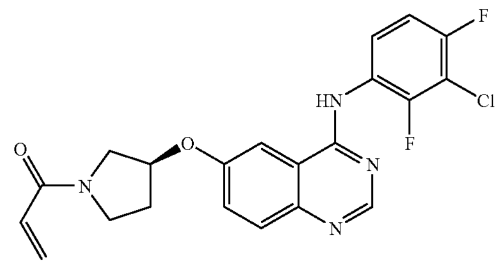 |
| 16 | 1-((3S)-3-(4-(3-chloro-4-(3-fluorobenzyloxy)phenylamino)quinazolin-6-yloxy)pyrrolidin-1-yl)prop-2-en-1-one | 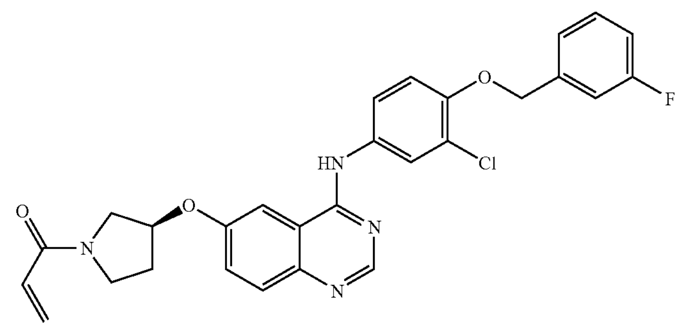 |
| 17 | 1-(3-(4-(3-chloro-2,4-difluorophenylamino)-7-methoxyquinazolin-6-yloxy)azetidin-1-yl)prop-2-en-1-one | 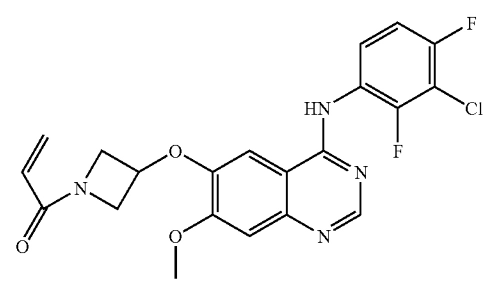 |
| 18 | 1-(3-(4-(3-chloro-2,4-difluorophenylamino)-7-methoxyquinazolin-6-yloxy)piperidin-1-yl)prop-2-en-1-one | 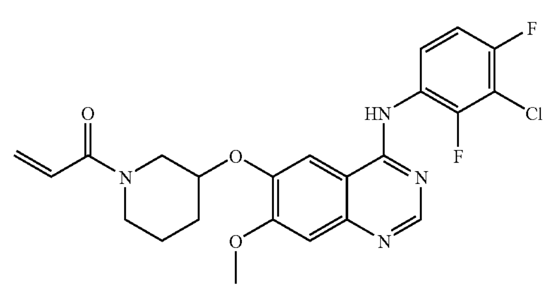 |

TABLE 1-continued

| Example | Compound | Structure |
|---|---|---|
| 19 | 1-(4-(4-(3-chloro-2,4-difluorophenylamino)-7-methoxyquinazolin-6-yloxy)piperidin-1-yl)prop-2-en-1-one | 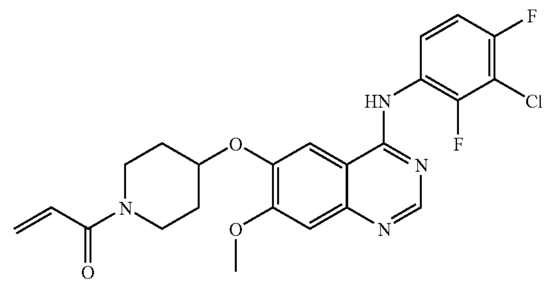 |
| 20 | 1-((3R)-3-(4-(3-chloro-2,4-difluorophenylamino)-7-methoxyquinazolin-6-yloxy)pyrrolidin-1-yl)prop-2-en-1-one | 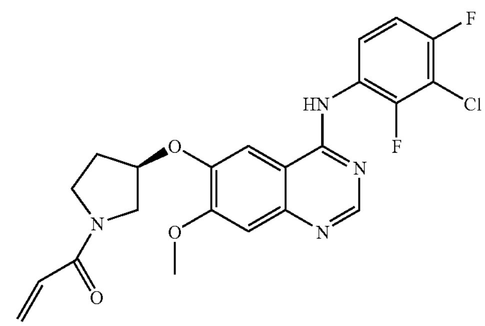 |
| 21 | N-(2-(4-(3-chloro-2,4-difluorophenylamino)-7-methoxyquinazolin-6-yloxy)ethyl)acrylamide | 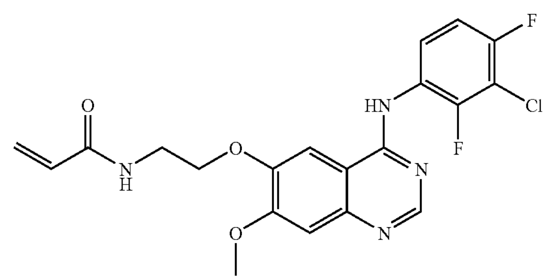 |
| 22 | 1-(3-(7-methoxy-4-((1R)-1-phenylethylamino)quinazolin-6-yloxy)azetidin-1-yl)prop-2-en-1-one | 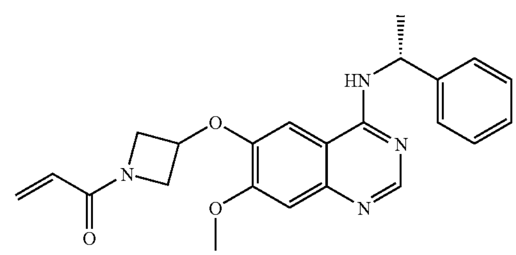 |
| 23 | 1-(3-(4-(3-chloro-2-fluorophenylamino)-7-methoxyquinazolin-6-yloxy)azetidin-1-yl)prop-2-en-1-one | 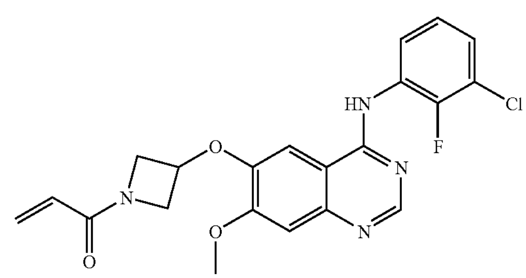 |

TABLE 1-continued

| Example | Compound | Structure |
|---|---|---|
| 24 | 1-(3-(4-(3,4-dichloro-2-fluorophenylamino)-7-methoxyquinazolin-6-yloxy)azetidin-1-yl)prop-2-en-1-one | 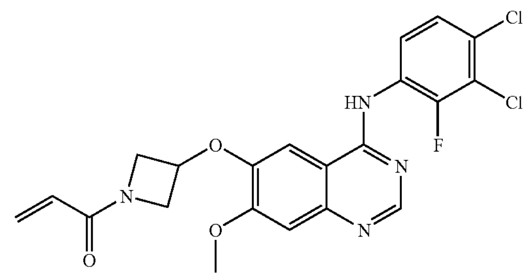 |
| 25 | 1-(3-(4-(3-chloro-4-fluorophenylamino)-7-methoxyquinazolin-6-yloxy)azetidin-1-yl)prop-2-en-1-one | 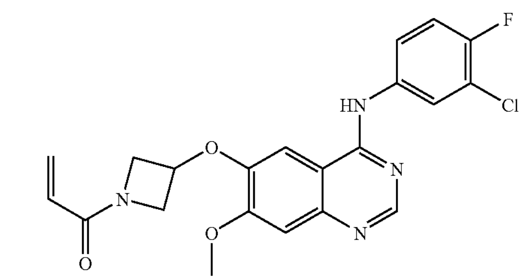 |
| 26 | 1-(3-(4-(3-chlorophenylamino)-7-methoxyquinazolin-6-yloxy)azetidin-1-yl)prop-2-en-1-one | 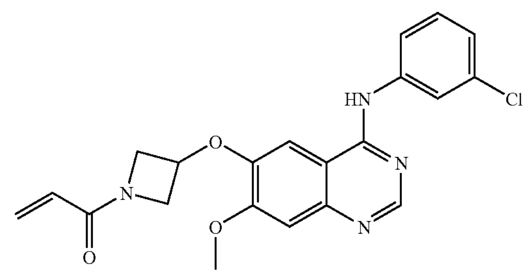 |
| 27 | 3-(6-(1-acryloylazetidin-3-yloxy)-7-methoxyquinazolin-4-ylamino)benzonitrile | 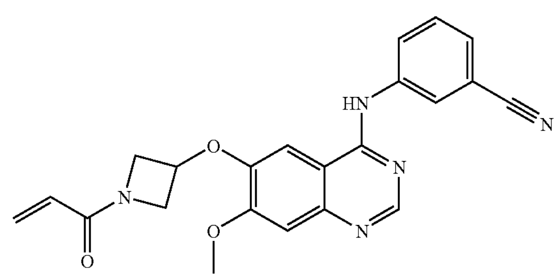 |
| 28 | (E)-4-(3-(4-(3-chloro-2,4-difluorophenylamino)-7-methoxyquinazolin-6-yloxy)azetidin-1-yl)-N-methyl-4-oxobut-2-enamide | 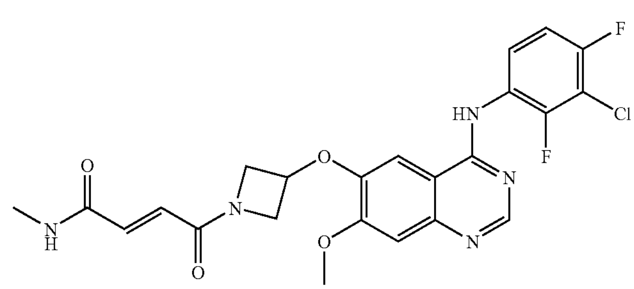 |

TABLE 1-continued

| Example | Compound | Structure |
|---|---|---|
| 29 | 1-(3-(4-(3-chloro-2,4-difluorophenylamino)-7-methoxyquinazolin-6-yloxy)azetidin-1-yl)-2-methylprop-2-en-1-one | 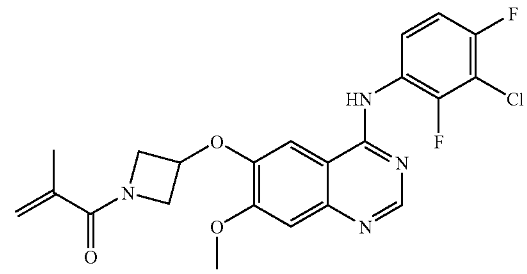 |
| 30 | (Z)-methyl-4-(3-(4-(3-chloro-2-fluorophenylamino)-7-methoxyquinazolin-6-yloxy)azetidin-1-yl)-4-oxobut-2-enoate | 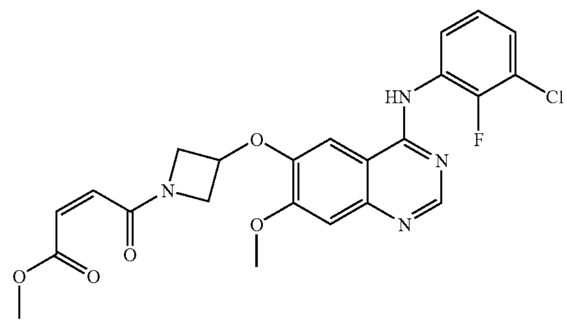 |
| 31 | N-(3-3-(4-(3-chloro-2,4-difluorophenylamino)-7-methoxyquinazolin-6-yloxy)azetidin-1-yl)-3-oxoprop-1-en-2-yl)acetamide | 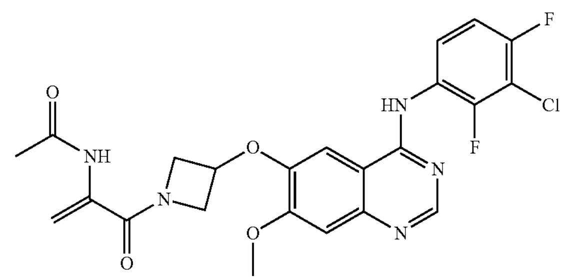 |
| 32 | (Z)-3-chloro-1-(3-(4-(3-chloro-2,4-difluorophenylamino)-7-methoxyquinazolin-6-yloxy)azetidin-1-yl)prop-2-en-1-one | 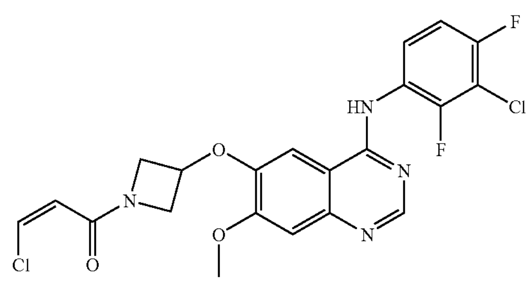 |
| 33 | (E)-3-chloro-1-(3-(4-(3-chloro-2,4-difluorophenylamino)-7-methoxyquinazolin-6-yloxy)azetidin-1-yl)prop-2-en-1-one | 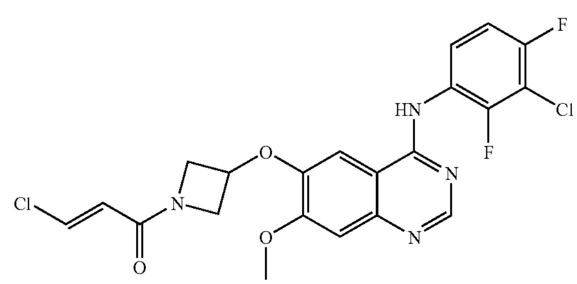 |

TABLE 1-continued

| Example | Compound | Structure |
|---|---|---|
| 34 | 1-(4-(4-(3-chloro-2-fluorophenylamino)-7-methoxyquinazolin-6-yloxy)piperidin-1-yl)prop-2-en-1-one | 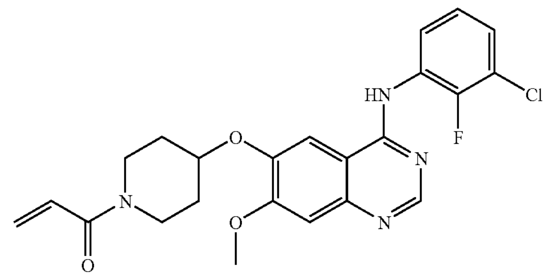 |
| 35 | 1-(4-(7-methoxy-4-((1R)-1-phenylethylamino)quinazolin-6-yloxy)piperidin-1-yl)prop-2-en-1-one | 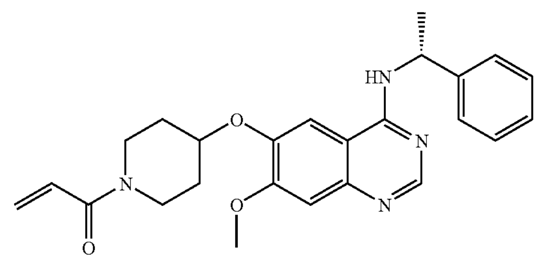 |
| 36 | 1-(4-(4-(3,4-dichloro-2-fluorophenylamino)-7-methoxyquinazolin-6-yloxy)piperidin-1-yl)prop-2-en-1-one | 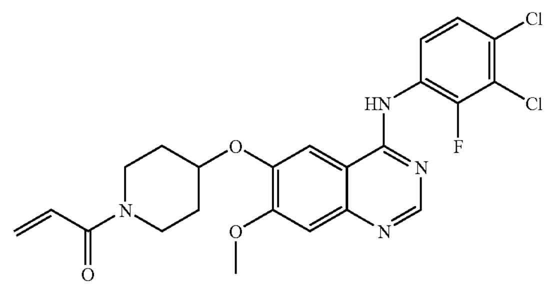 |
| 37 | 1-(4-(4-(3-ethinylphenylamino)-7-methoxyquinazolin-6-yloxy)piperidin-1-yl)prop-2-en-1-one | 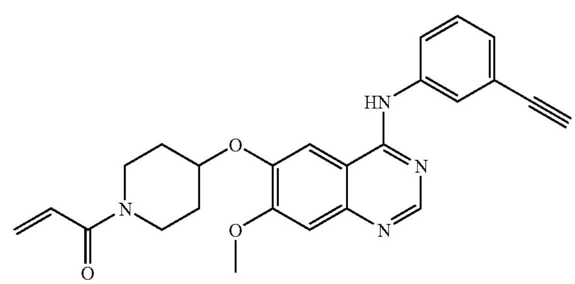 |
| 38 | 1-(4-(4-(4-chloro-2,5-dimethoxyphenylamino)-7-methoxyquinazolin-6-yloxy)piperidin-1-yl)prop-2-en-1-one | 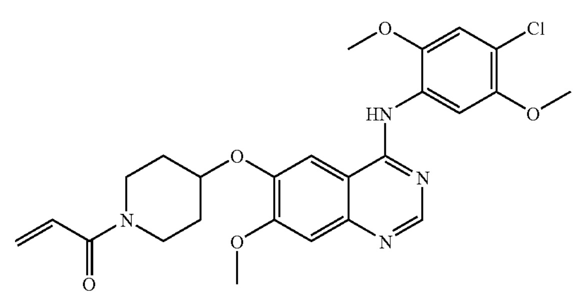 |

TABLE 1-continued

| Example | Compound | Structure |
|---|---|---|
| 39 | 1-(4-(4-(4-bromo-3-methylphenylamino)-7-methoxyquinazolin-6-yloxy)piperidin-1-yl)prop-2-en-1-one | 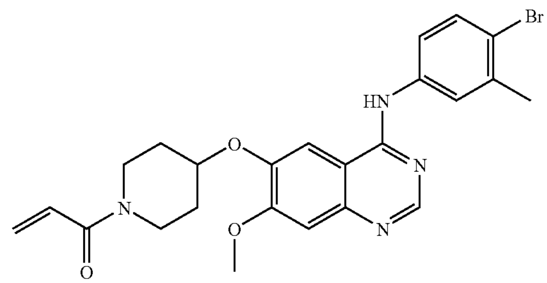 |
| 40 | 1-(4-(4-(4-isopropylphenylamino)-7-methoxyquinazolin-6-yloxy)piperidin-1-yl)prop-2-en-1-one | 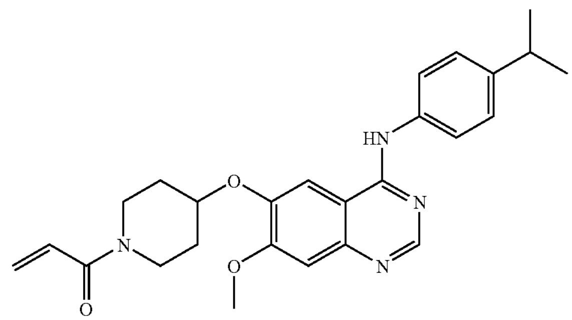 |
| 41 | 1-(4-(4-(m-toluidino)-7-methoxyquinazolin-6-yloxy)piperidin-1-yl)prop-2-en-1-one | 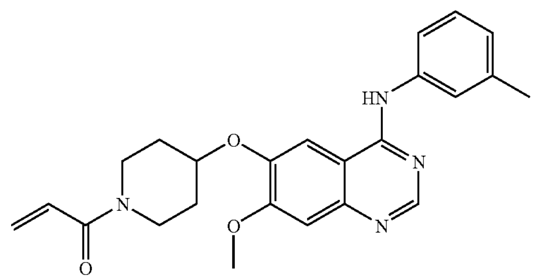 |
| 42 | 1-(4-(4-(3-bromophenylamino)-7-methoxyquinazolin-6-yloxy)piperidin-1-yl)prop-2-en-1-one | 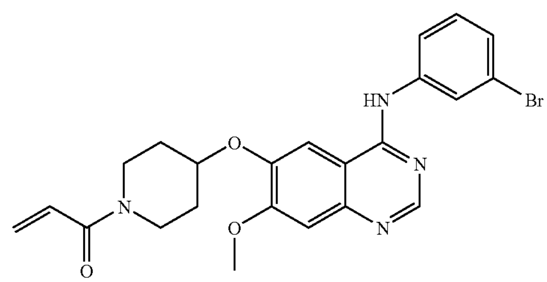 |
| 43 | 1-(4-(4-(3-chlorophenylamino)-7-methoxyquinazolin-6-yloxy)piperidin-1-yl)prop-2-en-1-one | 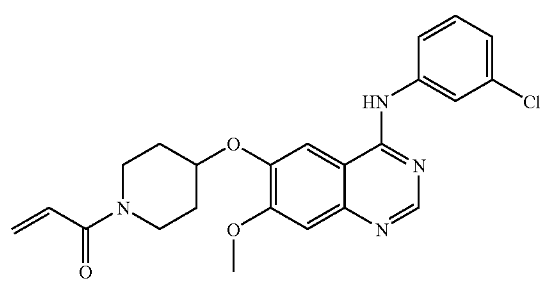 |

TABLE 1-continued

| Example | Compound | Structure |
|---|---|---|
| 44 | 1-(4-(4-(3,4-dichlorophenylamino)-7-methoxyquinazolin-6-yloxy)piperidin-1-yl)prop-2-en-1-one | 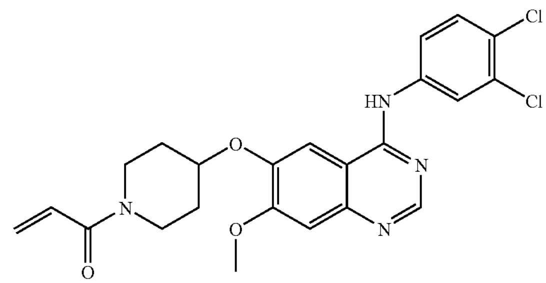 |
| 45 | 1-(4-(7-methoxy-4-(2,3,4-trifluorophenylamino)quinazolin-6-yloxy)piperidin-1-yl)prop-2-en-1-one | 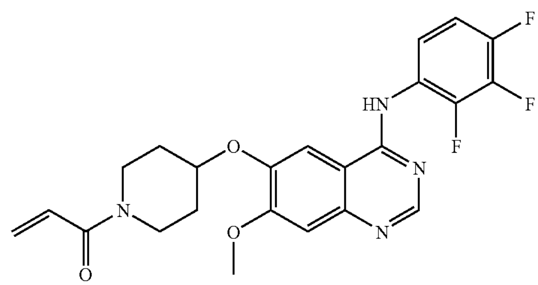 |
| 46 | 1-(4-(4-(4-fluoro-3-methylphenylamino)-7-methoxyquinazolin-6-yloxy)piperidin-1-yl)prop-2-en-1-one | 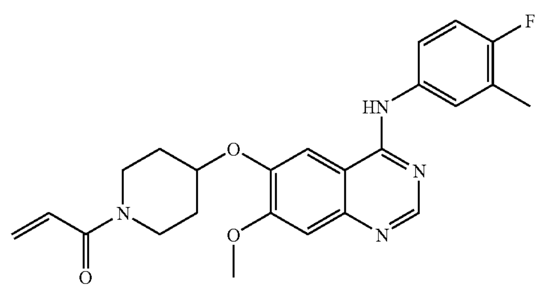 |
| 47 | 1-(4-(4-(3,4-dimethylphenylamino)-7-methoxyquinazolin-6-yloxy)piperidin-1-yl)prop-2-en-1-one | 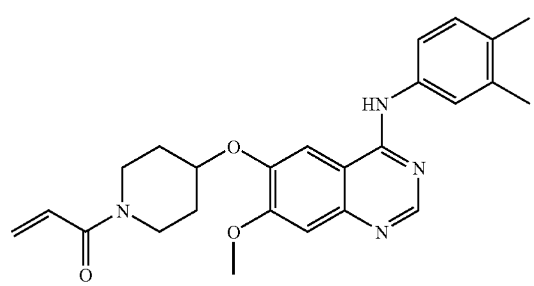 |
| 48 | 1-(4-(7-methoxy-4-(4-phenoxyphenylamino)quinazolin-6-yloxy)piperidin-1-yl)prop-2-en-1-one | 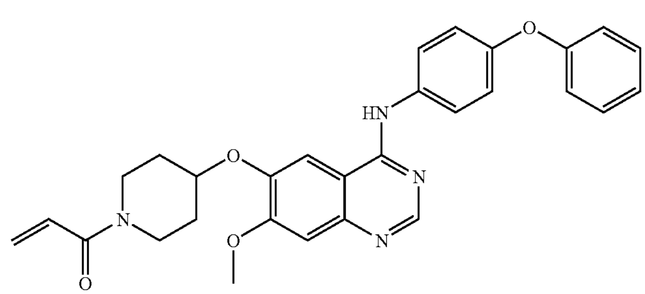 |

TABLE 1-continued

| Example | Compound |
|---|---|
| 49 | 1-(4-(4-(2,3-dihydro-1H-inden-5-ylamino)-7-methoxyquinazolin-6-yloxy)piperidin-1-yl)prop-2-en-1-one |
| 50 | 1-(4-(4-(3,5-dichloro-4-hydroxyphenylamino)-7-methoxyquinazolin-6-yloxy)piperidin-1-yl)prop-2-en-1-one |
| 51 | 1-(4-(4-(4-chloro-3-hydroxyphenylamino)-7-methoxyquinazolin-6-yloxy)piperidin-1-yl)prop-2-en-1-one |
| 52 | 1-(4-(4-(2-chloro-4-hydroxyphenylamino)-7-methoxyquinazolin-6-yloxy)piperidin-1-yl)prop-2-en-1-one |
| 53 | 1-(4-(4-(4-chloro-2-hydroxyphenylamino)-7-methoxyquinazolin-6-yloxy)piperidin-1-yl)prop-2-en-1-one |

TABLE 1-continued

| Example | Compound | Structure |
|---|---|---|
| 54 | 1-(4-(4-(3-chloro-4-(3-fluorobenzyloxy)phenylamino)-7-methoxyquinazolin-6-yloxy)piperidin-1-yl)prop-2-en-1-one | 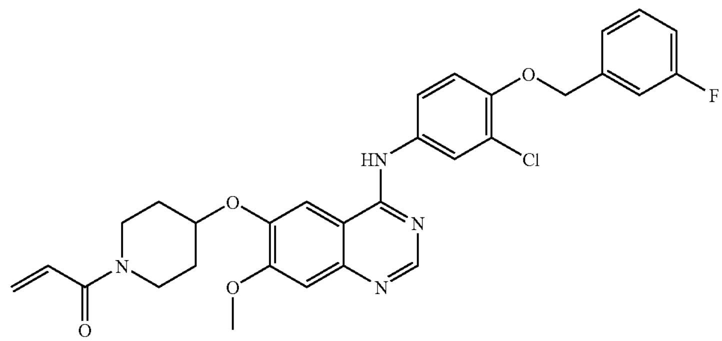 |
| 55 | 1-(4-(4-(3-chloro-4-(pyridin-2-ylmethoxy)phenylamino)-7-methoxyquinazolin-6-yloxy)piperidin-1-yl)prop-2-en-1-one | 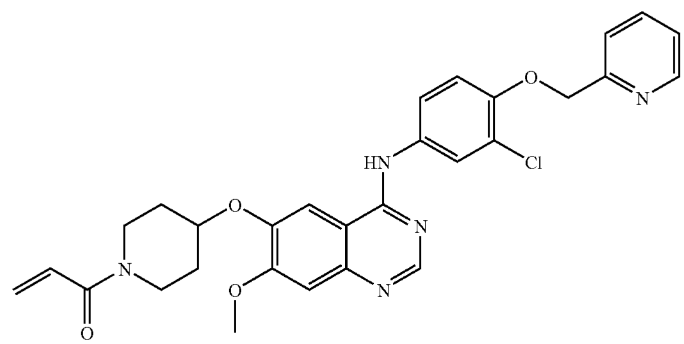 |
| 56 | 3-(6-(1-acryloylpiperidin-4-yloxy)-7-methoxyquinazolin-4-ylamino)benzonitrile | 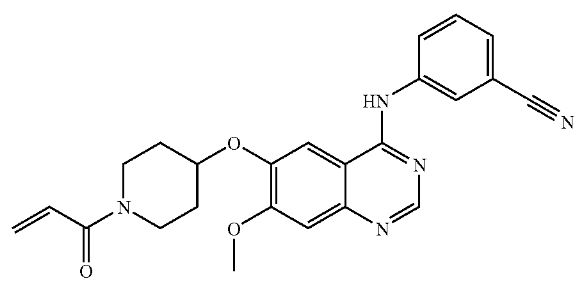 |
| 57 | 1-(4-(4-(3-chloro-4-fluorophenylamino)-7-methoxyquinazolin-6-yloxy)piperidin-1-yl)prop-2-en-1-one | 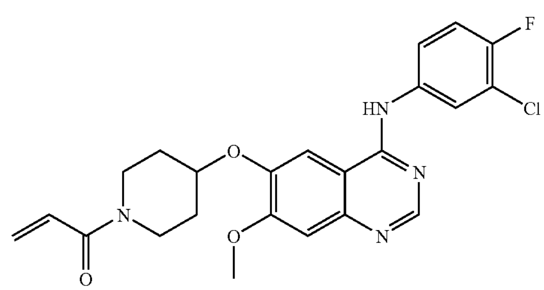 |
| 58 | 1-(4-(4-(3-chloro-4-fluorophenylamino)-7-methoxyquinazolin-6-yloxy)piperidin-1-yl)prop-2-en-1-one | 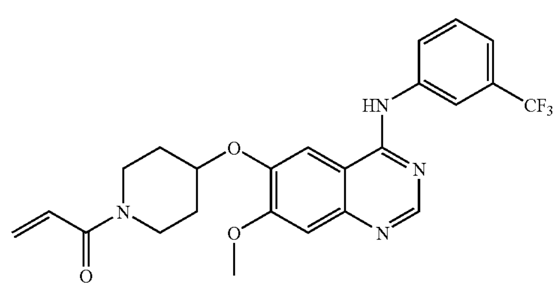 |

TABLE 1-continued

| Example | Compound | Structure |
|---|---|---|
| 59 | 1-(4-(4-(3-chloro-2-methylphenylamino)-7-methoxyquinazolin-6-yloxy)piperidin-1-yl)prop-2-en-1-one | 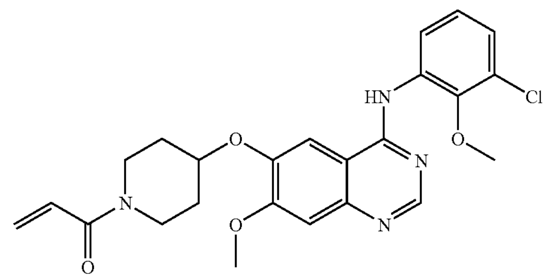 |
| 60 | 1-(4-(4-(4-chloro-3-methylphenylamino)-7-methoxyquinazolin-6-yloxy)piperidin-1-yl)prop-2-en-1-one | 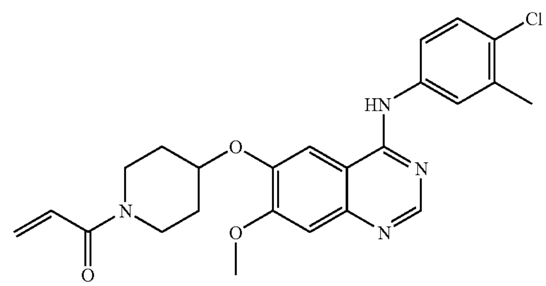 |
| 61 | 1-(4-(4-(4-bromo-3-chlorophenylamino)-7-methoxyquinazolin-6-yloxy)piperidin-1-yl)prop-2-en-1-one | 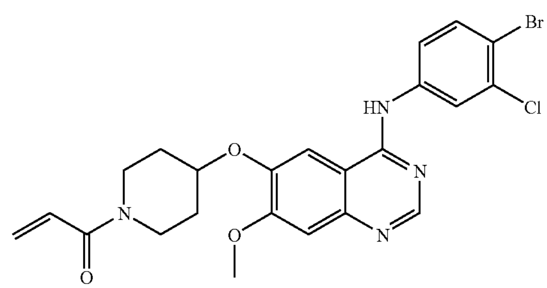 |
| 62 | 1-(4-(4-(4-bromo-3-fluorophenylamino)-7-methoxyquinazolin-6-yloxy)piperidin-1-yl)prop-2-en-1-one | 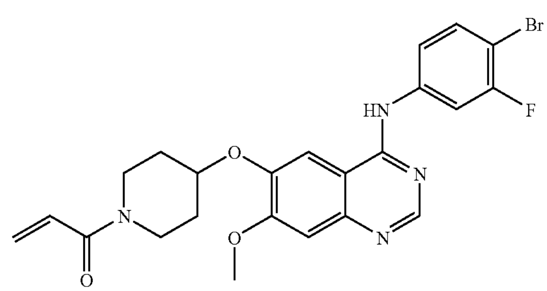 |
| 63 | 1-(4-(4-(3-chloro-2-methylphenylamino)-7-methoxyquinazolin-6-yloxy)piperidin-1-yl)prop-2-en-1-one | 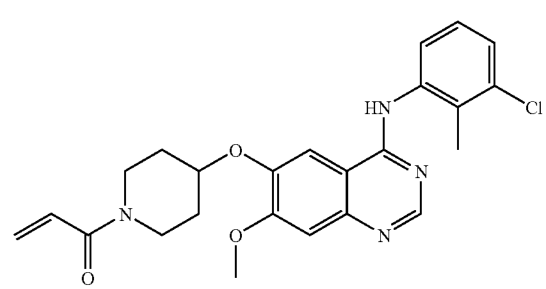 |

TABLE 1-continued

| Example | Compound |
|---|---|
| 64 | 1-(4-(4-(3-(dimethylamino)phenylamino)-7-methoxyquinazolin-6-yloxy)piperidin-1-yl)prop-2-en-1-one |
| 65 | 1-(4-(4-(2-fluoro-3-(trifluoromethyl)phenylamino)-7-methoxyquinazolin-6-yloxy)piperidin-1-yl)prop-2-en-1-one |
| 66 | 5-(6-(1-acryloylpiperidin-4-yloxy)-7-methoxyquinazolin-4-ylamino)-2-fluorobenzonitrile |
| 67 | 5-(6-(1-acryloylpiperidin-4-yloxy)-7-methoxyquinazolin-4-ylamino)-2-chlorobenzonitrile |
| 68 | 1-(4-(7-methoxy-4-(3-(methylthio)phenylamino)quinazolin-6-yloxy)piperidin-1-yl)prop-2-en-1-one |

TABLE 1-continued

| Example | Compound | Structure |
| --- | --- | --- |
| 69 | 1-(4-(4-(2-chlorophenylamino)-7-methoxyquinazolin-6-yloxy)piperidin-1-yl)prop-2-en-1-one | 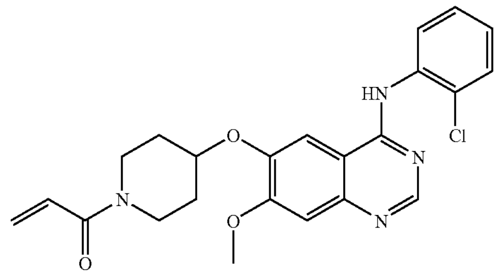 |
| 70 | 1-(4-(4-(4-chlorophenylamino)-7-methoxyquinazolin-6-yloxy)piperidin-1-yl)prop-2-en-1-one | 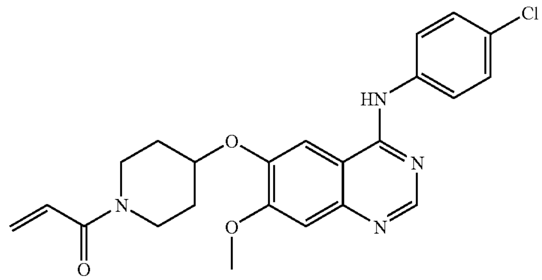 |
| 71 | 1-(4-(4-(3-chloro-2,4-difluorophenylamino)quinazolin-6-yloxy)piperidin-1-yl)prop-2-en-1-one | 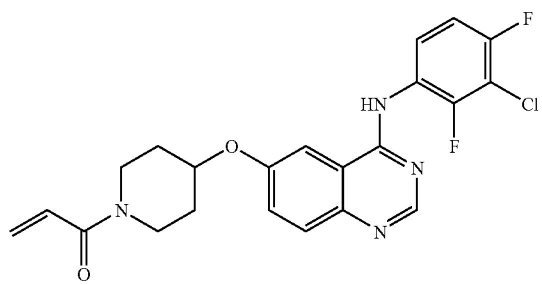 |
| 72 | 1-(4-(4-(3-chlorobenzylamino)-7-methoxyquinazolin-6-yloxy)piperidin-1-yl)prop-2-en-1-one | 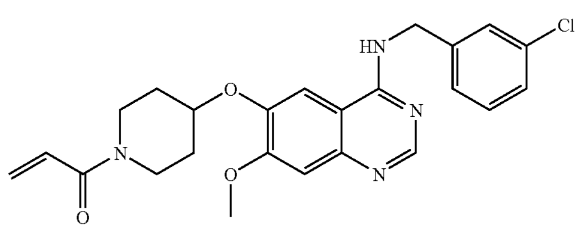 |
| 73 | 1-(4-(7-methoxy-4-(3-vinylphenylamino)quinazolin-6-yloxy)piperidin-1-yl)prop-2-en-1-one | 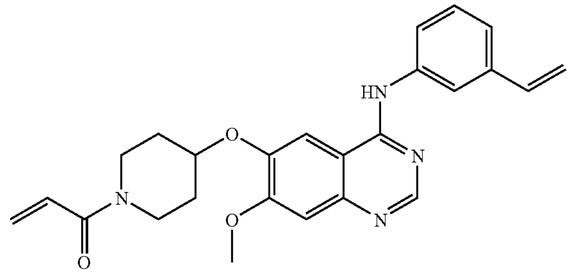 |

TABLE 1-continued

| Example | Compound | Structure |
| --- | --- | --- |
| 74 | 1-(4-(7-methoxy-4-(3-nitrophenylamino)quinazolin-6-yloxy)piperidin-1-yl)prop-2-en-1-one | 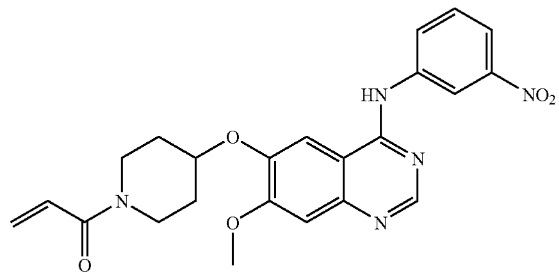 |
| 75 | N-(3-(6-(1-acryloylpiperidin-4-yloxy)-7-quinazolin-4-ylamino)phenyl)acrylamide | 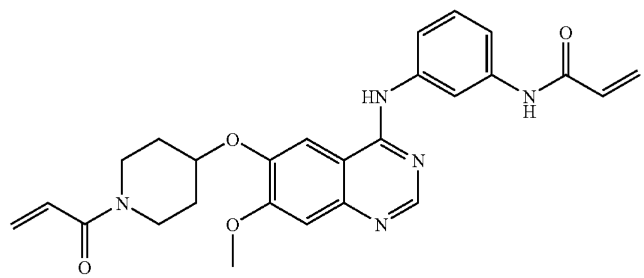 |
| 76 | 1-(4-(4-(3-merchaptophenylamino)-7-methoxyquinazolin-6-yloxy)piperidin-1-yl)prop-2-en-1-one | 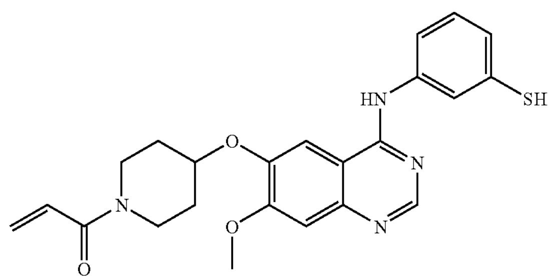 |
| 77 | 1-(4-(4-(3-chloromethyl)phenylamino)-7-methoxyquinazolin-6-yloxy)piperidin-1-yl)prop-2-en-1-one | 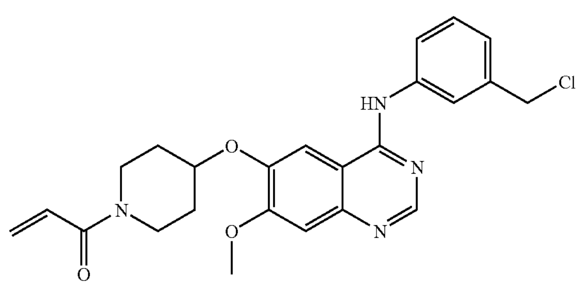 |
| 78 | 1-(4-(4-(3-chloro-4-hydroxyphenylamino)-7-methoxyquinazolin-6-yloxy)piperidin-1-yl)prop-2-en-1-one | 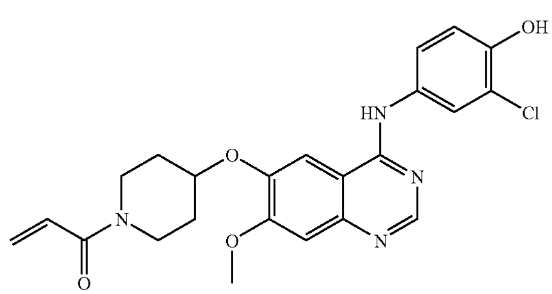 |

TABLE 1-continued

| Example | Compound | Structure |
|---|---|---|
| 79 | 1-(4-(4-(3-fluoro-4-hydroxyphenylamino)-7-methoxyquinazolin-6-yloxy)piperidin-1-yl)prop-2-en-1-one | 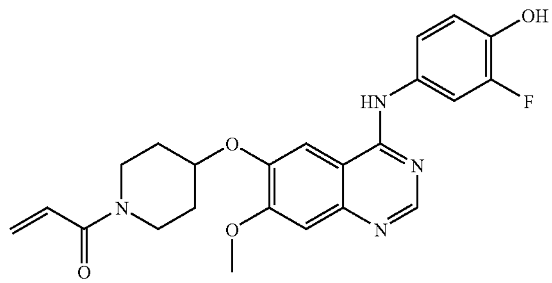 |
| 80 | 1-(4-(4-(3-chloro-2,4-difluorophenylamino)-7-methoxyquinazolin-6-yloxy)piperidin-1-yl)but-2-yn-1-one | 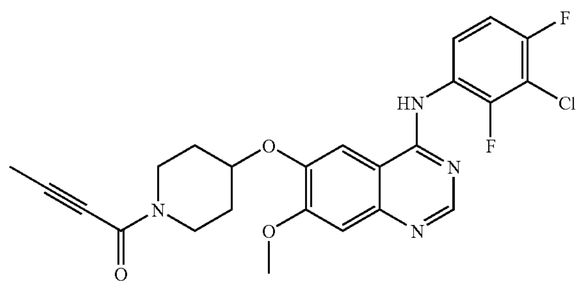 |
| 81 | 1-(4-(4-(3-chloro-2,4-difluorophenylamino)-7-methoxyquinazolin-6-yloxy)piperidin-1-yl)-3-methylbut-2-en-1-one | 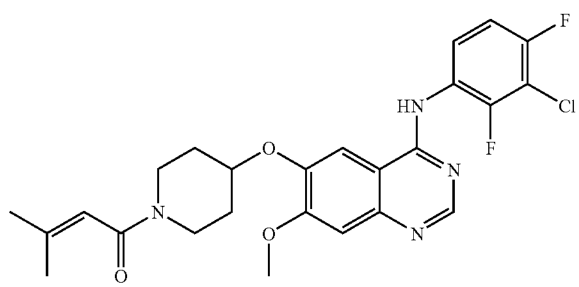 |
| 82 | (E)-4-(4-(4-(3-chloro-2,4-difluorophenylamino)-7-methoxyquinazolin-6-yloxy)piperidin-1-yl)-N-methyl-4-oxobut-2-enamide | 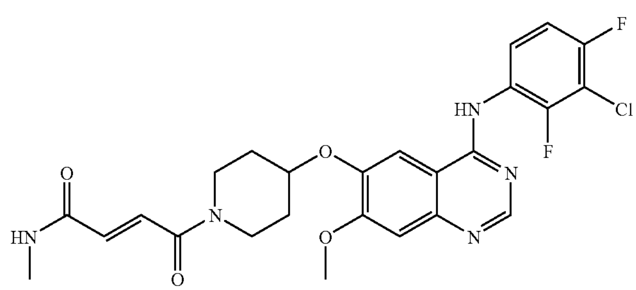 |
| 83 | (Z)-methyl-(4-(4-(3-chloro-2,4-difluorophenylamino)-7-methoxyquinazolin-6-yloxy)piperidin-1-yl)-4-oxobut-2-enoate | 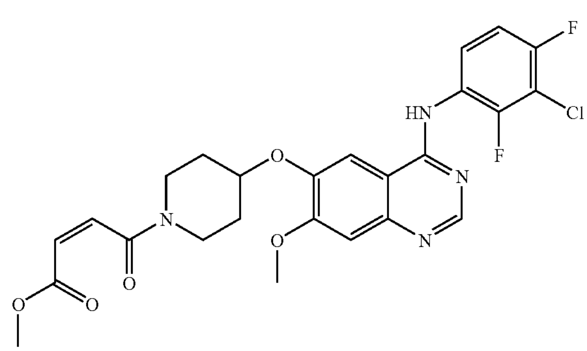 |

TABLE 1-continued

| Example | Compound | Structure |
|---|---|---|
| 84 | (Z)-methyl-(4-(4-(3,4-dichloro-2-difluorophenylamino)-7-methoxyquinazolin-6-yloxy)piperidin-1-yl)-4-oxobut-2-enoate | 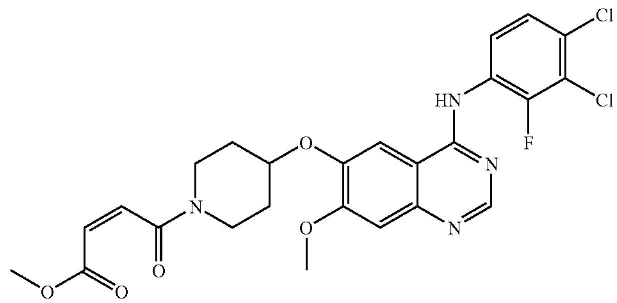 |
| 85 | (Z)-4-(4-(3-chloro-2,4-difluorophenylamino)-7-methoxyquinazolin-6-yloxy)piperidin-1-yl)-4-oxobut-2-enoic acid | 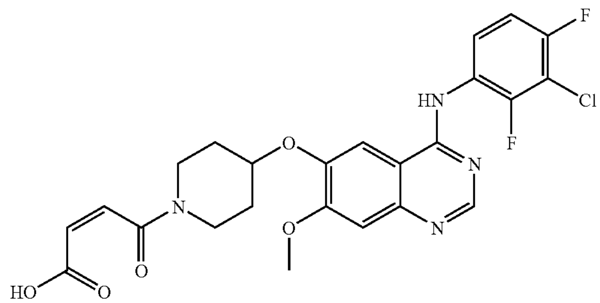 |
| 86 | (Z)-4-(4-(3,4-dichloro-2-fluorophenylamino)-7-methoxyquinazolin-6-yloxy)piperidin-1-yl)-4-oxobut-2-enoic acid | 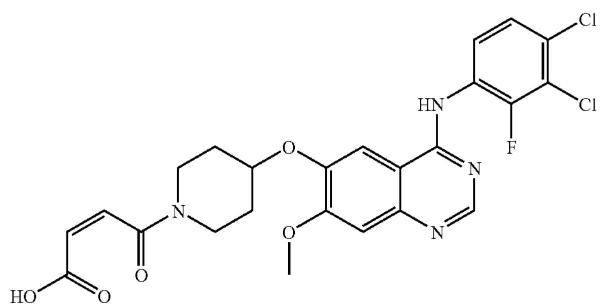 |
| 87 | (E)-4-(4-(4-(3,4-dichloro-2-fluorophenylamino)-7-methoxyquinazolin-6-yloxy)piperidin-1-yl)-4-oxobut-2-enoic acid | 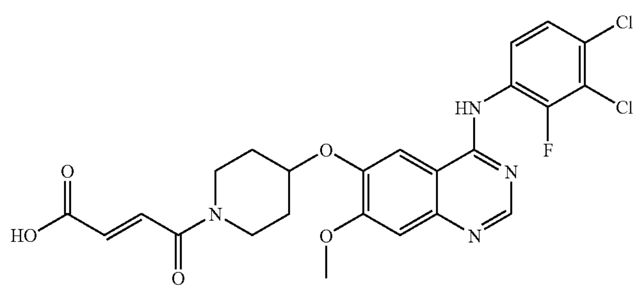 |
| 88 | (E)-4-(4-(3-chloro-2,4-difluorophenylamino)-7-methoxyquinazolin-6-yloxy)piperidin-1-yl)-N-hydroxy-4-oxobut-2-enamide | 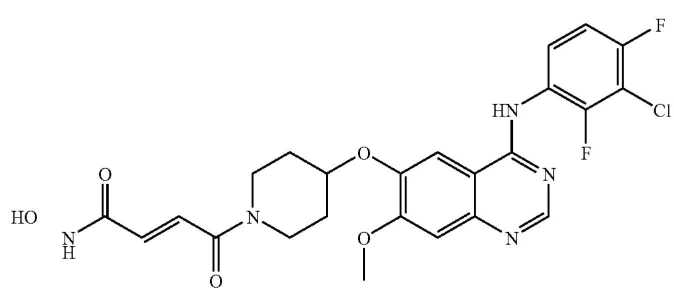 |

TABLE 1-continued

| Example | Compound | Structure |
|---|---|---|
| 89 | (Z)-3-chloro-1-(4-(4-(3,4-dichloro-2-fluorophenylamino)-7-methoxyquinazolin-6-yloxy)piperidin-1-yl)prop-2-en-1-one | 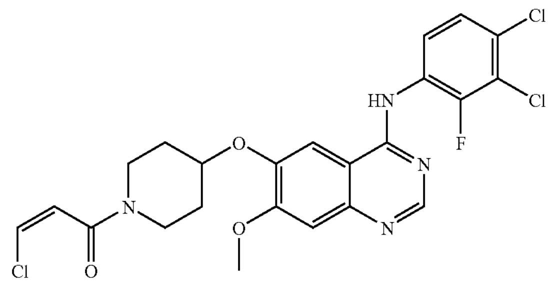 |
| 90 | (E)-3-chloro-1-(4-(4-(3,4-dichloro-2-fluorophenylamino)-7-methoxyquinazolin-6-yloxy)piperidin-1-yl)prop-2-en-1-one | 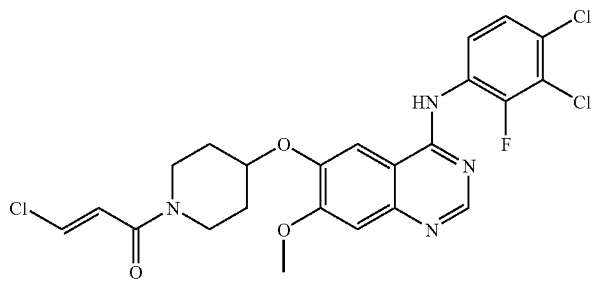 |
| 91 | N-(3-(4-(4-(3,4-dichloro-2-fluorophenylamino)-7-methoxyquinazolin-6-yloxy)piperidin-1-yl)-3-oxoprop-1-en-2-yl)acetamide | 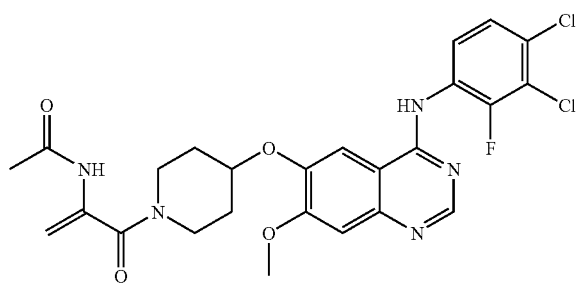 |
| 92 | (E)-1-((3S)-3-(4-(3-chloro-2,4-difluorophenylamino)-7-methoxyquinazolin-6-yloxy)pyrrolidin-1-yl)-4-(dimethylamino)but-2-en-1-one | 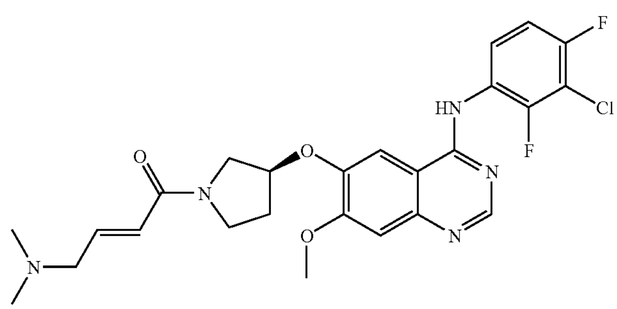 |
| 93 | (E)-1-((3S)-3-(4-(3-chloro-2,4-difluorophenylamino)-7-methoxyquinazolin-6-yloxy)pyrrolidin-1-yl)-4-(dimethylamino)but-2-en-1-one | 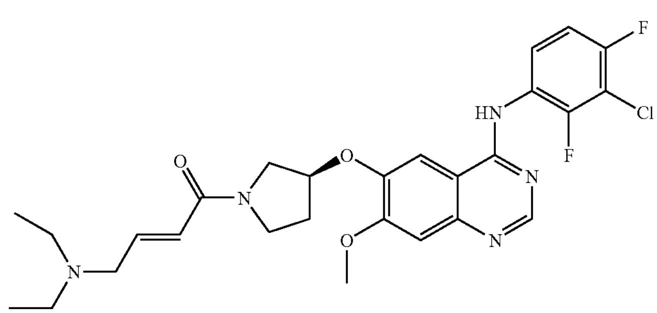 |

TABLE 1-continued

| Example | Compound | Structure |
|---|---|---|
| 94 | (E)-1-((3S)-3-(4-(3-chloro-2,4-difluorophenylamino)-7-methoxyquinazolin-6-yloxy)pyrrolidin-1-yl)-4-morpholinobut-2-en-1-one | 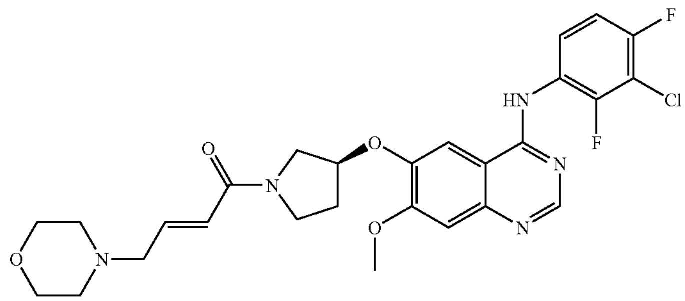 |
| 95 | (E)-1-((3S)-3-(4-(3-chloro-2,4-difluorophenylamino)-7-methoxyquinazolin-6-yloxy)pyrrolidin-1-yl)-4-(pyrrolidin-1-yl)but-2-en-1-one | 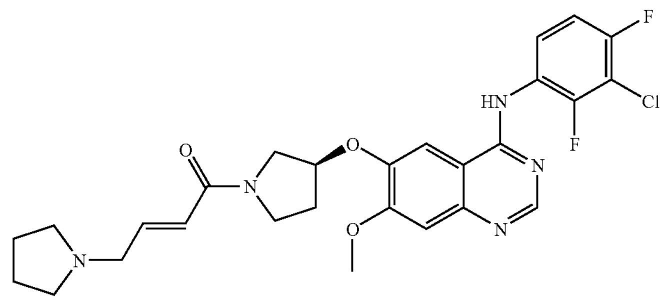 |
| 96 | (E)-1-((3S)-3-(4-(3-chloro-2-fluorophenylamino)-7-methoxyquinazolin-6-yloxy)pyrrolidin-1-yl)-4-(dimethylamino)but-2-en-1-one | 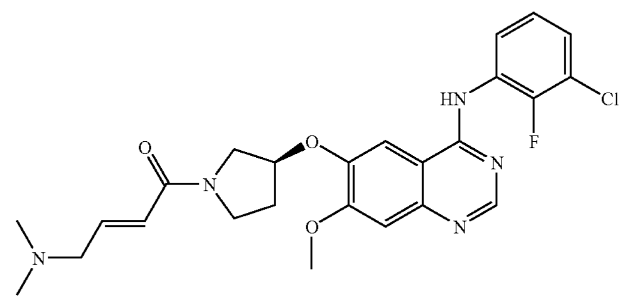 |
| 97 | (E)-1-((3S)-3-(4-(3-chloro-2,4-fluorophenylamino)quinazolin-6-yloxy)pyrrolidin-1-yl)-4-(dimethylamino)but-2-en-1-one | 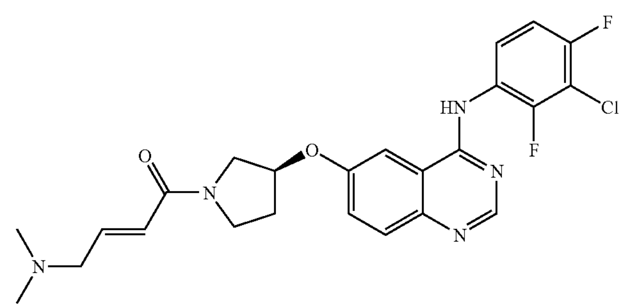 |
| 98 | (E)-1-(4-(4-(3-chloro-2,4-difluorophenylamino)-7-methoxyquinazolin-6-yloxy)piperidin-1-yl)-4-(dimethylamino)but-2-en-1-one | 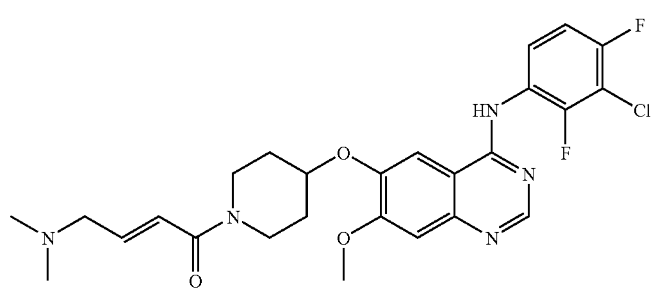 |

TABLE 1-continued

| Example | Compound | Structure |
|---|---|---|
| 99 | (E)-1-(4-(4-(3,4-dichloro-2-difluorophenylamino)-7-methoxyquinazolin-6-yloxy)piperidin-1-yl)-4-(dimethylamino)but-2-en-1-one | 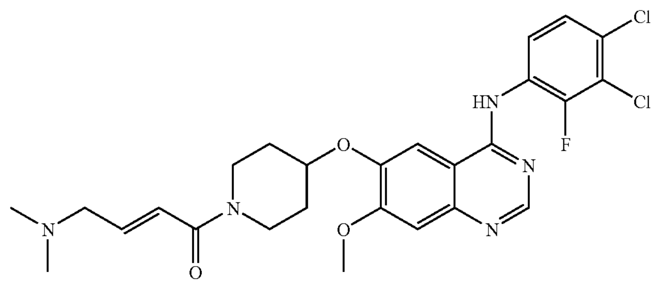 |
| 100 | (E)-1-(4-(4-(3-chloro-2-fluorophenylamino)-7-methoxyquinazolin-6-yloxy)piperidin-1-yl)-4-(dimethylamino)but-2-en-1-one | 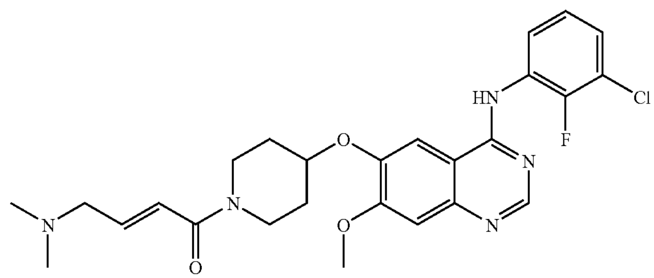 |
| 101 | (E)-1-(3-(4-(3-chloro-2,4-difluorophenylamino)-7-methoxyquinazolin-6-yloxy)azetidin-1-yl)-4-(dimethylamino)but-2-en-1-one | 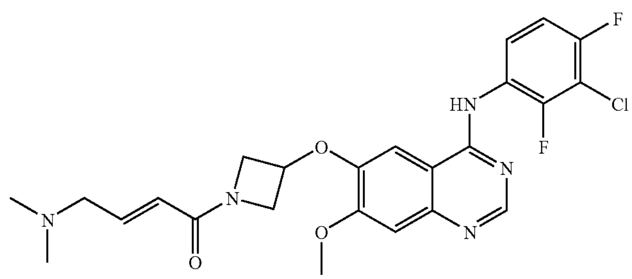 |
| 102 | (E)-1-(3-(4-(3-chloro-2-fluorophenylamino)-7-methoxyquinazolin-6-yloxy)azetidin-1-yl)-4-(dimethylamino)but-2-en-1-one | 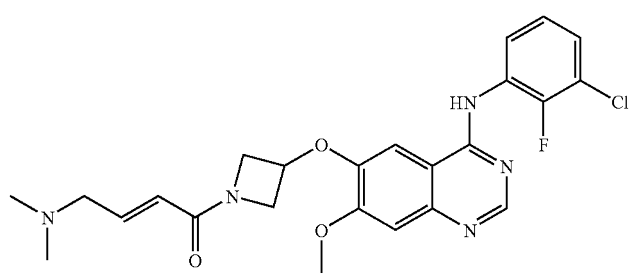 |
| 103 | (E)-N-(2-(4-(3-chloro-2,4-difluorophenylamino)-7-methoxyquinazolin-6-yloxy)ethyl)-4-(dimethylamino)but-2-enamide | 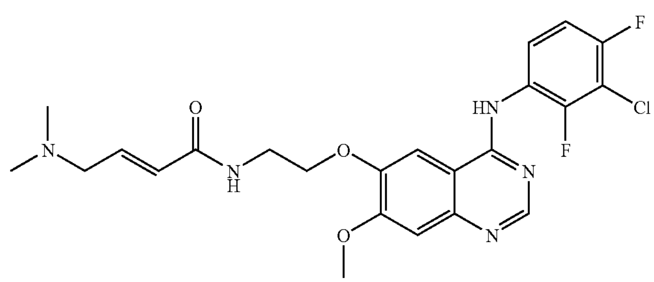 |

TABLE 1-continued

| Example | Compound | Structure |
|---|---|---|
| 104 | 1-(3-(4-(3-chloro-2,4-difluorophenylamino)-7-methoxyquinazolin-6-yloxy)azetidin-1-yl)-2-((dimethylamino)methyl)prop-2-en-1-one | 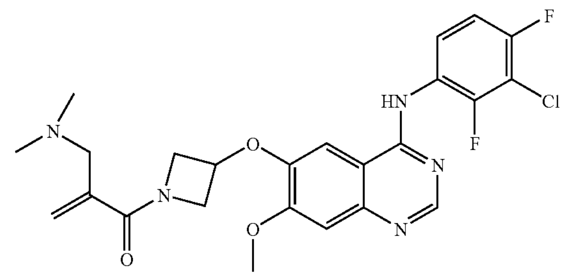 |
| 105 | 1-(3-(4-(3-chloro-2,4-difluorophenylamino)-7-methoxyquinazolin-6-yloxy)azetidin-1-yl)-2-((morpholinomethyl)prop-2-en-1-one | 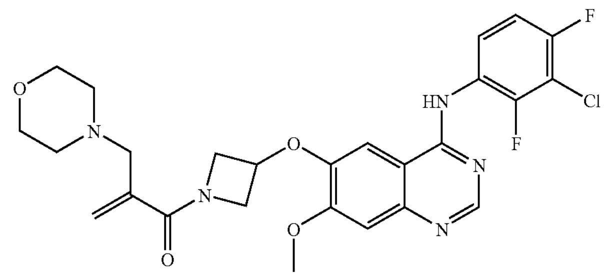 |
| 106 | 1-(3-(4-(3-chloro-2,4-difluorophenylamino)-7-methoxyquinazolin-6-yloxy)azetidin-1-yl)-2-((4-methylpiperazin-1-yl)methyl)prop-2-en-1-one | 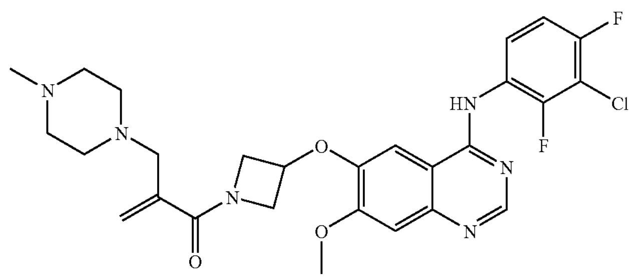 |
| 107 | 1-(3-(4-(3-chloro-2-fluorophenylamino)-7-methoxyquinazolin-6-yloxy)azetidin-1-yl)-2-(piperidin-1-ylmethyl)prop-2-en-1-one | 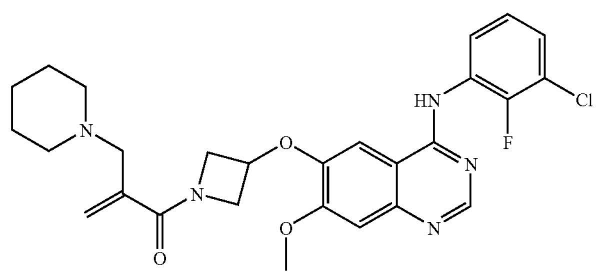 |
| 108 | 1-(3-(4-(3-chloro-2,4-difluorophenylamino)-7-methoxyquinazolin-6-yloxy)azetidin-1-yl)-2-(piperidin-1-ylmethyl)prop-2-en-1-one | 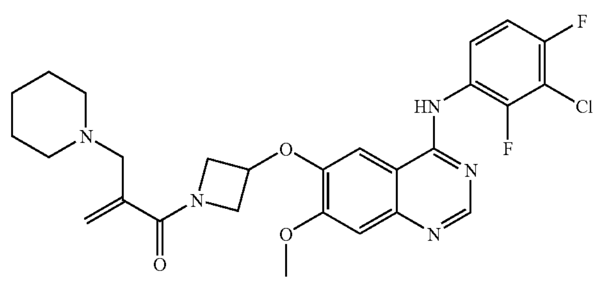 |

TABLE 1-continued

| Example | Compound | Structure |
|---|---|---|
| 109 | 1-(4-(4-(3-chloro-2,4-difluorophenylamino)-7-methoxyquinazolin-6-yloxy)piperidin-1-yl)-2-((dimethylamino)methyl)prop-2-en-1-one | 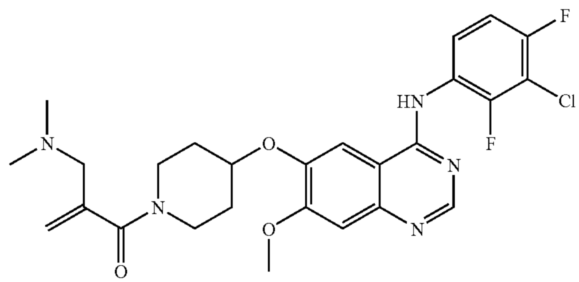 |
| 110 | 1-(4-(4-(3-chloro-2,4-difluorophenylamino)-7-methoxyquinazolin-6-yloxy)piperidin-1-yl)-2-(morpholinomethyl)prop-2-en-1-one | 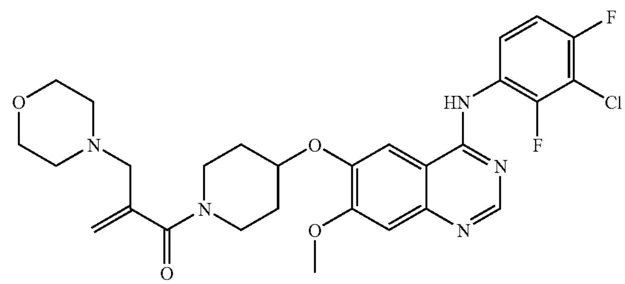 |
| 111 | 1-(4-(4-(3,4-dichloro-2-fluorophenylamino)-7-methoxyquinazolin-6-yloxy)piperidin-1-yl)-2-((dimethylamino)methyl)prop-2-en-1-one | 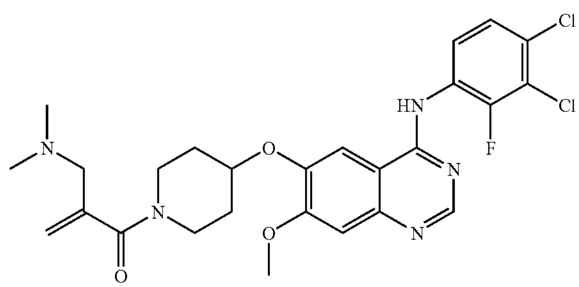 |
| 112 | (Z)-1-(3-(4-(3-chloro-2,4-difluorophenylamino)-7-methoxyquinazolin-6-yloxy)azetidin-1-yl)-4-(dimethylamino)but-2-en-1-one | 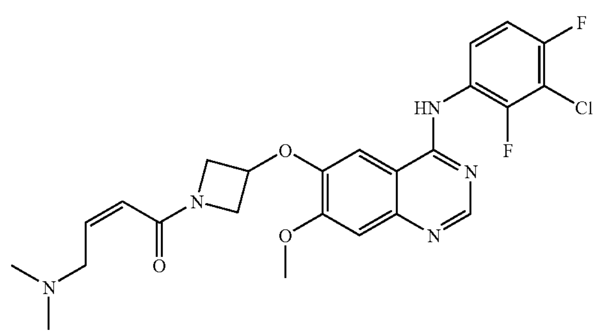 |
| 113 | (Z)-1-(4-(4-(3-chloro-2,4-difluorophenylamino)-7-methoxyquinazolin-6-yloxy)piperidin-1-yl)-2-(dimethylamino)but-2-en-1-one | 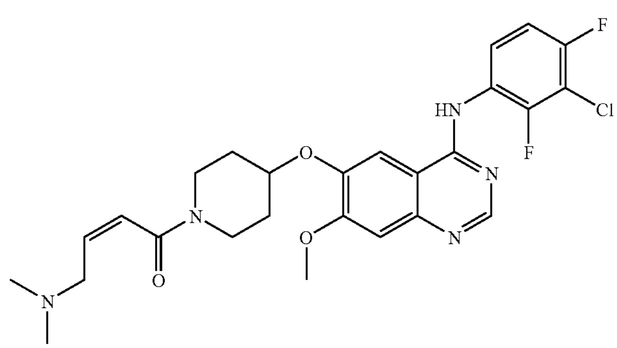 |

TABLE 1-continued

| Example | Compound | Structure |
|---|---|---|
| 114 | 1-(4-(4-(3,4-dichloro-2-fluorophenylamino)-7-methoxyquinazolin-6-yloxy)piperidin-1-yl)-2-(hydroxymethyl)prop-2-en-1-one | 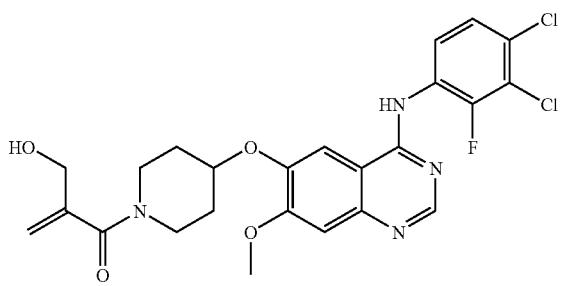 |
| 115 | 1-(3-(4-(3-chloro-2,4-difluorophenylamino)-7-hydroxyquinazolin-6-yloxy)azetidin-1-yl)prop-2-en-1-one | 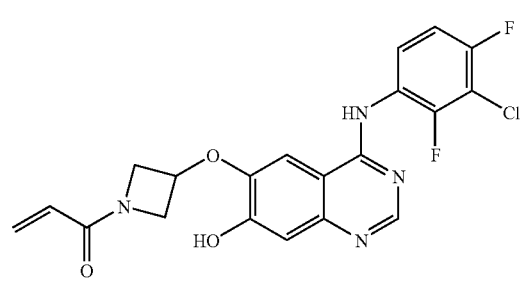 |
| 116 | 1-(3-(4-(3-chloro-2,4-difluorophenylamino)-7-(2-methoxyethoxy)quinazolin-6-yloxy)azetidin-1-yl)prop-2-en-1-one | 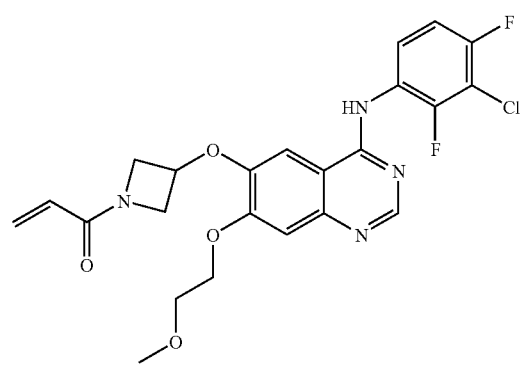 |
| 117 | 1-(4-(4-(3-chloro-2,4-difluorophenylamino)-7-(2-methoxyethoxy)quinazolin-6-yloxy)piperidin-1-yl)prop-2-en-1-one | 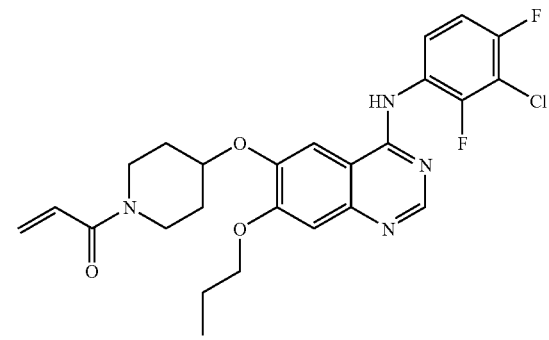 |

TABLE 1-continued

| Example | Compound | Structure |
|---|---|---|
| 118 | 1-(4-(4-(3-chloro-2,4-difluorophenylamino)-7-(3-morpholinopropoxy)quinazolin-6-yloxy)piperidin-1-yl)prop-2-en-1-one | 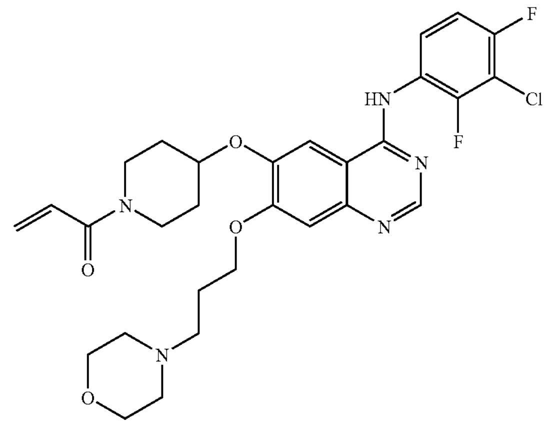 |
| 119 | (2S,4S)-methyl-1-acryloyl-4-(4-(3-chloro-2,4-difluorophenylamino)-7-methoxyquinazolin-6-yloxy)piperidin-2-carboxylate | 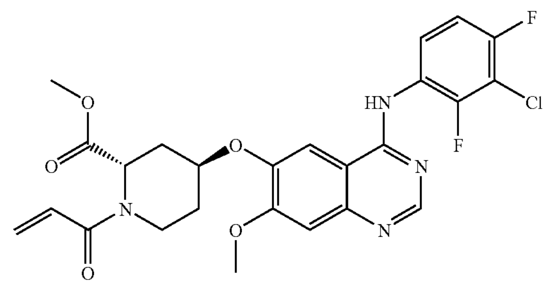 |
| 120 | (2S,4S)-1-acryloyl-4-(4-(3-chloro-2,4-difluorophenylamino)-7-methoxyquinazolin-6-yloxy)piperidin-2-carboxamide | 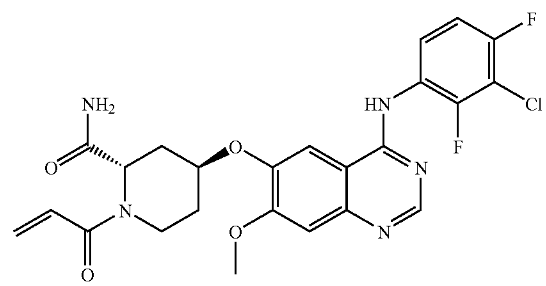 |
| 121 | (2S,4S)-1-acryloyl-4-(4-(3-chloro-2,4-difluorophenylamino)-7-methoxyquinazolin-6-yloxy)-N-methylpiperidin-2-carboxamide | 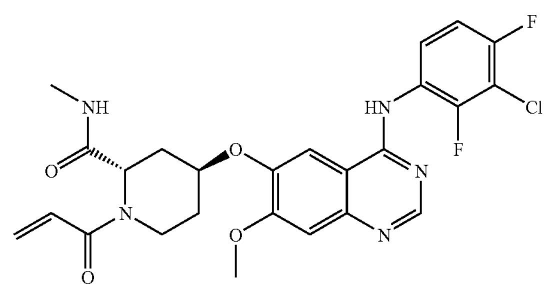 |
| 122 | (2S,4S)-1-acryloyl-4-(4-(3-chloro-2,4-difluorophenylamino)-7-methoxyquinazolin-6-yloxy)-N-ethylpiperidin-2-carboxamide | 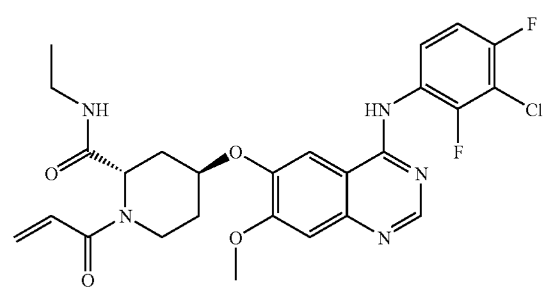 |

TABLE 1-continued

| Example | Compound | Structure |
|---|---|---|
| 123 | (2S,4S)-1-acryloyl-4-(4-(3-chloro-2,4-difluorophenylamino)-7-methoxyquinazolin-6-yloxy)-N-propylpiperidin-2-carboxamide | 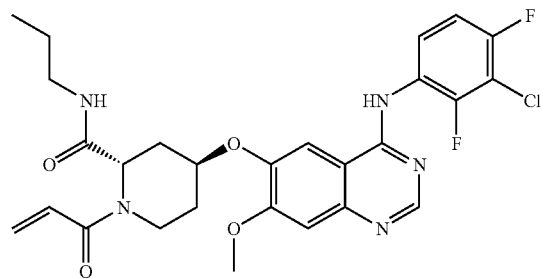 |
| 124 | (2S,4S)-1-acryloyl-4-(4-(3-chloro-2,4-difluorophenylamino)-7-methoxyquinazolin-6-yloxy)-N-isopropylpiperidin-2-carboxamide | 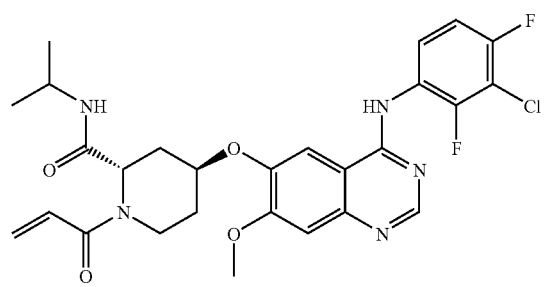 |
| 125 | (2S,4S)-1-acryloyl-4-(4-(3-chloro-2,4-difluorophenylamino)-7-methoxyquinazolin-6-yloxy)-N-hydroxypiperidin-2-carboxamide | 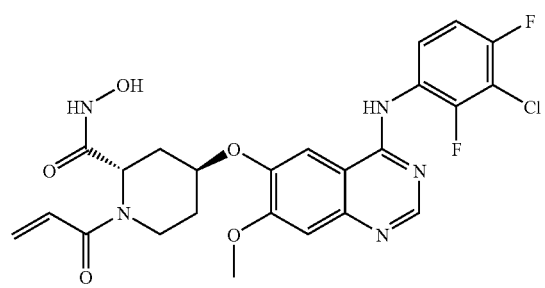 |
| 126 | (2S,4S)-1-acryloyl-4-(4-(3-chloro-2,4-difluorophenylamino)-7-methoxyquinazolin-6-yloxy)-N-(2-hydroxyethyl)piperidin-2-carboxamide | 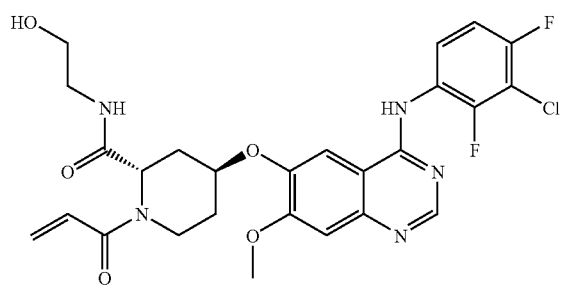 |
| 127 | (2S,4S)-1-acryloyl-4-(4-(3-chloro-2,4-difluorophenylamino)-7-methoxyquinazolin-6-yloxy)-N-(2-methoxyethyl)piperidin-2-carboxamide | 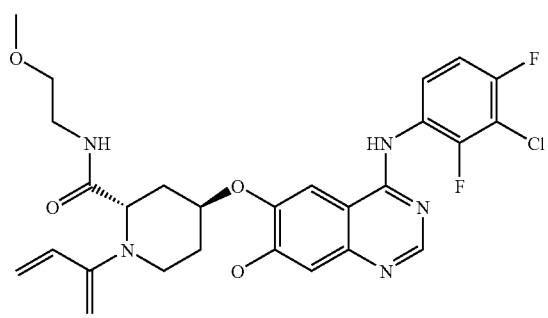 |

TABLE 1-continued

| Example | Compound | Structure |
|---|---|---|
| 128 | (2S,4S)-1-acryloyl-4-(4-(3-chloro-2,4-difluorophenylamino)-7-methoxyquinazolin-6-yloxy)-N-(2-(methylthio)ethyl)piperidin-2-carboxamide | 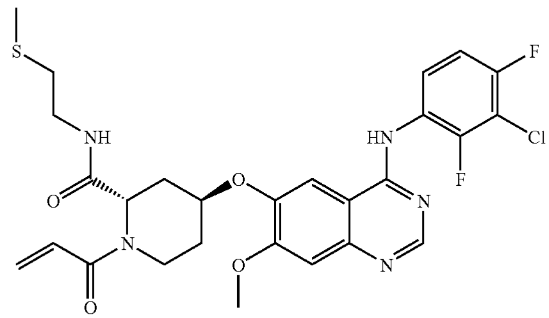 |
| 129 | (2S,4S)-1-acryloyl-4-(4-(3-chloro-2,4-difluorophenylamino)-7-methoxyquinazolin-6-yloxy)-N-(2-(methylsulphonyl)ethyl)piperidin-2-carboxamide | 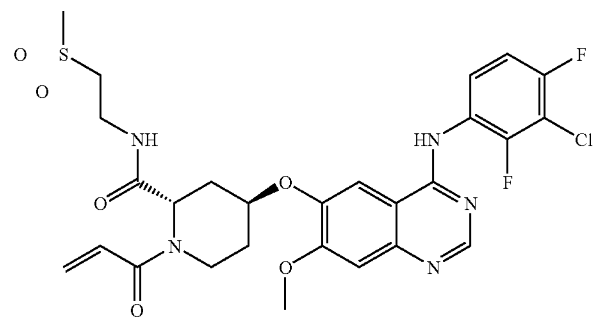 |
| 130 | (2S,4S)-1-acryloyl-4-(4-(3-chloro-2,4-difluorophenylamino)-7-methoxyquinazolin-6-yloxy)-N-(2-(dimethylamino)ethyl)piperidin-2-carboxamide | 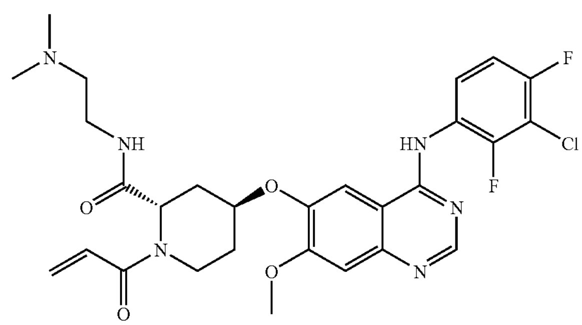 |
| 131 | (2S,4S)-1-acryloyl-4-(4-(3-chloro-2,4-difluorophenylamino)-7-methoxyquinazolin-6-yloxy)-N-(3-hydroxypropyl)piperidin-2-carboxamide | 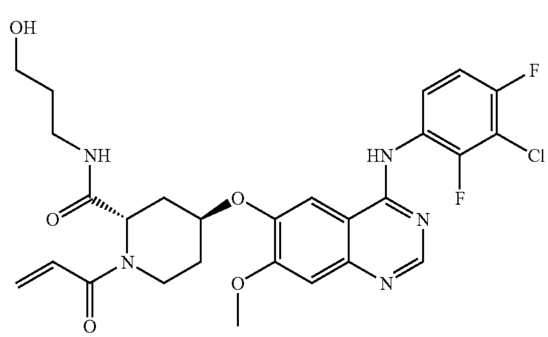 |

TABLE 1-continued

| Example | Compound | Structure |
|---|---|---|
| 132 | (2S,4S)-1-acryloyl-4-(4-(3-chloro-2,4-difluorophenylamino)-7-methoxyquinazolin-6-yloxy)-N-(2-morpholinoethyl)piperidin-2-carboxamide | 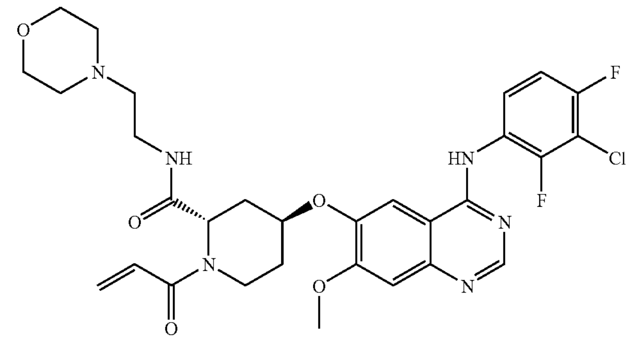 |
| 133 | (2R,4R)-methyl-1-acryloyl-4-(4-(3-chloro-2,4-difluorophenylamino)-7-methoxyquinazolin-6-yloxy)piperidin-2-carboxamide | 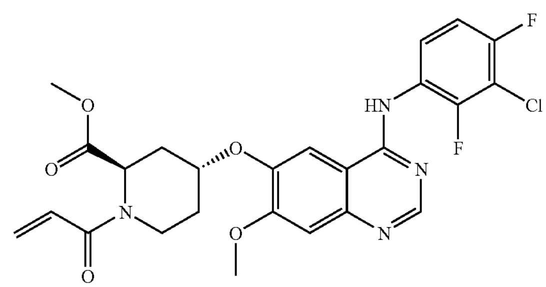 |
| 134 | (2R,4R)-1-acryloyl-4-(4-(3-chloro-2,4-difluorophenylamino)-7-methoxyquinazolin-6-yloxy)piperidin-2-carboxyl acid | 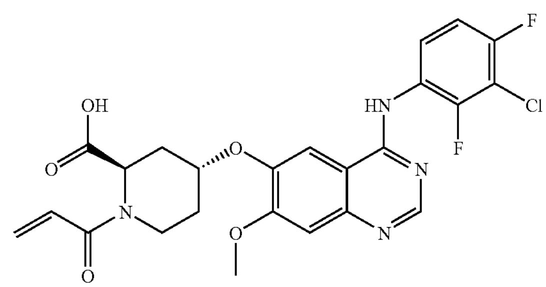 |
| 135 | (2R,4R)-1-acryloyl-4-(4-(3-chloro-2,4-difluorophenylamino)-7-methoxyquinazolin-6-yloxy)piperidin-2-carboxamide | 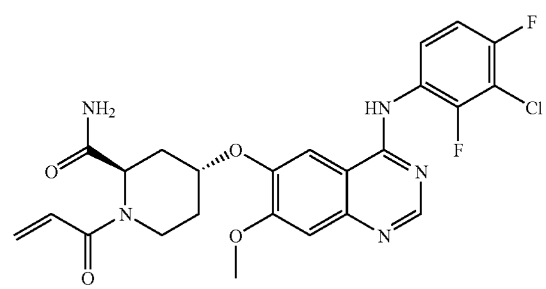 |
| 136 | (2R,4R)-1-acryloyl-4-(4-(3-chloro-2,4-difluorophenylamino)-7-methoxyquinazolin-6-yloxy)-N-methylpiperidin-2-carboxamide | 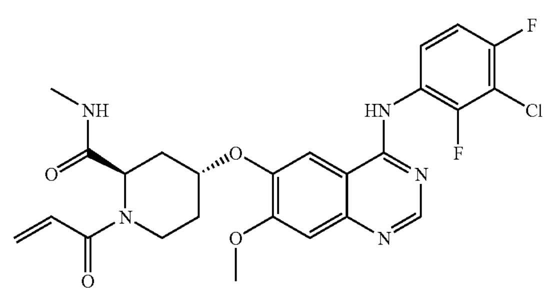 |

TABLE 1-continued

| Example | Compound | Structure |
|---|---|---|
| 137 | (2R,4R)-1-acryloyl-4-(4-(3-chloro-2,4-difluorophenylamino)-7-methoxyquinazolin-6-yloxy)-N-hydroxypiperidin-2-carboxamide | 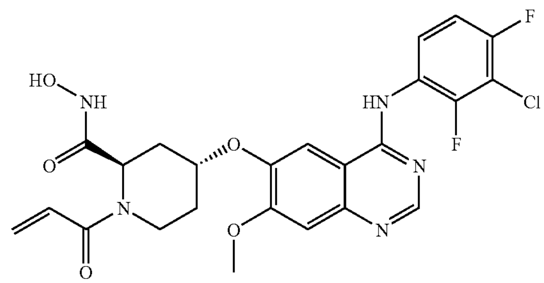 |
| 138 | (2R,4R)-1-acryloyl-4-(4-(3-chloro-2,4-difluorophenylamino)-7-methoxyquinazolin-6-yloxy)-N-(2-(methylsulphonyl)ethyl)piperidin-2-carboxamide | 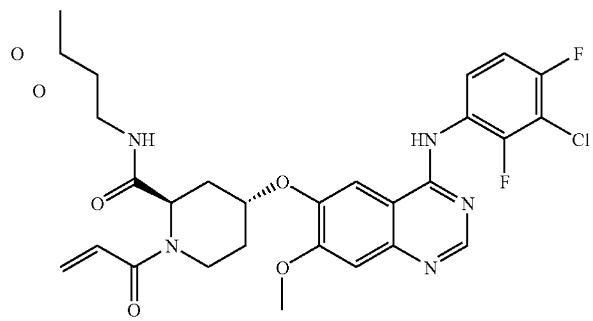 |
| 139 | (2R,4R)-1-acryloyl-4-(4-(3,4-dichloro-2-fluorophenylamino)-7-methoxyquinazolin-6-yloxy)piperidin-2-carboxamide | 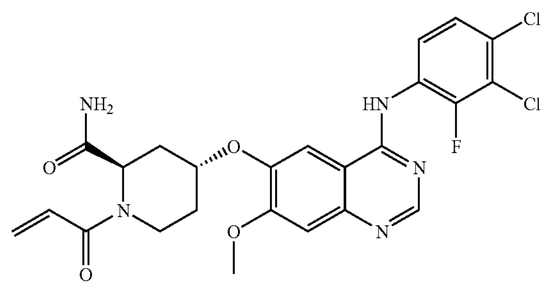 |
| 140 | (2R,4R)-1-acryloyl-4-(4-(4-bromo-2-fluorophenylamino)-7-methoxyquinazolin-6-yloxy)piperidin-2-carboxamide | 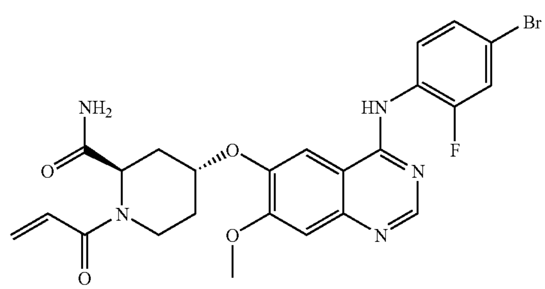 |

Preparation Example 1

Tablets for oral administration comprising each of the compounds of formula (I) obtained in Examples 1 to 140 as an active ingredient were prepared based on the recipes of Table 2.

TABLE 2

| Ingredient | Amount/tablet |
|---|---|
| Active Ingredient | 100 mg |
| Corn Starch | 80 mg |
| Lactose | 80 mg |
| Magnesium Stearate | 5 mg |

Preparation Example 2

Hard gelatin capsules for oral administration comprising each of the compounds of formula (I) obtained in Examples 1 to 140 as an active ingredient were prepared based on the recipes of Table 3.

TABLE 3

| Ingredient | Amount/tablet |
|---|---|
| Active Ingredient | 100 mg |
| Corn Starch | 40 mg |
| Lactose | 80 mg |

TABLE 3-continued

| Ingredient | Amount/tablet |
| --- | --- |
| Crystalline Cellulose | 80 mg |
| Magnesium Stearate | 5 mg |

Preparation Example 3

Injection formulations comprising each of the compounds of formula (I) obtained in Examples 1 to 140 as an active ingredient were prepared based on the recipes of Table 4, wherein when a salt of the compound of formula (I) was used, the pH value was not manipulated.

TABLE 4

| Ingredient | Amount/tablet |
| --- | --- |
| Active Ingredient | 20 mg |
| 5% Glucose | 10 ml |
| HCl (1N) | adjusted to pH 4 |

Preparation Example 4

Injection formulations comprising each of the compounds of formula (I) obtained in Examples 1 to 140 as an active ingredient were prepared based on the recipes of Table 5.

TABLE 5

| Ingredient | Amount/tablet |
| --- | --- |
| Active Ingredient | 20 mg |
| Polyethylene Glycol 400 | 2 ml |
| Sterile Water | 8 ml |

Test Example 1

Inhibition of EGFR Enzyme

10 μl of an EGFR (EGFR type 1 kinase, Upstate, 10 ng/μl) was added to each well of a 96-well plate. As an EGFR inhibitor, 10 μl of a serially diluted solution of each of the compounds obtained in Examples 1 to 140, Iressa (Astrazeneca) and Lapatinib (GlaxoSmithKline) was added to each well, and the plate was incubated at room temperature for 10 mins. 10 μl of Poly (Glu, Tyr) 4:1 (Sigma, 10 ng/ml) and 10 μl of ATP (50 μM) were successively added thereto to initiate a kinase reaction, and the resulting mixture was incubated at room temperature for 1 hour. 10 μl of 100 mM EDTA was added to each well and stirred for 5 mins to terminate the kinase reaction. 10 μl of 10× anti-phosphotyrosine antibody (Pan Vera), 10 μl of 10×PTK (protein tyrosine kinase) green tracer (Pan Vera) and 30 μl of FP (fluorescence polarization) diluted buffer were added to the reacted mixture, followed by incubating in dark at room temperature for 30 mins. The FP value of each well was determined with VICTORIII fluorescence meter (Perkin Elmer) at 488 nm (excitation filter) and 535 nm (emission filter), and $IC_{50}$, the concentration at which 50% inhibition was observed, was determined, wherein the maximum (0% inhibition) value was set at the polarized light value measured for the well untreated with an EGFR inhibitor and the minimum value corresponded to 100% inhibition. The calculation and analysis of $IC_{50}$ were carried out by using Microsoft Excel. The results are shown in Table 7.

Test Example 2

Inhibition of EGFR Mutant Enzyme (T790M)

The procedure of Test Example 1 was repeated except that 10 μl of T790M enzyme (EGFR T790M kinase, Upstate) was employed instead of 10 μl of the EGFR. The results are shown in Table 7.

Test Example 3

Test of Cancer Cell Growth Inhibition

A skin cancer cell line, A431 (ATCC: CRL-1555), a breast cancer cell line, SK-Br3 (ATCC: HTB-30), and a colon/rectal cancer cell line, SW-620 (ATCC: CCL-227), were used to test the degrees of the inventive compounds in inhibiting the cancer cell growth using a culture medium, DMEM (Dulbecco's Modified Eagle's Medium) having 4.5 g/l of glucose and 1.5 g/l of sodium bicarbonate added and supplemented with 10% FBS (fetal bovine serum). In addition, a lung cancer cell line, H1975 (ATCC: CRL-5908), was incubated in an RPMI medium containing 1% sodium pyruvate and 10% FBS.

The cancer cell lines stored in a liquid nitrogen tank were each quickly thawed at 37° C., and centrifuged to remove the medium. The resulting cell pellet was mixed with a culture medium, incubated in a culture flask at 37° C. under 5% $CO_2$ for 2 to 3 days, and the medium was removed. The remaining cells were washed with DPBS (Dulbecco's Phosphate Buffered Saline) and separated from the flask by using Tripsin-EDTA. The separated cells were diluted with a culture medium to a concentration of 100,000 A431 or SW-620 cells/ml, except that in case of SK-Br3, the dilution was carried out to 200,000 cells/ml. 100 μl of the diluted cell solution was added to each well of a 96-well plate, and incubated at 37° C. under 5% $CO_2$ for 1 day.

The compounds obtained in Examples 1 to 140 as well as the conventional EGFR inhibitors, Iressa and Lapatinib, were each dissolved in 99.5% DMSO to a concentration of 25 mM. In case that the test compound was not soluble in DMSO, a small amount of 1% HCl was added thereto and treated in a 40° C. water bath for 30 mins until a complete dissolution was attained. The test compound solution was diluted with a culture medium to a final concentration of 100 μM, and then diluted 10 times serially to $10^{-6}$ μM (a final concentration of DMSO was less than 1%). The medium was removed from each well of the 96-well plate.

100 μl of a test compound solution was added to each well holding the cultured cells, and the plate was incubated at 37° C. under 5% $CO_2$ for 72 hours. After removing the medium from the plate, 50 μl of 10% trichloroacetic acid was added to each well, and the plate was kept at 4° C. for 1 hour to fix the cells to the bottom of the plate. The added trichloroacetic acid was removed from each well, the plate was dried, 100 μl of an SRB (Sulforhodamine-B) dye solution was added thereto, and the resulting mixture was reacted for 10 mins. The SRB dye solution was prepared by dissolving SRB in 1% acetic acid to a concentration of 0.4%. After removing the dye solution, the plate was washed with water, and dried. When the dye solution was not effectively removed by water, 1% acetic acid was used. 150 μl of 10 mM trisma base was added to each well, and the absorbance at 540 nm was determined with a microplate reader.

In case of H1975, the cells were diluted with a culture medium to a concentration of 50,000 cells/ml. 100 μl of the diluted cell solution was added to each well of a 96-well plate, and, after 1 day, was washed with a mixture of RPMI, 0.1%

FBS and 1% penicillin-streptomycin (PS), followed by replacement of the medium. The plate was allowed to be kept overnight and be treated to various concentrations under the same medium condition for 48 hrs. Similarly to an MTT assay, 15 μl of a celltiter one shot solution (Promega) was added to each well, which was incubated for 2 to 3 hrs, and, then, the absorbance at 490 nm was determined.

$IC_{50}$, the concentration at which 50% inhibition occurs, was evaluated based on the difference between the final concentration of the test cells and the initial concentration of the cells incubated in a well not-treated with the test compound which was regarded as 100%. The calculation of $IC_{50}$ was carried out by using Microsoft Excel, and the results are shown in Table 6 and 7.

Test Example 4

Prolongation Study in A431 Cells

A skin cancer cell line, A431 (ATCC: CRL-1555), was used to test the degrees of the inventive compounds in inhibiting EGFR's phosphorylation and the prolongation of ability to inhibit it thereof.

The cell line was incubated in a culture flask at 37° C. under 95% air and 5% $CO_2$ using a culture medium containing DMEM, 10% FBS and 1% PS. When more than 90% of the total volume of the culture flask became filled with cells, the cultured cell solution was subject to secondary incubation and was poured to each well of a 6-well plate to the extent of 500,000 cells/well. After 24 hrs, the cells were separated from the solution, washed with PBS, and incubated in a culture medium containing DMEM, 0.1% FBS and 1% PS for 16 hrs. The compounds obtained in Examples 1, 17, 19 and 36, and Tarceva as EGFR phosphorylation inhibitors were each added to the cell-containing well to a concentration of 1 μM. After 4 hrs, the cells were separated from the solution, washed 4 times with PBS after every 0, 2, 4 and 8 hrs, and incubated in a culture medium containing DMEM, 0.1% FBS and 1% PS. When each of 0, 8, 24 and 48 hrs passed after the washing, the medium was removed therefrom to terminate the reaction. Just before the completion of the reaction, the cultured cell solution was treated with a 100 ng/ml concentration of EGF (Sigma, Cat No. E9644) for 5 mins to induce the activation of EGFR. After the completion of the reaction, the well plate holding the cultured cells was stored at −70° C. In control groups, the replacement of the medium was performed instead of the addition of the EGFR phosphorylation inhibitor, wherein the induction of EGFR activation using EGF was made only in a positive control group and not made in a negative control group.

For Western blot and enzyme immune measuring (ELISA) methods, the well plate stored at −70° C. was allowed to melt to room temperature, and then protein was extracted from the cells in the well plate using a protein extract buffer. The extraction of the protein was performed as follows: 250 μl of the protein extract buffer (Phosphosafe extraction reagent, Calbiochem, Cat No. 71296-3) comprising protease inhibitor cocktail was added to each cell-containing well, which was stirred at room temperature for 5 mins. The cells were collected using a cell scraper and put in an 1.5 ml tube, which was centrifuged at a speed of 16,000×g for 5 mins. The upper layer thus obtained was separated, of which the protein content was determined by a protein assay kit (Bio-rad, Cat No. 500-0116). The protein extracted was diluted with PBS to a concentration of 0.8 mg/ml.

A human EGFR (py1173) immunoassay kit (Biosource, Cat No. KHR9071) was used in the enzyme immune measuring method. 100 μl of the sample which was diluted by 4 folds with a standard dilution buffer in a kit was added to a strip well, which was incubated at a 4° C. refrigerator overnight. The cultured cells was separated therefrom and washed 4 times with 200 μl of a washing buffer. 100 μl of the resulting primary antibody (anti-human EGFR [pY1173]) was put to each strip well, incubated at 37° C. for 1 hr, and washed 4 times with 200 μl of a washing buffer. The resulting secondary antibody (anti-rabbit IgG-HRP) was diluted by 100 folds with an HRP dilution buffer in a kit. 100 μl of the dilute was put to each strip well, incubated at 37° C. for 30 mins, and washed 4 times with 200 μl of the washing buffer. 100 μl of an HRP substrate in a kit was put to each strip well and incubated in a darkroom for 10 to 30 mins. 100 μl of a reaction stop solution was added thereto to terminate the reaction, and then, the absorbance at 450 nm was observed.

Electrophoresis and Western blot methods were conducted based on the conventional methods in the following: An LDS buffer was added to each sample, which was allowed to boil at 70° C. for 10 mins. 10 μl of the resulting solution was loaded to a 12-well gel (Nupage 4~12% Bis-tris gel, Invitrogen), followed by 120 volt-electrophoresis in a buffer (MOPS electrophoresis buffer, Invitrogen, Cat No. NP0006-1) for 2 hrs. After the electrophoresis, the resulting gel was transferred to a nitrocellulose membrane (Bio-rad, Cat No. 162-0251) in a transfer buffer (Invitrogen, Cat No. NP0001) with 30 volt for 2 hrs. The nitrocellulose membrane transferred was allowed to react with a 3% BSA blocking solution at room temperature for 1~2 hrs to inhibit a non-specific antigen-antibody reaction. The primary antibody diluted with the blocking solution (anti-EGFR (Stressgen, Cat No. CSA330, 1:100 dilution)), anti-pEGFR (Santacruz, Cat No. SC 12351-R, 1:500 dilution) and anti-β actin (Sigma, Cat No. A1978, 4 μg/ml dilution) were allowed to react with each other at 4° C. overnight, which was washed 4 times with a washing buffer (TBS-T) for each 10 mins. The secondary antibody diluted with the blocking solution (anti-mouse IgG (Chemicon, Cat No. AP124P, 1:5000 dilution)) and anti-rabbit IgG (Chemicon, Cat No. AP132P, 1:5000 dilution)) were allowed to react with each other at room temperature for 1 hr, which was washed 5 times with the washing buffer for each 10 mins, followed by coloring using an ECL western blot detection reagent (Amersham, Cat No. RPN2209) and disclosure to Hyperfilm (Amersham, Cat No. RPN2103K) in a darkroom. Protein bands were observed by development of the film, and the results are shown in Table 8.

TABLE 6

| Example | $ID_{50}$ (nM) | |
|---|---|---|
| | A431 | SK-Br3 |
| 1 | 4 | 8 |
| 2 | 85 | 316 |
| 3 | 37 | 1300 |
| 4 | 53 | 604 |
| 5 | 33 | 128 |
| 6 | 531 | 1671 |
| 7 | 5 | 8 |
| 8 | 2 | 7 |
| 9 | 15 | 58 |
| 10 | 14 | 7 |
| 11 | 8 | 13 |
| 12 | 19 | 3 |
| 13 | 28 | 17 |
| 14 | 53 | 128 |
| 15 | 5 | 25 |
| 16 | 15 | 7 |
| 17 | 0.3 | 0.3 |

TABLE 6-continued
| | ID$_{50}$ (nM) | |
|---|---|---|
| Example | A431 | SK-Br3 |
| 18 | 6 | 19 |
| 19 | 0.3 | 0.3 |
| 20 | 222 | 57 |
| 21 | 699 | 210 |
| 22 | 7 | 1 |
| 23 | 1.6 | 0.5 |
| 24 | 1 | 0.6 |
| 25 | 1.5 | 0.4 |
| 26 | 1.6 | 6 |
| 27 | 17 | 3 |
| 28 | 41 | 262 |
| 29 | 29 | 19 |
| 30 | 1 | 0.6 |
| 31 | 3.1 | 2.5 |
| 32 | 2.4 | 2.2 |
| 33 | 44 | 35 |
| 34 | 2 | 0.2 |
| 35 | 514 | 3 |
| 36 | 0.4 | 0.3 |
| 37 | 52 | 79 |
| 38 | >10,000 | >10,000 |
| 39 | 6 | 9 |
| 40 | 23 | 37 |
| 41 | 1 | 2 |
| 42 | 1 | 0.7 |
| 43 | 0.9 | 0.7 |
| 44 | 12 | 2 |
| 45 | 43 | 3 |
| 46 | 8 | 2 |
| 47 | 19 | 10 |
| 48 | >1,000 | 8 |
| 49 | 29 | 45 |
| 50 | 179 | 91 |
| 51 | 105 | 19 |
| 52 | 176 | 30 |
| 53 | 32 | 21 |
| 54 | 10 | 2 |
| 55 | 13 | 2 |
| 56 | 3.7 | 0.7 |
| 57 | 17 | 2 |
| 58 | 58 | 20 |
| 59 | 3 | 9 |
| 60 | 93 | 261 |
| 61 | 15 | 11 |
| 62 | 7 | 6 |
| 63 | 9 | 1 |
| 64 | 142 | 11 |
| 65 | 11 | 15 |
| 66 | 8 | 1 |
| 67 | 35 | 10 |
| 68 | 305 | 10 |
| 69 | 65 | 1.7 |
| 70 | 4.6 | 2.1 |
| 71 | 8 | 5 |
| 72 | 61 | 20 |
| 73 | 1.9 | 1.2 |
| 74 | 11 | 1.0 |
| 75 | 400 | 50 |
| 76 | 300 | 100 |
| 77 | 26 | 7 |
| 78 | 109 | 65 |
| 79 | 129 | 37 |
| 80 | 190 | 268 |
| 81 | 38 | 141 |
| 82 | 48 | 134 |
| 83 | 9 | 23 |
| 84 | 8 | 21 |
| 85 | 41 | 395 |
| 86 | 322 | >1,000 |
| 87 | 516 | 469 |
| 88 | 187 | >1,000 |
| 89 | 14 | 85 |
| 90 | 39 | 13 |
| 91 | 50 | 194 |
| 92 | 4 | 8 |
| 93 | 28 | 40 |
TABLE 6-continued
| | ID$_{50}$ (nM) | |
|---|---|---|
| Example | A431 | SK-Br3 |
| 94 | 85 | 123 |
| 95 | 8 | 23 |
| 96 | 8 | 46 |
| 97 | 25 | 94 |
| 98 | 120 | 45 |
| 99 | 165 | 39 |
| 100 | 76 | 15 |
| 101 | 36 | 11 |
| 102 | 9 | 8 |
| 103 | 18 | 7 |
| 104 | 41 | 1.5 |
| 105 | 1.5 | 0.5 |
| 106 | 1 | 0.5 |
| 107 | 2.4 | 0.7 |
| 108 | 9.1 | 6 |
| 109 | 2.7 | 3.5 |
| 110 | 10 | 30 |
| 111 | 4 | 6 |
| 112 | 15 | 0.8 |
| 113 | 6 | 17 |
| Lapatinib | 80 | 40 |
| 114 | 44 | 274 |
| 115 | 381 | 93 |
| 116 | 883 | 327 |
| 117 | 4 | 1.4 |
| 118 | 4 | 2 |
| 119 | 5 | 6 |
| 120 | 3 | 1.3 |
| 121 | 2.2 | 2.5 |
| 122 | 8 | 2.3 |
| 123 | 12 | 5 |
| 124 | 7.5 | 2.8 |
| 125 | 10 | 1 |
| 126 | 5.4 | 0.9 |
| 127 | 3.4 | 2.3 |
| Ex 1* | 39 | 293 |
| 128 | 2.4 | 5.0 |
| 129 | 2.2 | 0.6 |
| 130 | 5.7 | 0.9 |
| 131 | 20 | 0.5 |
| 132 | 8.3 | 0.5 |
| 133 | 0.7 | 0.2 |
| 134 | 979 | 4 |
| 135 | 0.8 | 0.2 |
| 136 | 2.9 | 0.2 |
| 137 | 1.7 | 1.3 |
| 138 | 2.4 | 1.3 |
| 139 | 0.8 | 1.1 |
| 140 | 1.1 | 0.3 |
| Iressa | 28 | 206 |
Ex1* is a compound prepared in Example 1 of International Patent Publication WO 2005/012290:
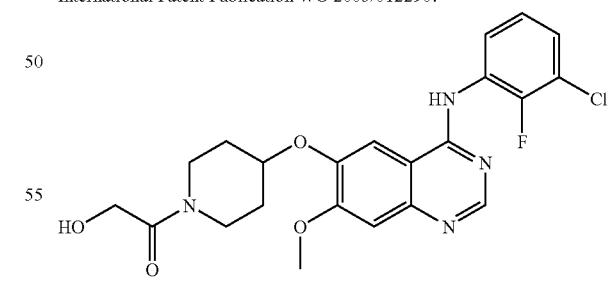
TABLE 7
| | IC$_{50}$ (nM) | | | |
|---|---|---|---|---|
| Example | EGFR | T790M | H1975 | SW-620 |
| 1 | 3 | 1.3 | 80 | >5,000 |
| 7 | 10 | 8 | 55 | >5,000 |

TABLE 7-continued

| | IC$_{50}$ (nM) | | | |
|---|---|---|---|---|
| Example | EGFR | T790M | H1975 | SW-620 |
| 8 | 7 | 1.3 | 37 | >5,000 |
| 10 | 5 | 10 | — | >5,000 |
| 11 | 12 | 27 | 167 | — |
| 15 | 9 | 54 | 413 | — |
| 16 | 8 | 47 | — | >5,000 |
| 17 | 0.7 | 0.8 | 1.5 | >5,000 |
| 19 | 1.1 | 1.9 | 1.3 | >5,000 |
| 22 | 6 | 15 | 156 | — |
| 23 | 6 | 4 | 9 | >5,000 |
| 24 | 6 | 4.5 | 5 | >5,000 |
| 25 | — | 1.3 | 10 | >5,000 |
| 26 | 1.6 | 3.3 | 17.7 | >5,000 |
| 31 | — | — | 50 | — |
| 32 | — | — | 19 | — |
| 34 | 6 | 5 | 22 | >5,000 |
| 36 | 1.3 | 4.4 | 2.7 | >5,000 |
| 39 | — | 7.6 | 48 | — |
| 41 | — | 9.3 | 236 | — |
| 42 | — | 7.1 | 96 | — |
| 43 | 4.2 | 7.2 | 30 | >5,000 |
| 57 | — | — | 16 | >5,000 |
| 58 | — | 16.2 | — | >5,000 |
| 71 | 2.7 | 24 | 70 | — |
| 73 | — | 3 | 27 | >5,000 |
| 104 | — | 2 | 11 | >5,000 |
| 105 | — | 4 | 8 | >5,000 |
| 117 | 0.7 | 3 | 47 | >5,000 |
| 120 | 1.4 | 0.7 | 5.2 | >5,000 |
| 126 | — | 1.8 | 39 | >5,000 |
| 127 | — | 3.8 | 11 | >5,000 |
| 128 | — | 1.4 | 5.0 | >5,000 |
| 129 | — | 3.0 | 50.4 | — |
| 130 | — | 6.6 | 30 | >5,000 |
| 133 | 4.4 | 1.7 | 5.4 | >5,000 |
| 135 | 4.1 | 0.7 | 5.2 | >5,000 |
| 136 | — | 0.9 | 2.6 | >5,000 |
| 139 | — | — | 1.1 | >5,000 |
| Iressa | 639 | >50,00 | >5,000 | >5,000 |
| Lapatinib | 21 | >5,000 | 1,894 | >5,000 |
| BIBW2992 | 13 | — | 84 | 2,641 |
| Ex 1* | 204 | — | >1,000 | — |

TABLE 8

| | EGFR phosphorylation inhibition in A431 cell line (%) | | | | | | | | |
|---|---|---|---|---|---|---|---|---|---|
| | 0 hr | | 8 hrs | | 24 hrs | | 48 hrs | | 72 hrs | |
| Example | Avg. | Var. | Avg. | Var. | Avg. | Var. | Avg. | Var. | Avg. | Var. |
| 1 | 71 | 5.4 | 71 | 8.0 | 73 | 2.2 | 42 | 20.5 | — | — |
| 17 | 87 | 8.6 | 88 | 1.0 | 62 | 21.5 | 31 | 39.7 | 0 | 0.3 |
| 19 | 81 | 7.0 | 86 | 7.9 | 80 | 15.4 | 34 | 14.7 | 0 | 0.5 |
| 36 | 90 | 0.3 | 89 | 4.1 | 81 | 4.4 | 41 | 48.3 | 44 | 7.7 |

As shown in Table 6, each of the inventive compounds showed, at a low concentration thereof, an excellent anticancer activity by effectively inhibiting the growth of A431 and SK-Br3 having overexpressed EGFR and Erb-B2, respectively. Also as shown in Table 7, each of the inventive compounds effectively inhibited the activity of the EGFR T790M mutant kinase and the growth of its expression cell line, H1975, as compared with those of the conventional EGFR inhibitors, i.e., Iressa, Lapatinib, BIBW2992, and Ex1* which is a compound prepared in Example 1 of International Patent Publication WO 2005/012290. In particular, the inventive compounds having A substituent showed a highly improved inhibition activity against H1975 than Ex1*. Whereas, none of the inventive compounds inhibited the growth of SW-620 containing no overexpressed EGFR or Erb-B2. The results of Table 8 suggest that such effects result from irreversible inhibition mechanisms of the inventive compounds which exhibit high EGFR phosphorylation inhibition of 50% more over 24 hrs or longer, as compared with that of the conventional reversible EGFR inhibitor, Tarceva.

Therefore, the compounds of formula (I) of the present invention can effectively inhibit the growth of specific cancer cells induced by the overexpression of EGFR, Erb-B2 or the mutation of EGFR.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I) or a pharmaceutically acceptable salt thereof:

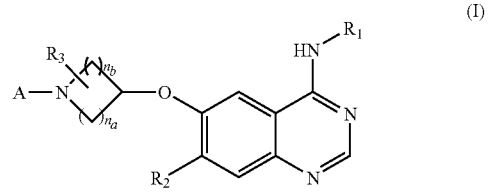

(I)

wherein,

A is

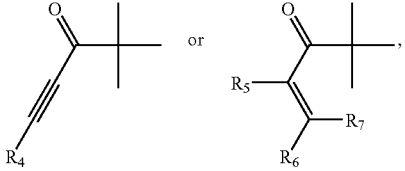

$R_4$, $R_5$, $R_6$ and $R_7$ being each independently hydrogen, halogen, N—$C_{1-6}$ alkyl or N-hydroxy amido or C—$C_{1-6}$ alkyl reverse amido(—NHCOC$_{1-6}$), hydroxycarbonyl (—COOH), $C_{1-6}$ alkyloxycarbonyl (—COOC$_{1-6}$), $C_{1-6}$ alkyl, or $C_{1-6}$ alkyl substituted with a hydroxy, $C_{1-6}$ dialkylamine or 5- or 6-membered heterocyclic group having at least one selected from the group consisting of N, O and S, wherein the 5- or 6-membered heterocyclic group is unsubstituted or substituted with $C_{1-4}$ alkyl;

$R_1$ is a $C_{6-10}$ aryl or 5 to 10-membered heterocyclic group having at least one selected from the group consisting of N, O and S substituted with one to five X, or $C_{1-6}$ alkyl substituted with phenyl;

$R_2$ is hydrogen, hydroxy, $C_{1-6}$ alkoxy, or $C_{1-6}$ alkoxy substituted with $C_{1-6}$ alkoxy or 5- or 6-membered heterocyclic group having at least one selected from the group consisting of N, O and S;

$R_3$ is hydrogen, —COOH, $C_{1-6}$ alkyloxycarbonyl, or amido N-unsubstituted or N-substituted with Y;

$n_a$ and $n_b$ are each an integer ranging from 0 to 6, with the proviso that $n_a$ and $n_b$ are not simultaneously 0; and when $n_a$ is 0, said

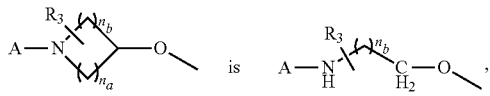

and when $n_b$ is 0, said

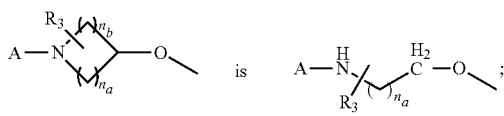

in which:

X is hydrogen, halogen, hydroxy, cyano, nitro, (mono-, di-, or trihalogeno)methyl, mercapto, $C_{1-6}$ alkylthio, acrylamido, $C_{1-6}$ alkyl, $C_{2-6}$ alkenyl, $C_{2-6}$ alkynyl, $C_{1-6}$ alkoxy, phenyloxy, $C_{1-6}$ dialkylamino, or $C_{1-6}$ alkyl or $C_{1-6}$ alkoxy substituted with Z;

Y is hydroxy or $C_{1-6}$ alkyl or $C_{1-6}$ alkyl substituted with Z; and

Z is hydroxy, $C_{1-3}$ alkoxy, $C_{1-3}$ alkylthio, $C_{1-3}$ alkylsulfonyl, di-$C_{1-3}$ alkylamine, $C_{1-6}$ alkyl, phenyl or 5- or 6-membered aromatic or non-aromatic heterocyclic group, said heterocyclic group containing one to four of the moiety selected from the group consisting of N, O, S, SO, and $SO_2$ and said aryl and heterocyclic group being unsubstituted, or substituted with substituents selected from the group consisting of halogen, hydroxyl, amino, nitro, cyano, $C_{1-6}$ alkyl, $C_{2-6}$ alkenyl, $C_{2-6}$ alkynyl, $C_{1-6}$ alkoxy, $C_{1-6}$ monoalkylamino and $C_{1-6}$ dialkylamino.

2. The compound of claim 1, wherein $R_1$ is 3-chloro-4-fluorophenyl, 3-chloro-2-fluorophenyl, 3-chloro-2,4-difluorophenyl, 3,4-dichloro-2-fluorophenyl, 4-bromo-3-chloro-2-fluorophenyl, 4-bromo-2-fluorophenyl, (R)-1-phenylethyl, 3-chloro-4-(3-fluorobenzyloxy)phenyl, 3-chloro-4-(pyridin-2-ylmethoxy)phenyl, 1-(3-fluorobenzyl)-1H-5-indazole, 3-ethynylphenyl, 4-chloro-2,5-dimethoxyphenyl, 4-bromo-3-methylphenyl, 4-isopropylphenyl, 3-methylphenyl, 3-bromophenyl, 3-chlorophenyl, 3,4-dichlorophenyl, 2,3,4-trifluorophenyl, 4-fluoro-3-methylphenyl, 3,4-dimethylphenyl, 4-phenyloxyphenyl, 2,3-dihydro-1H-indenyl, 4-hydroxy-3,5-dichlorophenyl, 3-hydroxy-4-chlorophenyl, 4-hydroxy-2-chlorophenyl, 2-hydroxy-4-chlorophenyl, 3-cyanophenyl, 3-trifluoromethylphenyl, 3-chloro-2-methoxyphenyl, 4-chloro-3-methylphenyl, 4-bromo-3-chlorophenyl, 4-bromo-3-fluorophenyl, 3-chloro-2-methylphenyl, 3-dimethylaminophenyl, 2-fluoro-3-trifluoromethylphenyl, 3-cyano-4-fluorophenyl, 3-cyano-4-chlorophenyl, 3-methylthiophenyl, 2-chlorophenyl, 4-chlorophenyl, 3-chlorophenylmethyl, 3-vinylphenyl, 3-nitrophenyl, 3-acrylamidophenyl, 3-mercaptophenyl, 3-chloromethylphenyl, 4-hydroxy-3-chlorophenyl or 4-hydroxy-3-fluorophenyl;

$R_2$ is hydrogen, hydroxy, methoxy, ethoxy, 3-morpholinopropyloxy or methoxyethoxy;

$R_3$ is hydrogen, methyloxycarbonyl, carboxyl, amido, N-methylamido, N-ethylamido, N-propylamido, N-isopropylamido, N-hydroxyamido, N-2-hydroxyethylamido, N-3-hydroxypropylamido, N-2-methoxyethylamido, N-2-methylthioethylamido, N-2-methylsulfonylethylamido, N-2-N,N'-diethylaminoethylamido, or N-2-morpholinoethylamido;

$R_4$, $R_5$, $R_6$ and $R_7$ being each independently hydrogen, methyl, 4-methylpiperazinylmethyl, 4-methyl piperazinylethyl, N,N'-dimethylaminomethyl, N,N'-diethylaminomethyl, morpholinomethyl, pyrrolidin-1-ylmethyl, piperidin-1-ylmethyl, hydroxymethyl, N-methylcarboxamido, acetamido, N-hydroxyamido, methoxycarbonyl, chloro or carboxyl; and $n_a$ and $n_b$ being each independently an integer ranging from 0 to 2.

3. The compound of claim 1, which is selected from the group consisting of:

1) 1-((3S)-3-(4-(3-chloro-2,4-difluorophenylamino)-7-methoxyquinazolin-6-yloxy)pyrrolidin-1-yl)prop-2-en-1-one;
2) (E)-1-((3S)-3-(4-(3-chloro-2,4-difluorophenylamino)-7-methoxyquinazolin-6-yloxy)pyrrolidin-1-yl)but-2-en-1-one;
3) 1-((3S)-3-(4-(3-chloro-2,4-difluorophenylamino)-7-methoxyquinazolin-6-yloxy)pyrrolidin-1-yl)but-2-yn-1-one;
4) 1-((3S)-3-(4-(3-chloro-2,4-difluorophenylamino)-7-methoxyquinazolin-6-yloxy)pyrrolidin-1-yl)-5-(4-methylpiperazin-1-yl)pent-2-yn-1-one;
5) 1-((3S)-3-(4-(3-chloro-2,4-difluorophenylamino)-7-methoxyquinazolin-6-yloxy)pyrrolidin-1-yl)-4-(dimethylamino)but-2-yn-1-one;
6) 1-((3S)-3-(4-(3-chloro-2-fluorophenylamino)-7-methoxyquinazolin-6-yloxy)pyrrolidin-1-yl)prop-2-en-1-one;
7) 1-((3S)-3-(4-(4-bromo-3-chloro-2-fluorophenylamino)-7-methoxyquinazolin-6-yloxy)pyrrolidin-1-yl)prop-2-en-1-one;
8) 1-((3S)-3-(4-(3,4-dichloro-2-fluorophenylamino)-7-methoxyquinazolin-6-yloxy)pyrrolidin-1-yl)prop-2-en-1-one;
9) 1-((3S)-3-(4-(4-bromo-2-fluorophenylamino)-7-methoxyquinazolin-6-yloxy)pyrrolidin-1-yl)prop-2-en-1-one;
10) 1-((3S)-3-(4-(3-chloro-4-(pyridin-2-ylmethoxy)phenylamino)-7-methoxyquinazolin-6-yloxy)pyrrolidin-1-yl)prop-2-en-1-one;
11) 1-((3S)-3-(7-methoxy-4-((1R)-1-phenylethylamine)quinazolin-6-yloxy)pyrrolidin-1-yl)prop-2-en-1-one;
12) 1-((3S)-3-(4-(1-(3-fluorobenzyl)-1H-indazol-5-ylamino)-7-methoxyquinazolin-6-yloxy)pyrrolidin-1-yl)prop-2-en-1-one;
13) 1-((3S)-3-(4-(3-chloro-4-fluorophenylamino)-7-methoxyquinazolin-6-yloxy)pyrrolidin-1-yl)prop-2-en-1-one;
14) 1-((3R)-3-(4-(3-chloro-4-fluorophenylamino)-7-methoxyquinazolin-6-yloxy)pyrrolidin-1-yl)prop-2-en-1-one;
15) 1-((3S)-3-(4-(3-chloro-2,4-difluorophenylamino)quinazolin-6-yloxy)pyrrolidin-1-yl)prop-2-en-1-one;
16) 1-((3S)-3-(4-(3-chloro-4-(3-fluorobenzyloxy)phenylamino)quinazolin-6-yloxy)pyrrolidin-1-yl)prop-2-en-1-one;
17) 1-(3-(4-(3-chloro-2,4-difluorophenylamino)-7-methoxyquinazolin-6-yloxy)azetidin-1-yl)prop-2-en-1-one;

18) 1-(3-(4-(3-chloro-2,4-difluorophenylamino)-7-methoxyquinazolin-6-yloxy)piperidin-1-yl)prop-2-en-1-one;
19) 1-(4-(4-(3-chloro-2,4-difluorophenylamino)-7-methoxyquinazolin-6-yloxy)piperidin-1-yl)prop-2-en-1-one;
20) 1-((3R)-3-(4-(3-chloro-2,4-difluorophenylamino)-7-methoxyquinazolin-6-yloxy)pyrrolidin-1-yl)prop-2-en-1-one;
21) N-(2-(4-(3-chloro-2,4-difluorophenylamino)-7-methoxyquinazolin-6-yloxy)ethyl)acrylamide;
22) 1-(3-(7-methoxy-4-((1R)-1-phenylethylamino)quinazolin-6-yloxy)azetidin-1-yl)prop-2-en-1-one;
23) 1-(3-(4-(3-chloro-2-fluorophenylamino)-7-methoxyquinazolin-6-yloxy)azetidin-1-yl)prop-2-en-1-one;
24) 1-(3-(4-(3,4-dichloro-2-fluorophenylamino)-7-methoxyquinazolin-6-yloxy)azetidin-1-yl)prop-2-en-1-one;
25) 1-(3-(4-(3-chloro-4-fluorophenylamino)-7-methoxyquinazolin-6-yloxy)azetidin-1-yl)prop-2-en-1-one;
26) 1-(3-(4-(3-chlorophenylamino)-7-methoxyquinazolin-6-yloxy)azetidin-1-yl)prop-2-en-1-one;
27) 3-(6-(1-acryloylazetidin-3-yloxy)-7-methoxyquinazolin-4-ylamino)benzonitrile;
28) (E)-4-(3-(4-(3-chloro-2,4-difluorophenylamino)-7-methoxyquinazolin-6-yloxy)azetidin-1-yl)-N-methyl-4-oxobut-2-enamide;
29) 1-(3-(4-(3-chloro-2,4-difluorophenylamino)-7-methoxyquinazolin-6-yloxy)azetidin-1-yl)-2-methylprop-2-en-1-one;
30) (Z)-methyl-4-(3-(4-(3-chloro-2-fluorophenylamino)-7-methoxyquinazolin-6-yloxy)azetidin-1-yl)-4-oxobut-2-enoate;
31) N-(3-3-(4-(3-chloro-2,4-difluorophenylamino)-7-methoxyquinazolin-6-yloxy)azetidin-1-yl)-3-oxoprop-1-en-2-yl)acetamide;
32) (Z)-3-chloro-1-(3-(4-(3-chloro-2,4-difluorophenylamino)-7-methoxyquinazolin-6-yloxy)azetidin-1-yl)prop-2-en-1-one;
33) (E)-3-chloro-1-(3-(4-(3-chloro-2,4-difluorophenylamino)-7-methoxyquinazolin-6-yloxy)azetidin-1-yl)prop-2-en-1-one;
34) 1-(4-(4-(3-chloro-2-fluorophenylamino)-7-methoxyquinazolin-6-yloxy)piperidin-1-yl)prop-2-en-1-one;
35) 1-(4-(7-methoxy-4-((1R)-1-phenylethylamino)quinazolin-6-yloxy)piperidin-1-yl)prop-2-en-1-one;
36) 1-(4-(4-(3,4-dichloro-2-fluorophenylamino)-7-methoxyquinazolin-6-yloxy)piperidin-1-yl)prop-2-en-1-one;
37) 1-(4-(4-(3-ethinylphenylamino)-7-methoxyquinazolin-6-yloxy)piperidin-1-yl)prop-2-en-1-one;
38) 1-(4-(4-(4-chloro-2,5-dimethoxyphenylamino)-7-methoxyquinazolin-6-yloxy)piperidin-1-yl)prop-2-en-1-one;
39) 1-(4-(4-(4-bromo-3-methylphenylamino)-7-methoxyquinazolin-6-yloxy)piperidin-1-yl)prop-2-en-1-one;
40) 1-(4-(4-(4-isopropylphenylamino)-7-methoxyquinazolin-6-yloxy)piperidin-1-yl)prop-2-en-1-one;
41) 1-(4-(4-(m-toluidino)-7-methoxyquinazolin-6-yloxy)piperidin-1-yl)prop-2-en-1-one;
42) 1-(4-(4-(3-bromophenylamino)-7-methoxyquinazolin-6-yloxy)piperidin-1-yl)prop-2-en-1-one;
43) 1-(4-(4-(3-chlorophenylamino)-7-methoxyquinazolin-6-yloxy)piperidin-1-yl)prop-2-en-1-one;
44) 1-(4-(4-(3,4-dichlorophenylamino)-7-methoxyquinazolin-6-yloxy)piperidin-1-yl)prop-2-en-1-one;
45) 1-(4-(7-methoxy-4-(2,3,4-trifluorophenylamino)quinazolin-6-yloxy)piperidin-1-yl)prop-2-en-1-one;
46) 1-(4-(4-(4-fluoro-3-methylphenylamino)-7-methoxyquinazolin-6-yloxy)piperidin-1-yl)prop-2-en-1-one;
47) 1-(4-(4-(3,4-dimethylphenylamino)-7-methoxyquinazolin-6-yloxy)piperidin-1-yl)prop-2-en-1-one;
48) 1-(4-(7-methoxy-4-(4-phenoxyphenylamino)quinazolin-6-yloxy)piperidin-1-yl)prop-2-en-1-one;
49) 1-(4-(4-(2,3-dihydro-1H-inden-5-ylamino)-7-methoxyquinazolin-6-yloxy)piperidin-1-yl)prop-2-en-1-one;
50) 1-(4-(4-(3,5-dichloro-4-hydroxyphenylamino)-7-methoxyquinazolin-6-yloxy)piperidin-1-yl)prop-2-en-1-one;
51) 1-(4-(4-(4-chloro-3-hydroxyphenylamino)-7-methoxyquinazolin-6-yloxy)piperidin-1-yl)prop-2-en-1-one;
52) 1-(4-(4-(2-chloro-4-hydroxyphenylamino)-7-methoxyquinazolin-6-yloxy)piperidin-1-yl)prop-2-en-1-one;
53) 1-(4-(4-(4-chloro-2-hydroxyphenylamino)-7-methoxyquinazolin-6-yloxy)piperidin-1-yl)prop-2-en-1-one;
54) 1-(4-(4-(3-chloro-4-(3-fluorobenzyloxy)phenylamino)-7-methoxyquinazolin-6-yloxy)piperidin-1-yl)prop-2-en-1-one;
55) 1-(4-(4-(3-chloro-4-(pyridin-2-ylmethoxy)phenylamino)-7-methoxyquinazolin-6-yloxy)piperidin-1-yl)prop-2-en-1-one;
56) 3-(6-(1-acryloylpiperidin-4-yloxy)-7-methoxyquinazolin-4-ylamino)benzonitrile;
57) 1-(4-(4-(3-chloro-4-fluorophenylamino)-7-methoxyquinazolin-6-yloxy)piperidin-1-yl)prop-2-en-1-one;
58) 1-(4-(7-methoxy-4-3-(trifluoromethyl)phenylamino)quinazolin-6-yloxy)piperidin-1-yl)prop-2-en-1-one;
59) 1-(4-(4-(3-chloro-2-methoxyphenylamino)-7-methoxyquinazolin-6-yloxy)piperidin-1-yl)prop-2-en-1-one;
60) 1-(4-(4-(4-chloro-3-methylphenylamino)-7-methoxyquinazolin-6-yloxy)piperidin-1-yl)prop-2-en-1-one;
61) 1-(4-(4-(4-bromo-3-chlorophenylamino)-7-methoxyquinazolin-6-yloxy)piperidin-1-yl)prop-2-en-1-one;
62) 1-(4-(4-(4-bromo-3-fluorophenylamino)-7-methoxyquinazolin-6-yloxy)piperidin-1-yl)prop-2-en-1-one;
63) 1-(4-(4-(3-chloro-2-methylphenylamino)-7-methoxyquinazolin-6-yloxy)piperidin-1-yl)prop-2-en-1-one;
64) 1-(4-(4-(3-(dimethylamino)phenylamino)-7-methoxyquinazolin-6-yloxy)piperidin-1-yl)prop-2-en-1-one;
65) 1-(4-(4-(2-fluoro-3-(trifluoromethyl)phenylamino)-7-methoxyquinazolin-6-yloxy)piperidin-1-yl)prop-2-en-1-one;
66) 5-(6-(1-acryloylpiperidin-4-yloxy)-7-methoxyquinazolin-4-ylamino)-2-fluorobenzonitrile;
67) 5-(6-(1-acryloylpiperidin-4-yloxy)-7-methoxyquinazolin-4-ylamino)-2-chlorobenzonitrile;
68) 1-(4-(7-methoxy-4-(3-(methylthio)phenylamino)quinazolin-6-yloxy)piperidin-1-yl)prop-2-en-1-one;
69) 1-(4-(4-(2-chlorophenylamino)-7-methoxyquinazolin-6-yloxy)piperidin-1-yl)prop-2-en-1-one;
70) 1-(4-(4-(4-chlorophenylamino)-7-methoxyquinazolin-6-yloxy)piperidin-1-yl)prop-2-en-1-one;
71) 1-(4-(4-(3-chloro-2,4-difluorophenylamino)quinazolin-6-yloxy)piperidin-1-yl)prop-2-en-1-one;
72) 1-(4-(4-(3-chlorobenzylamino)-7-methoxyquinazolin-6-yloxy)piperidin-1-yl)prop-2-en-1-one;
73) 1-(4-(7-methoxy-4-(3-vinylphenylamino)quinazolin-6-yloxy)piperidin-1-yl)prop-2-en-1-one;
74) 1-(4-(7-methoxy-4-(3-nitrophenylamino)quinazolin-6-yloxy)piperidin-1-yl)prop-2-en-1-one;
75) N-(3-(6-(1-acryloylpiperidin-4-yloxy)-7-quinazolin-4-ylamino)phenyl)acrylamide;

76) 1-(4-(4-(3-merchaptophenylamino)-7-methoxyquinazolin-6-yloxy)piperidin-1-yl)prop-2-en-1-one;
77) 1-(4-(4-(3-chloromethyl)phenylamino)-7-methoxyquinazolin-6-yloxy)piperidin-1-yl)prop-2-en-1-one;
78) 1-(4-(4-(3-chloro-4-hydroxyphenylamino)-7-methoxyquinazolin-6-yloxy)piperidin-1-yl)prop-2-en-1-one;
79) 1-(4-(4-(3-fluoro-4-hydroxyphenylamino)-7-methoxyquinazolin-6-yloxy)piperidin-1-yl)prop-2-en-1-one;
80) 1-(4-(4-(3-chloro-2,4-difluorophenylamino)-7-methoxyquinazolin-6-yloxy)piperidin-1-yl)but-2-yn-1-one;
81) 1-(4-(4-(3-chloro-2,4-difluorophenylamino)-7-methoxyquinazolin-6-yloxy)piperidin-1-yl)-3-methylbut-2-en-1-one;
82) (E)-4-(4-(4-(3-chloro-2,4-difluorophenylamino)-7-methoxyquinazolin-6-yloxy)piperidin-1-yl)-N-methyl-4-oxobut-2-enamide;
83) (Z)-methyl-(4-(4-(3-chloro-2,4-difluorophenylamino)-7-methoxyquinazolin-6-yloxy)piperidin-1-yl)-4-oxobut-2-enoate;
84) (Z)-methyl-(4-(4-(3,4-dichloro-2-difluorophenylamino)-7-methoxyquinazolin-6-yloxy)piperidin-1-yl)-4-oxobut-2-enoate;
85) (Z)-4-(4-(4-(3-chloro-2,4-difluorophenylamino)-7-methoxyquinazolin-6-yloxy)piperidin-1-yl)-4-oxobut-2-enoic acid;
86) (Z)-4-(4-(4-(3,4-dichloro-2-fluorophenylamino)-7-methoxyquinazolin-6-yloxy)piperidin-1-yl)-4-oxobut-2-enoic acid;
87) (E)-4-(4-(4-(3,4-dichloro-2-fluorophenylamino)-7-methoxyquinazolin-6-yloxy)piperidin-1-yl)-4-oxobut-2-enoic acid;
88) (E)-4-(4-(4-(3-chloro-2,4-difluorophenylamino)-7-methoxyquinazolin-6-yloxy)piperidin-1-yl)-N-hydroxy-4-oxobut-2-enamide;
89) (Z)-3-chloro-1-(4-(4-(3,4-dichloro-2-fluorophenylamino)-7-methoxyquinazolin-6-yloxy)piperidin-1-yl)prop-2-en-1-one;
90) (E)-3-chloro-1-(4-(4-(3,4-dichloro-2-fluorophenylamino)-7-methoxyquinazolin-6-yloxy)piperidin-1-yl)prop-2-en-1-one;
91) N-(3-(4-(4-(3,4-dichloro-2-fluorophenylamino)-7-methoxyquinazolin-6-yloxy)piperidin-1-yl)-3-oxoprop-1-en-2-yl)acetamide;
92) (E)-1-((3S)-3-(4-(3-chloro-2,4-difluorophenylamino)-7-methoxyquinazolin-6-yloxy)pyrrolidin-1-yl)-4-(dimethylamino)but-2-en-1-one;
93) (E)-1-((3S)-3-(4-(3-chloro-2,4-difluorophenylamino)-7-methoxyquinazolin-6-yloxy)pyrrolidin-1-yl)-4-(dimethylamino)but-2-en-1-one;
94) (E)-1-((3S)-3-(4-(3-chloro-2,4-difluorophenylamino)-7-methoxyquinazolin-6-yloxy)pyrrolidin-1-yl)-4-morpholinobut-2-en-1-one;
95) (E)-1-((3S)-3-(4-(3-chloro-2,4-difluorophenylamino)-7-methoxyquinazolin-6-yloxy)pyrrolidin-1-yl)-4-(pyrrolidin-1-yl)but-2-en-1-one;
96) (E)-1-((3S)-3-(4-(3-chloro-2-fluorophenylamino)-7-methoxyquinazolin-6-yloxy)pyrrolidin-1-yl)-4-(dimethylamino)but-2-en-1-one;
97) (E)-1-((3S)-3-(4-(3-chloro-2,4-fluorophenylamino)quinazolin-6-yloxy)pyrrolidin-1-yl)-4-(dimethylamino)but-2-en-1-one;
98) (E)-1-(4-(4-(3-chloro-2,4-difluorophenylamino)-7-methoxyquinazolin-6-yloxy)piperidin-1-yl)-4-(dimethylamino)but-2-en-1-one;
99) (E)-1-(4-(4-(3,4-dichloro-2-difluorophenylamino)-7-methoxyquinazolin-6-yloxy)piperidin-1-yl)-4-(dimethylamino)but-2-en-1-one;
100) (E)-1-(4-(4-(3-chloro-2-fluorophenylamino)-7-methoxyquinazolin-6-yloxy)piperidin-1-yl)-4-(dimethylamino)but-2-en-1-one;
101) (E)-1-(3-(4-(3-chloro-2,4-difluorophenylamino)-7-methoxyquinazolin-6-yloxy)azetidin-1-yl)-4-(dimethylamino)but-2-en-1-one;
102) (E)-1-(3-(4-(3-chloro-2,4-difluorophenylamino)-7-methoxyquinazolin-6-yloxy)azetidin-1-yl)-4-(dimethylamino)but-2-en-1-one;
103) (E)-N-(2-(4-(3-chloro-2,4-difluorophenylamino)-7-methoxyquinazolin-6-yloxy)ethyl)-4-(dimethylamino)but-2-enamide;
104) 1-(3-(4-(3-chloro-2,4-difluorophenylamino)-7-methoxyquinazolin-6-yloxy)azetidin-1-yl)-2-((dimethylamino)methyl)prop-2-en-1-one;
105) 1-(3-(4-(3-chloro-2,4-difluorophenylamino)-7-methoxyquinazolin-6-yloxy)azetidin-1-yl)-2-((morpholinomethyl)prop-2-en-1-one;
106) 1-(3-(4-(3-chloro-2,4-difluorophenylamino)-7-methoxyquinazolin-6-yloxy)azetidin-1-yl)-2-((4-methylpiperazin-1-yl)methyl)prop-2-en-1-one;
107) 1-(3-(4-(3-chloro-2-fluorophenylamino)-7-methoxyquinazolin-6-yloxy)azetidin-1-yl)-2-(piperidin-1-ylmethyl)prop-2-en-1-one;
108) 1-(3-(4-(3-chloro-2,4-difluorophenylamino)-7-methoxyquinazolin-6-yloxy)azetidin-1-yl)-2-(piperidin-1-ylmethyl)prop-2-en-1-one;
109) 1-(4-(4-(3-chloro-2,4-difluorophenylamino)-7-methoxyquinazolin-6-yloxy)piperidin-1-yl)-2-((dimethylamino)methyl)prop-2-en-1-one;
110) 1-(4-(4-(3-chloro-2,4-difluorophenylamino)-7-methoxyquinazolin-6-yloxy)piperidin-1-yl)-2-(morpholinomethyl)prop-2-en-1-one;
111) 1-(4-(4-(3,4-dichloro-2-fluorophenylamino)-7-methoxyquinazolin-6-yloxy)piperidin-1-yl)-2-((dimethylamino)methyl)prop-2-en-1-one;
112) (Z)-1-(3-(4-(3-chloro-2,4-difluorophenylamino)-7-methoxyquinazolin-6-yloxy)azetidin-1-yl)-4-(dimethylamino)but-2-en-1-one;
113) (Z)-1-(4-(4-(3-chloro-2,4-difluorophenylamino)-7-methoxyquinazolin-6-yloxy)piperidin-1-yl)-2-(dimethylamino)but-2-en-1-one;
114) 1-(4-(4-(3,4-dichloro-2-fluorophenylamino)-7-methoxyquinazolin-6-yloxy)piperidin-1-yl)-2-(hydroxymethyl)prop-2-en-1-one;
115) 1-(3-(4-(3-chloro-2,4-difluorophenylamino)-7-hydroxyquinazolin-6-yloxy)azetidin-1-yl)prop-2-en-1-one;
116) 1-(3-(4-(3-chloro-2,4-difluorophenylamino)-7-(2-methoxyethoxy)quinazolin-6-yloxy)azetidin-1-yl)prop-2-en-1-one;
117) 1-(4-(4-(3-chloro-2,4-difluorophenylamino)-7-(2-methoxyethoxy)quinazolin-6-yloxy)piperidin-1-yl)prop-2-en-1-one;
118) 1-(4-(4-(3-chloro-2,4-difluorophenylamino)-7-(3-morpholinopropoxy)quinazolin-6-yloxy)piperidin-1-yl)prop-2-en-1-one;
119) (2S,4S)-methyl-1-acryloyl-4-(4-(3-chloro-2,4-difluorophenylamino)-7-methoxyquinazolin-6-yloxy)piperidin-2-carboxylate;
120) (2S,4S)-1-acryloyl-4-(4-(3-chloro-2,4-difluorophenylamino)-7-methoxyquinazolin-6-yloxy)piperidin-2-carboxamide;
121) (2S,4S)-1-acryloyl-4-(4-(3-chloro-2,4-difluorophenylamino)-7-methoxyquinazolin-6-yloxy)-N-methylpiperidin-2-carboxamide;

122) (2S,4,5)-1-acryloyl-4-(4-(3-chloro-2,4-difluorophenylamino)-7-methoxyquinazolin-6-yloxy)-N-ethylpiperidin-2-carboxamide;
123) (2S,4S)-1-acryloyl-4-(4-(3-chloro-2,4-difluorophenylamino)-7-methoxyquinazolin-6-yloxy)-N-propylpiperidin-2-carboxamide;
124) (2S,4S)-1-acryloyl-4-(4-(3-chloro-2,4-difluorophenylamino)-7-methoxyquinazolin-6-yloxy)-N-isopropylpiperidin-2-carboxamide;
125) (2S,4S)-1-acryloyl-4-(4-(3-chloro-2,4-difluorophenylamino)-7-methoxyquinazolin-6-yloxy)-N-hydroxypiperidin-2-carboxamide;
126) (2S,4S)-1-acryloyl-4-(4-(3-chloro-2,4-difluorophenylamino)-7-methoxyquinazolin-6-yloxy)-N-(2-hydroxyethyl)piperidin-2-carboxamide;
127) (2S,4S)-1-acryloyl-4-(4-(3-chloro-2,4-difluorophenylamino)-7-methoxyquinazolin-6-yloxy)-N-(2-methoxyethyl)piperidin-2-carboxamide;
128) (2S,4S)-1-acryloyl-4-(4-(3-chloro-2,4-difluorophenylamino)-7-methoxyquinazolin-6-yloxy)-N-(2-(methylthio)ethyl)piperidin-2-carboxamide;
129) (2S,4S)-1-acryloyl-4-(4-(3-chloro-2,4-difluorophenylamino)-7-methoxyquinazolin-6-yloxy)-N-(2-(methylsulphonyl)ethyl)piperidin-2-carboxamide;
130) (2S,4S)-1-acryloyl-4-(4-(3-chloro-2,4-difluorophenylamino)-7-methoxyquinazolin-6-yloxy)-N-(2-(dimethylamino)ethyl)piperidin-2-carboxamide;
131) (2S,4S)-1-acryloyl-4-(4-(3-chloro-2,4-difluorophenylamino)-7-methoxyquinazolin-6-yloxy)-N-(3-hydroxypropyl)piperidin-2-carboxamide;
132) (2S,4S)-1-acryloyl-4-(4-(3-chloro-2,4-difluorophenylamino)-7-methoxyquinazolin-6-yloxy)-N-(2-morpholinoethyl)piperidin-2-carboxamide;
133) (2R,4R)-methyl-1-acryloyl-4-(4-(3-chloro-2,4-difluorophenylamino)-7-methoxyquinazolin-6-yloxy)piperidin-2-carboxamide;
134) (2R,4R)-1-acryloyl-4-(4-(3-chloro-2,4-difluorophenylamino)-7-methoxyquinazolin-6-yloxy)piperidin-2-carboxyl acid;
135) (2R,4R)-1-acryloyl-4-(4-(3-chloro-2,4-difluorophenylamino)-7-methoxyquinazolin-6-yloxy)piperidin-2-carboxamide;
136) (2R,4R)-1-acryloyl-4-(4-(3-chloro-2,4-difluorophenylamino)-7-methoxyquinazolin-6-yloxy)-N-methylpiperidin-2-carboxamide;
137) (2R,4R)-1-acryloyl-4-(4-(3-chloro-2,4-difluorophenylamino)-7-methoxyquinazolin-6-yloxy)-N-hydroxypiperidin-2-carboxamide;
138) (2R,4R)-1-acryloyl-4-(4-(3-chloro-2,4-difluorophenylamino)-7-methoxyquinazolin-6-yloxy)-N-(2-(methylsulphonyl)ethyl)piperidin-2-carboxamide;
139) (2R,4R)-1-acryloyl-4-(4-(3,4-dichloro-2-fluorophenylamino)-7-methoxyquinazolin-6-yloxy)piperidin-2-carboxamide; and
140) (2R,4R)-1-acryloyl-4-(4-(4-bromo-2-fluorophenylamino)-7-methoxyquinazolin-6-yloxy)piperidin-2-carboxamide.

4. A pharmaceutical composition comprising the compound or its pharmaceutically acceptable salt of claim 1 as an active ingredient and a pharmaceutically acceptable carrier.

* * * * *